US011028068B2

(12) United States Patent
Zhao et al.

(10) Patent No.: US 11,028,068 B2
(45) Date of Patent: Jun. 8, 2021

(54) SOMATOSTATIN MODULATORS AND USES THEREOF

(71) Applicant: Crinetics Pharmaceuticals, Inc., San Diego, CA (US)

(72) Inventors: Jian Zhao, San Diego, CA (US); Yunfei Zhu, San Diego, CA (US); Shimiao Wang, San Diego, CA (US); Sangdon Han, San Diego, CA (US); Sun Hee Kim, San Diego, CA (US)

(73) Assignee: CRINETICS PHARMACEUTICALS, INC., San Diego, CA (US)

( * ) Notice: Subject to any disclaimer, the term of this patent is extended or adjusted under 35 U.S.C. 154(b) by 0 days.

(21) Appl. No.: 16/631,423

(22) PCT Filed: Jul. 24, 2018

(86) PCT No.: PCT/US2018/043556
§ 371 (c)(1),
(2) Date: Jan. 15, 2020

(87) PCT Pub. No.: WO2019/023278
PCT Pub. Date: Jan. 31, 2019

(65) Prior Publication Data
US 2020/0207737 A1 Jul. 2, 2020

Related U.S. Application Data

(60) Provisional application No. 62/536,814, filed on Jul. 25, 2017.

(51) Int. Cl.
| | | |
|---|---|---|
| *C07D 215/50* | (2006.01) | |
| *A61K 31/47* | (2006.01) | |
| *C07D 401/12* | (2006.01) | |
| *C07D 471/04* | (2006.01) | |
| *A61K 9/00* | (2006.01) | |

(52) U.S. Cl.
CPC ......... *C07D 401/12* (2013.01); *C07D 215/50* (2013.01); *C07D 471/04* (2013.01); *A61K 9/0053* (2013.01)

(58) Field of Classification Search
CPC .... C07D 215/50; C07D 471/04; A61K 31/47; A61K 31/4375
USPC .......................... 546/169, 122; 514/311, 300
See application file for complete search history.

(56) References Cited

U.S. PATENT DOCUMENTS

| | | | |
|---|---|---|---|
| 4,335,127 | A | 6/1982 | Vandenberk et al. |
| 5,952,328 | A | 9/1999 | Bihovsky et al. |
| 5,962,457 | A | 10/1999 | Chenard et al. |
| 6,011,036 | A | 1/2000 | Lohray et al. |
| 6,124,302 | A | 9/2000 | Corbett et al. |
| 6,127,375 | A | 10/2000 | Corbett |
| 6,136,812 | A | 10/2000 | Chenard et al. |
| 6,175,009 | B1 | 1/2001 | Confalone et al. |
| 6,323,208 | B1 | 11/2001 | Chenard et al. |
| 6,358,948 | B1 | 3/2002 | Zhang et al. |
| 6,423,718 | B1 | 7/2002 | Corbett et al. |
| 6,492,520 | B1 | 12/2002 | Chen |
| 6,498,154 | B1 | 12/2002 | Grubb et al. |
| 6,667,300 | B2 | 12/2003 | Sadhu et al. |
| 6,693,103 | B2 | 2/2004 | Zhang et al. |
| 6,730,682 | B2 | 5/2004 | Schnute et al. |
| 6,946,469 | B2 | 9/2005 | Corbett et al. |
| 7,015,233 | B2 | 3/2006 | Gomtsyan et al. |
| 7,034,039 | B2 | 4/2006 | Oi et al. |
| 7,115,634 | B2 | 10/2006 | Thurieau et al. |
| 7,160,888 | B2 | 1/2007 | Clark et al. |
| 7,226,923 | B2 | 6/2007 | Boyd et al. |
| 7,501,410 | B2 | 3/2009 | Goldstein et al. |
| 7,648,984 | B2 | 1/2010 | Miller et al. |
| 7,696,215 | B2 | 4/2010 | Nash et al. |
| 7,737,155 | B2 | 6/2010 | Palani et al. |
| 7,737,274 | B2 | 6/2010 | Kataoka et al. |
| 7,750,015 | B2 | 7/2010 | Palani et al. |
| 7,750,154 | B2 | 7/2010 | Brown et al. |
| 7,763,616 | B2 | 7/2010 | Yu et al. |
| 7,767,817 | B2 | 8/2010 | Wang et al. |
| 7,786,115 | B2 | 8/2010 | Nash et al. |
| 7,939,539 | B2 | 5/2011 | Wang et al. |
| 7,960,384 | B2 | 6/2011 | Feng et al. |
| 8,026,256 | B2 | 9/2011 | Gomtsyan et al. |
| 8,071,762 | B2 | 12/2011 | Gomtsyan et al. |
| 8,093,299 | B2 | 1/2012 | Geibel et al. |
| 8,188,117 | B2 | 5/2012 | Plettenburg et al. |
| 8,207,163 | B2 | 6/2012 | Bhat et al. |
| 8,314,094 | B2 | 11/2012 | Ishikawa et al. |

(Continued)

FOREIGN PATENT DOCUMENTS

| | | |
|---|---|---|
| CA | 2644929 A1 | 5/2008 |
| EP | 0530994 A1 | 3/1993 |

(Continued)

OTHER PUBLICATIONS

Berge et al. Pharmaceutical Salts. Journal of Pharmaceutical Sciences 66(1):1-19 (Jan. 1977).
Brazeau et al. Hypothalamic polypeptide that inhibits the secretion of immunoreactive pituitary growth hormone. Science 179:77-79 (1973).
Bundgaard. Design and Application of Prodrugs. Textbook of Drug Design and Development. Krosgaard-Larsen and Bundgaard. Chapter 5. pp. 113-191 (1991).
Bundgaard. Means to Enhance Penetration: Prodrugs as a Means to Improve the Delivery of Peptide Drugs. Advanced Drug Delivery Review 8:1-38 (1992).

(Continued)

*Primary Examiner* — Charanjit Aulakh
(74) *Attorney, Agent, or Firm* — Wilson Sonsini Goodrich & Rosati

(57) ABSTRACT

Described herein are compounds that are somatostatin modulators, methods of making such compounds, pharmaceutical compositions and medicaments comprising such compounds, and methods of using such compounds in the treatment of conditions, diseases, or disorders that would benefit from modulation of somatostatin activity.

19 Claims, No Drawings

(56) References Cited

U.S. PATENT DOCUMENTS

| | | |
|---|---|---|
| 8,394,807 B2 | 3/2013 | Ghosh |
| 8,487,116 B2 | 7/2013 | Gomtsyan et al. |
| 8,530,499 B2 | 9/2013 | Cheruvallath et al. |
| 8,541,403 B2 | 9/2013 | Chu et al. |
| 8,604,032 B2 | 12/2013 | Ren et al. |
| 8,609,655 B2 | 12/2013 | Geibel et al. |
| 8,609,691 B2 | 12/2013 | Plettenburg et al. |
| 8,618,129 B2 | 12/2013 | Kuehnert et al. |
| 8,637,533 B2 | 1/2014 | Sadhu et al. |
| 8,642,774 B2 | 2/2014 | Grauert et al. |
| 8,685,962 B2 | 4/2014 | Gavish et al. |
| 8,686,002 B2 | 4/2014 | Amberg et al. |
| 8,772,047 B2 | 7/2014 | Thomas et al. |
| 8,802,840 B2 | 8/2014 | Francom et al. |
| 8,815,901 B2 | 8/2014 | Furet et al. |
| 8,962,342 B2 | 2/2015 | Thomas et al. |
| 8,962,810 B2 | 2/2015 | Zhan |
| 8,969,363 B2 | 3/2015 | Castro et al. |
| 9,120,749 B2 | 9/2015 | Matsuo et al. |
| 9,309,222 B2 | 4/2016 | Leonard et al. |
| 9,896,432 B2 | 2/2018 | Zhao et al. |
| 9,902,703 B2 | 2/2018 | Zhao et al. |
| 9,957,267 B2 | 5/2018 | Zhu et al. |
| 10,351,547 B2 | 7/2019 | Zhao et al. |
| 10,464,918 B2 | 11/2019 | Reddy et al. |
| 10,597,377 B2 | 3/2020 | Zhao et al. |
| 2003/0153553 A1 | 8/2003 | Mattei et al. |
| 2003/0158188 A1 | 8/2003 | Lee et al. |
| 2005/0009815 A1 | 1/2005 | Devita et al. |
| 2005/0033050 A1 | 2/2005 | Kruger et al. |
| 2005/0043239 A1 | 2/2005 | Douangpanya et al. |
| 2005/0054614 A1 | 3/2005 | Diacovo et al. |
| 2006/0079538 A1 | 4/2006 | Hallahan et al. |
| 2006/0106038 A1 | 5/2006 | Bouscary et al. |
| 2007/0010537 A1 | 1/2007 | Hamamura et al. |
| 2007/0135454 A1 | 6/2007 | Bayliss et al. |
| 2007/0203180 A1 | 8/2007 | Hoekstra et al. |
| 2008/0027044 A1 | 1/2008 | Lewis et al. |
| 2008/0027052 A1 | 1/2008 | Moe et al. |
| 2008/0287469 A1 | 11/2008 | Diacovo et al. |
| 2008/0299076 A1 | 12/2008 | Stockwell |
| 2008/0308770 A1 | 12/2008 | Tiwari |
| 2009/0209562 A1 | 8/2009 | Nagase et al. |
| 2009/0233947 A1 | 9/2009 | Bayliss et al. |
| 2009/0258853 A1 | 10/2009 | Eastman et al. |
| 2009/0298856 A1 | 12/2009 | Brown |
| 2010/0210682 A1 | 8/2010 | Faltynek et al. |
| 2010/0234324 A1 | 9/2010 | Eggenweiler et al. |
| 2010/0256120 A1 | 10/2010 | Brown et al. |
| 2010/0267767 A1 | 10/2010 | Narayanan et al. |
| 2011/0065671 A1 | 3/2011 | Harris et al. |
| 2011/0065676 A1 | 3/2011 | Perelman et al. |
| 2011/0071148 A1 | 3/2011 | Ding et al. |
| 2011/0130413 A1 | 6/2011 | Golding et al. |
| 2011/0152242 A1 | 6/2011 | Bayliss et al. |
| 2011/0294803 A1 | 12/2011 | Law et al. |
| 2012/0122889 A1 | 5/2012 | Yuan et al. |
| 2012/0232158 A1 | 9/2012 | Geibel et al. |
| 2012/0238582 A1 | 9/2012 | Eggenweiler et al. |
| 2013/0053365 A1 | 2/2013 | Wang et al. |
| 2013/0190309 A1 | 7/2013 | Vu |
| 2013/0289027 A1 | 10/2013 | De et al. |
| 2014/0024657 A1 | 1/2014 | Yuan et al. |
| 2014/0179718 A1 | 6/2014 | Evarts et al. |
| 2014/0243286 A1 | 8/2014 | Arnold et al. |
| 2014/0243322 A1 | 8/2014 | Arnold et al. |
| 2014/0275048 A1 | 9/2014 | Zeidan et al. |
| 2014/0302987 A1 | 10/2014 | Frackenpohl et al. |
| 2014/0371246 A1 | 12/2014 | Evarts et al. |
| 2015/0232478 A1 | 8/2015 | Ishida et al. |
| 2015/0239900 A1 | 8/2015 | Li et al. |
| 2015/0284337 A1 | 10/2015 | Aubele et al. |
| 2020/0190053 A1 | 6/2020 | Zhao et al. |

FOREIGN PATENT DOCUMENTS

| | | |
|---|---|---|
| JP | 2013091624 A | 5/2013 |
| KR | 20160062023 A | 6/2016 |
| WO | WO-9304047 A1 | 3/1993 |
| WO | WO-9322292 A1 | 11/1993 |
| WO | WO-9512583 A1 | 5/1995 |
| WO | WO-9710221 A1 | 3/1997 |
| WO | WO-9722594 A1 | 6/1997 |
| WO | WO-9811438 A1 | 3/1998 |
| WO | WO-9938850 A1 | 8/1999 |
| WO | WO-0055153 A1 | 9/2000 |
| WO | WO-0130768 A1 | 5/2001 |
| WO | WO-0181346 A2 | 11/2001 |
| WO | WO-03043995 A1 | 5/2003 |
| WO | WO-03045920 A1 | 6/2003 |
| WO | WO-03070701 A2 | 8/2003 |
| WO | WO-2004046107 A1 | 6/2004 |
| WO | WO-2004080463 A1 | 9/2004 |
| WO | WO-2005016348 A1 | 2/2005 |
| WO | WO-2005030729 A1 | 4/2005 |
| WO | WO-2005067901 A2 | 7/2005 |
| WO | WO-2005120511 A1 | 12/2005 |
| WO | WO-2006026597 A2 | 3/2006 |
| WO | WO-2006062981 A2 | 6/2006 |
| WO | WO-2006090272 A1 | 8/2006 |
| WO | WO-2006094237 A2 | 9/2006 |
| WO | WO-2006102610 A2 | 9/2006 |
| WO | WO-2006124490 A2 | 11/2006 |
| WO | WO-2007056167 A2 | 5/2007 |
| WO | WO-2007149031 A1 | 12/2007 |
| WO | WO-2008051272 A2 | 5/2008 |
| WO | WO-2008129276 A1 | 10/2008 |
| WO | WO-2009015179 A1 | 1/2009 |
| WO | WO-2009138788 A1 | 11/2009 |
| WO | WO-2010017055 A2 | 2/2010 |
| WO | WO-2010037129 A1 | 4/2010 |
| WO | WO-2010041054 A1 | 4/2010 |
| WO | WO-2010060937 A2 | 6/2010 |
| WO | WO-2010104882 A1 | 9/2010 |
| WO | WO-2010149786 A1 | 12/2010 |
| WO | WO-2011019651 A1 | 2/2011 |
| WO | WO-2012011591 A1 | 1/2012 |
| WO | WO-2012031383 A1 | 3/2012 |
| WO | WO-2012116237 A2 | 8/2012 |
| WO | WO-2012122370 A2 | 9/2012 |
| WO | WO-2012162254 A1 | 11/2012 |
| WO | WO-2012166151 A1 | 12/2012 |
| WO | WO-2013050996 A2 | 4/2013 |
| WO | WO-2013068470 A1 | 5/2013 |
| WO | WO-2014018891 A1 | 1/2014 |
| WO | WO-2014072930 A2 | 5/2014 |
| WO | WO-2014120764 A1 | 8/2014 |
| WO | WO-2016023885 A1 | 2/2016 |
| WO | WO-2016049568 A1 | 3/2016 |
| WO | WO-2017003723 A1 | 1/2017 |
| WO | WO-2017003724 A1 | 1/2017 |
| WO | WO-2018013676 A1 | 1/2018 |
| WO | WO-2019023278 A1 | 1/2019 |
| WO | WO-2019143718 A1 | 7/2019 |

OTHER PUBLICATIONS

Esch et al. Primary structure of ovine hypothalamic somatostatin-28 and somatostatin-25. PNAS USA 77:6827-6831 (1980).
Patel et al. Somatostatin receptors. Trends Endocrinol Metab 8:398-405 (1997).
PCT/US2018/043556 International Search Report and Written Opinion dated Nov. 7, 2018.
Pradayrol et al. N-terminally extended somatostatin: the primary structure of somatostatin-28. FEBS Letters 109:55-58 (1980).
Reisine et al. Molecular biology of somatostatin receptors. Endocr Rev 16:427-442 (1995).
Widder et al. Section III: Prodrugs Kinetics. Method in Enzymology. 112:309-396 (1985).
Wolkenberg et al. Design, synthesis, and evaluation of novel 3,6-diaryl-4-aminoalkoxyquinolines as selective agonists of somatostatin receptor subtype 2. J Med Chem 54:2351-2358 (2011).

(56) References Cited

OTHER PUBLICATIONS

Bundgaard. Design of Prodrugs. Elsevier (12 pgs.) (1985).
Cescato et al. Agonist-Biased Signaling at the sst2A Receptor: The Multi-Somatostatin Analogs KE108 and SOM230 Activate and Antagonize Distinct Signaling Pathways. Mol Endocrinol 24(1):240-249 (2010).
Dishington et al. Synthesis of a 5-alkoxypyrido[3,4-d]pyrimidin-4(3H)-one derivative via directed ortho-metallation of a pyridine analogue. Tetrahedron Lett 45:3733-3735 (2004).
Garrett et al. The Art of Meeting Palladium Specifications in Active Pharmaceutical Ingredients Produced by Pd-Catalyzed Reactions. Adv. Synth. Catal. 346:889-900 (2004).
Gradiz et al. MIA PaCa-2 and PANC-1—pancreas ductal adenocarcinoma cell lines with neuroendocrine differentiation and somatostatin receptors. Scientific Reports 6:21648 (15 pgs.) (2016).
Guideline on the Specification Limits for Residues of Metal Catalysts. European Medicines Agency. Pre-authorization Evaluation of Medicines for Human Use, London (Jan. 2007) (pp. 1-32).
Krupkova et al. Synthesis of quinazolines from N-(2-nitrophenylsulfonyl)iminodiacetate and alpha-(2-nitrophenylsulfonyl)amino ketones via 2H-indazole 1-oxides. J Org Chem 75(13):4562-4566 (2010).
Prasoon et al. Role of somatostatin and somatostatin receptor type 2 in postincisional nociception in rats. Neropeptides 49:47-54 (2015).
Science IP CAS Search, May 23, 2016 (291 pgs).
Silverman. The Organic Chemistry of Drug Design and Drug Action. Academic Press. pp. 352-355 (1992).
Song et al. Amine-Mediated Transimination and Aromatization-Triggered Domino Reaction in the Synthesis of Polyfunctionalized 4-Aminoquinolines. Org Lett 18(20):5328-5331 (2016).
Stahl et al. Handbook of Pharmaceutical Salts. Verlag Helvetica Chimica Acta, Zurich, 2002.
Stella. Prodrugs: Some Thoughts and Current Issues. J Pharm Sci 99(12):4755-4765 (2010).
Wolkenberg et al. Design, synthesis, and evaluation of novel 3,6-diaryl-4-aminoalkoxyquinolines as selective agonists of somatostatin receptor subtype 2. J Med Chem xxx:000 (8 pgs) (2010).

SOMATOSTATIN MODULATORS AND USES THEREOF

CROSS-REFERENCE

This application is filed pursuant to 35 U.S.C. 371 as a United States National Phase Application of International Application No. PCT/US2018/043556, filed Jul. 24, 2018, which claims the benefit of U.S. Provisional Patent Application No. 62/536,814 filed on Jul. 25, 2017, all of which is incorporated herein by reference in their entirety.

STATEMENT AS TO FEDERALLY SPONSORED RESEARCH

This invention was made with government support under grant numbers DK088501, NS092231, EY024185 awarded by the National Institutes of Health. The government has certain rights in the invention.

FIELD OF THE INVENTION

Described herein are compounds that are somatostatin modulators, methods of making such compounds, pharmaceutical compositions and medicaments comprising such compounds, and methods of using such compounds in the treatment of conditions, diseases, or disorders that would benefit from modulating somatostatin activity.

BACKGROUND OF THE INVENTION

Somatostatin is a peptide hormone that regulates the endocrine system and affects neurotransmission and cell proliferation via interaction with G-protein-coupled somatostatin receptors and inhibition of the release of numerous secondary hormones. Six subtype somatostatin receptor proteins have been identified (SSTR1, SSTR2a, SSTR2b, SSTR3, SSTR4, SSTR5) and are encoded by five different somatostatin receptor genes. Modulation of a particular subtype somatostatin receptor, or combination thereof, is attractive for the treatment of conditions, diseases, or disorders that would benefit from modulating somatostatin activity.

SUMMARY OF THE INVENTION

Compounds described herein are somatostatin modulator compounds. In some embodiments, compounds described herein modulate one or more of the subtype somatostatin receptor proteins. In some embodiments, compounds described herein modulate two or more of the subtype somatostatin receptor proteins. Somatostatin peptide analogs, such as octreotide and pasireotide, formulated as depot injections, are routinely used to normalize hormone levels for the treatment of GH secreting adenomas, pancreatic neuroendocrine tumors, and carcinoid tumors. Unfortunately, these analogs are only effective in about half of acromegalic patients with GH adenomas, and patients with carcinoid tumors frequently become resistant to therapy due to internalization and desensitization of the SST2A receptor. In addition, these peptide drugs are extremely expensive and require frequent doctor's office visits for painful injections that can lead to injection site reactions. Compounds described herein are molecules that are structurally different from peptide analogs. The compounds described herein are somatostatin modulators that are potent inhibitors of hormone secretion.

In one aspect, described herein is a compound of Formula (I), or a pharmaceutically acceptable salt, pharmaceutically acceptable solvate, diastereomeric mixture, enantiomer or prodrug thereof:

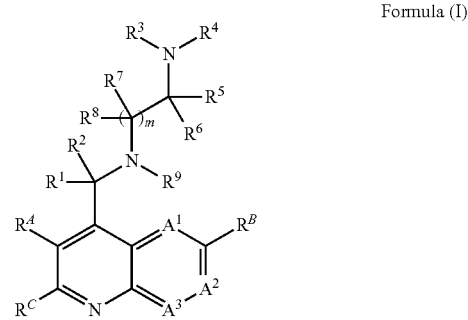

Formula (I)

wherein:
$R^1$ and $R^2$ are taken together with the carbon atom to which they are attached to form —C(=O)—;
or $R^1$ and $R^2$ are each independently selected from the group consisting of hydrogen, and unsubstituted or substituted $C_1$-$C_6$alkyl;
$R^A$ is hydrogen, halogen, unsubstituted or substituted $C_1$-$C_6$alkyl, unsubstituted or substituted $C_2$-$C_6$alkenyl, unsubstituted or substituted $C_2$-$C_6$alkynyl, unsubstituted or substituted $C_1$-$C_6$heteroalkyl, unsubstituted or substituted monocyclic carbocycle, unsubstituted or substituted bicyclic carbocycle, unsubstituted or substituted monocyclic heterocycle, or unsubstituted or substituted bicyclic heterocycle, wherein if $R^A$ is substituted then $R^A$ is substituted with 1-2 $R^{10}$ and 0-2 $R^{11}$;
$R^B$ is unsubstituted or substituted $C_1$-$C_6$alkyl, unsubstituted or substituted $C_2$-$C_6$alkenyl, unsubstituted or substituted $C_2$-$C_6$alkynyl, unsubstituted or substituted $C_1$-$C_6$heteroalkyl, unsubstituted or substituted monocyclic carbocycle, unsubstituted or substituted bicyclic carbocycle, unsubstituted or substituted monocyclic heterocycle, unsubstituted or substituted bicyclic heterocycle, wherein if $R^B$ is substituted then $R^B$ is substituted with 1-2 $R^{12}$ and 0-2 $R^{13}$;
$A^1$, $A^2$, and $A^3$ are independently $CR^C$ or N;
each $R^C$ is independently hydrogen, halogen, unsubstituted or substituted $C_1$-$C_4$alkyl, unsubstituted or substituted $C_1$-$C_4$fluoroalkyl, unsubstituted or substituted $C_1$-$C_4$alkoxy, unsubstituted or substituted $C_1$-$C_4$fluoroalkoxy, —CN, —OH, —CO$_2R^{14}$, —C(=O)NR$^{14}R^{15}$, —NR$^{14}R^{15}$, —NR$^{14}$C(=O)R$^{15}$, —SR$^{14}$, —S(=O)R$^{15}$, —SO$_2R^{15}$, or —SO$_2$NR$^{14}R^{15}$;
$R^3$ and $R^4$ are independently hydrogen, unsubstituted or substituted $C_1$-$C_6$ alkyl, unsubstituted or substituted $C_1$-$C_6$fluoroalkyl, or unsubstituted or substituted $C_3$-$C_6$cycloalkyl, wherein any substituted group of $R^3$ and $R^4$ is substituted with 1-4 $R^{16}$;
or $R^3$ and $R^4$ are taken together with the nitrogen atom to which they are attached to form an unsubstituted or substituted monocyclic or bicyclic heterocyclic ring, wherein if the heterocyclic ring is substituted then the heterocyclic ring is substituted with 1-4 $R^{16}$;
$R^5$, $R^6$, $R^7$, and $R^8$ are each independently selected from the group consisting of hydrogen, unsubstituted or substituted $C_1$-$C_6$ alkyl, and unsubstituted or substituted $C_1$-$C_6$fluoroalkyl, unsubstituted or substituted monocyclic carbocycle, unsubstituted or substituted monocyclic heterocycle, wherein any substituted group of $R^5$, $R^6$, $R^7$, and $R^8$ is substituted with 1-4 $R^{16}$;

$R^9$ is hydrogen, unsubstituted or substituted $C_1$-$C_6$ alkyl, unsubstituted or unsubstituted or substituted benzyl, wherein if $R^9$ is substituted then $R^9$ is substituted with 1-4 $R^{16}$;

or $R^4$ and any one of $R^5$, $R^7$, or $R^9$ are taken together with the intervening atoms to which they are attached to form an unsubstituted or substituted monocyclic 4- to 7-membered heterocyclic ring or an unsubstituted or substituted bicyclic 9- to 12-membered heterocyclic ring, wherein if the heterocyclic ring is substituted then the heterocyclic ring is substituted with 1-4 $R^{16}$;

or $R^5$ and any one of $R^6$, $R^7$ or $R^9$ are taken together with the intervening atoms to which they are attached to form an unsubstituted or substituted monocyclic 4- to 7-membered ring or a bicyclic 9- to 12-membered ring, wherein if the heterocyclic ring is substituted then the heterocyclic ring is substituted with 1-4 $R^{16}$;

or $R^7$ and $R^9$ are taken together with the intervening atoms to which they are attached to form an unsubstituted or substituted monocyclic 4- to 7-membered heterocyclic ring or an unsubstituted or substituted bicyclic 9- to 12-membered heterocyclic ring, wherein if the heterocyclic ring is substituted then the heterocyclic ring is substituted with 1-4 R16;

each $R^{10}$, $R^{11}$, $R^{12}$ and $R^{13}$ is independently hydrogen, halogen, unsubstituted or substituted $C_1$-$C_4$alkyl, unsubstituted or substituted $C_1$-$C_4$alkoxy, unsubstituted or substituted $C_1$-$C_4$fluoroalkyl, unsubstituted or substituted $C_1$-$C_4$fluoroalkoxy, unsubstituted or substituted monocyclic carbocycle, unsubstituted or substituted monocyclic heterocycle, —CN, —OH, —$CO_2R^{14}$, —$CH_2CO_2R^{14}$, —C(=O)$NR^{14}R^{15}$, —$CH_2C$(=O)$NR^{14}R^{15}$, —$NR^{14}R^{15}$, —$CH_2NR^{14}R^{15}$, —$NR^{14}C$(=O)$R^{15}$, —$CH_2NR^{14}C$(=O)$R^{15}$, —$SR^{14}$, —S(=O)$R^{15}$, —$SO_2R^{15}$, or —$SO_2NR^{14}R^{15}$, wherein if any group of $R^{10}$, $R^{11}$, $R^{12}$ and $R^{13}$ is substituted then the substituted group of $R^{10}$, $R^{11}$, $R^{12}$ and $R^{13}$ is substituted with 1-4 $R^{16}$;

each $R^{16}$ is independently halogen, $C_1$-$C_6$alkyl, heterocycle, —CN, —$OR^{14}$, —$CO_2R^{14}$, —C(=O)$NR^{14}R^{15}$, —$NR^{14}R^{15}$, —$NR^{14}C$(=O)$R^{15}$, —$SR^{14}$, —S(=O)$R^{15}$, —$SO_2R^{15}$, or —$SO_2NR^{14}R^{15}$;

each $R^{14}$ is independently selected from H, unsubstituted or substituted $C_1$-$C_6$alkyl, unsubstituted or substituted $C_1$-$C_6$heteroalkyl, substituted or unsubstituted unsubstituted or substituted $C_3$-$C_{10}$cycloalkyl, substituted or unsubstituted $C_2$-$C_{10}$heterocycloalkyl, substituted or unsubstituted aryl, and substituted or unsubstituted heteroaryl;

each $R^{15}$ is independently selected from H, unsubstituted or substituted $C_1$-$C_6$alkyl, unsubstituted or substituted $C_1$-$C_6$heteroalkyl, substituted or unsubstituted unsubstituted or substituted $C_3$-$C_{10}$cycloalkyl, substituted or unsubstituted $C_2$-$C_{10}$heterocycloalkyl, substituted or unsubstituted aryl, and substituted or unsubstituted heteroaryl; or $R^{14}$ and $R^{15}$ are taken together with the N atom to which they are attached to a substituted or unsubstituted N-containing heterocycle;

m is 1, 2, 3, or 4.

Also described herein is a pharmaceutical composition comprising a compound described herein, or a pharmaceutically acceptable salt, or solvate thereof, and at least one pharmaceutically acceptable excipient. In some embodiments, the pharmaceutical composition is formulated for administration to a mammal by intravenous administration, subcutaneous administration, oral administration, inhalation, nasal administration, dermal administration, or ophthalmic administration. In some embodiments, the pharmaceutical composition is formulated for administration to a mammal by oral administration. In some embodiments, the pharmaceutical composition is in the form of a tablet, a pill, a capsule, a liquid, a suspension, a gel, a dispersion, a solution, an emulsion, an ointment, or a lotion. In some embodiments, the pharmaceutical composition is in the form of a tablet, a pill, or a capsule.

Also described herein is a method of treating a disease or condition in a mammal that would benefit from the modulation of somatostatin receptor activity comprising administering a small molecule non-peptidyl compound, or pharmaceutically acceptable salt, or solvate thereof, to the mammal in need thereof. In some embodiments, the small molecule non-peptidyl compound is orally administered. In some embodiments, the small molecule non-peptidyl compound is a compound as described herein, or a pharmaceutically acceptable salt or solvate thereof. In some embodiments, the small molecule non-peptidyl compound is a SSTR2 modulator as described herein, or a pharmaceutically acceptable salt or solvate thereof. In some embodiments, the disease or condition is acromegaly, a neuroendocrine tumor, an ophthalmic disease or condition, neuropathy, nephropathy, a respiratory disease or condition, cancer, pain, a neurodegenerative disease or condition, an inflammatory disease or condition, a psychiatric disease or condition, or combinations thereof.

In any of the aforementioned aspects are further embodiments in which the effective amount of the compound of Formula (I), or a pharmaceutically acceptable salt thereof, is: (a) systemically administered to the mammal; and/or (b) administered orally to the mammal; and/or (c) intravenously administered to the mammal; and/or (d) administered by inhalation; and/or (e) administered by nasal administration; or and/or (f) administered by injection to the mammal; and/or (g) administered topically to the mammal; and/or (h) administered by ophthalmic administration; and/or (i) administered rectally to the mammal; and/or (j) adminstered non-systemically or locally to the mammal.

In any of the aforementioned aspects are further embodiments comprising single administrations of the effective amount of the compound, including further embodiments in which the compound is administered once a day to the mammal or the compound is administered to the mammal multiple times over the span of one day. In some embodiments, the compound is administered on a continuous dosing schedule. In some embodiments, the compound is administered on a continuous daily dosing schedule.

In any of the embodiments disclosed herein, the mammal is a human.

In some embodiments, compounds provided herein are orally administered to a human.

Articles of manufacture, which include packaging material, a compound of Formula (I), or a pharmaceutically acceptable salt thereof, within the packaging material, and a label that indicates that the compound or composition, or pharmaceutically acceptable salt, tautomers, pharmaceutically acceptable N-oxide, pharmaceutically active metabolite, pharmaceutically acceptable prodrug, or pharmaceutically acceptable solvate thereof, is used for modulating one or more subtype somatostatin receptor proteins, or for the treatment, prevention or amelioration of one or more symptoms of a disease or condition that would benefit from modulating one or more subtype somatostatin receptor proteins, are provided.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

Somatostatin (SST), also known as somatotropin release inhibiting factor (SRIF) was initially isolated as a 14-amino acid peptide from ovine hypothalamii (Brazeau et al., *Science* 179, 77-79, 1973). An N-terminal extended 28-amino acid peptide with similar biological activity to 14-amino acid somatostatin was subsequently isolated (Pradayrol et, al., *FEBS Letters,* 109, 55-58, 1980; Esch et al., *Proc. Natl. Acad. Sci. USA,* 77, 6827-6831, 1980). SST is a regulatory peptide produced by several cell types in response to other neuropeptides, neurotransmitters, hormones, cytokines, and growth factors. SST acts through both endocrine and paracrine pathways to affect its target cells. Many of these effects are related to the inhibition of secretion of other hormones, most notably growth hormone (GH). They are produced by a wide variety of cell types in the central nervous sstem (CNS) and gut and have multiple functions including modulation of secretion of growth hormone (GH), insulin, glucagon, as well as many other hormones that are anti-proliferative.

These pleotropic actions of somatostatins are mediated by six somatostatin receptor proteins (SSTR1, SSTR2a, SSTR2b, SSTR3, SSTR4, SSTR5). The six somatostatin receptor proteins are encoded by five different somatostatin receptor genes (Reisine and Bell, *Endocr Rev.* 16, 427-442, 1995; Patel and Srikant, *Trends Endocrinol Metab* 8, 398-405, 1997). All the receptors are members of the class-A subgroup of the GPCR superfamily. SST2A receptor is the most widely expressed subtype in human tumors and is the dominant receptor by which GH secretion is suppressed.

It is possible to selectively modulate any one of the somatostatin receptor subtypes, or combination thereof. In some embodiments, selectively modulating any one of the somatostatin receptor subtypes relative to the other somatostatin receptor subtypes, or combination thereof, in useful in a variety of clinical applications.

For example, modulation of SSTR2 activity mediates the inhibition of growth hormone (GH) release from the anterior pituitary and glucagon release from pancreas. SSTR2 is also implicated in many other biological functions such as, but not limited to, cell proliferation, nociception, inflammation, and angiogenesis. In some embodiments, a selective SSTR2 modulator is used in the treatment of acromegaly, gut neuroendocrine tumors, pain, neuropathies, nephropathies, and inflammation, as well as retinopathies resulting from aberrant blood vessel growth. In some other embodiments, a selective SSTR2 modulator is used in the treatment of arthritis, pain, cancer, inflammatory bowel disease, irritable bowel syndrome, Crohn's disease, Cushing's disease, acute lung injury, acute respiratory distress syndrome, and ophthalmic disorders such as age-related macular degeneration (AMD), diabetic retinopathy, diabetic macular edema, and Graves ophthalmology, among others.

In some embodiments, SSTR4 agonists exhibit anti-inflammatory and anti-nociceptive effects.

In some embodiments, SSTR3 agonists inhibit insulin secretion.

In some embodiments, SSTR5 agonists inhibit insulin secretion. In addition, SSTR5 has also been implicated to modulate the release of growth hormone.

Somatostatin peptide and its receptor subtypes are also widely expressed in the brain and disruption or diminishment of their activity is potentially involved in several psychiatric and neurodegenerative diseases. For example, concentrations of somatostatin in the cerebral cortex and hippocampus are reduced in schizophrenics and one of the most consistent neuropathologic findings in this patient group is a deficit in cortical inhibitory interneurons expressing somatostatin. Somatostatin is also highly expressed in brain regions associated with seizures and has also been implicated as having an important role in epilepsy. Somatostatin levels are diminished in the hippocampi of Alzheimer's and Parkinson's patients, suggesting that restoration of its signaling as a potential drug target for neurodegeneration.

In one aspect, compounds described herein are modulators of SSTR2. In some embodiments, compounds described herein selectively modulate the activity of SSTR2 relatve to the other somatostatin receptors.

In some embodiments, compounds described here are amenable to oral administration to a mammal in need of treatment with a somatastatin modulator.

In some embodiments, somatostatin receptor modulators described herein have utility over a wide range of therapeutic applications. In some embodiments, somatostatin receptor modulators described herein are used in the treatment of a variety of diseases or conditions such as, but not limited to acromegaly, neuroendocrine tumors, retinopathies and other ophthalmic disorders, neuropathy, nephropathy, respiratory diseases, cancers, pain, neurodegenerative diseases, inflammatory diseases, as well as psychiatric and neurodegenerative disorders. In some embodiments, somatostatin receptor modulators described herein are used in the treatment of acromegaly in a mammal.

In some embodiments, somatostatin receptor modulators described herein inhibit the secretion of various hormones and trophic factors in mammals. In some embodiments, the compounds are used to suppress certain endocrine secretions, such as, but not limited to GH, insulin, glucagon and prolactin. The suppression of certain endocrine secretions is useful in the treatment of disorders such as acromegaly; endocrine tumors such as carcinoids, VIPomas, insulinomas and glucagonomas; or diabetes and diabetes-related pathologies, including retinopathy, neuropathy and nephropathy. In some embodiments, somatostatin receptor modulators described herein are used to suppress exocrine secretions in the pancreas, stomach and intestines, for the treatment of disorders such as pancreatitis, fistulas, bleeding ulcers and diarrhea associated with such diseases as AIDS or cholera. Disorders involving autocrine or paracrine secretions of trophic factors such as IGF-1 (as well as some endocrine factors) which may be treated by administration of the compounds described herein include cancers of the breast, prostate, and lung (both small cell and non-small cell epidermoids), as well as hepatomas, neuroblastomas, colon and pancreatic adenocarcinomas (ductal type), chondrosarcomas, and melanomas, diabetic retinopathy, and atherosclerosis associated with vascular grafts and restenosis following angioplasty.

In some embodiments, somatostatin receptor modulators described herein are used to suppress the mediators of neurogenic inflammation (e.g. substance P or the tachykinins), and may be used in the treatment of rheumatoid arthritis; psoriasis; topical inflammation such as is associated with sunburn, eczema, or other sources of itching;

inflammatory bowel disease; irritable bowel syndrome; allergies, including asthma and other respiratory diseases In some other embodiments, the somatostatin receptor modulators described herein function as neuromodulators in the central nervous system and are useful in the treatment of Alzheimer's disease and other forms of dementia, pain, and headaches. In some embodiments, somatostatin receptor modulators described herein provide cytoprotection in disorders involving the splanchnic blood flow, including cirrhosis and oesophagal varices.

Compounds

Compounds of Formula (I), including pharmaceutically acceptable salts, prodrugs, active metabolites and pharmaceutically acceptable solvates thereof, are somatostatin receptor modulators. In some embodiments, the compounds of Formula (I), including pharmaceutically acceptable salts, prodrugs, active metabolites and pharmaceutically acceptable solvates thereof, are SSTR2 receptor modulators. In some embodiments, the somatostatin receptor modulators are somatostatin receptor agonists.

In one aspect, provided herein is a compound of Formula (I), or a pharmaceutically acceptable salt, pharmaceutically acceptable solvate, diastereomeric mixture, individual enantiomers or prodrug thereof:

Provided in one aspect is a compound that has the structure of Formula (I), or a pharmaceutically acceptable salt, solvate, diastereomeric mixture, individual enantiomers or prodrug thereof:

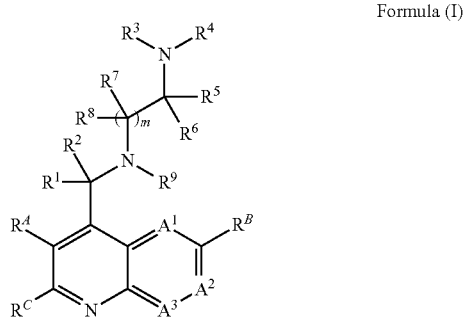

Formula (I)

wherein:

$R^1$ and $R^2$ are taken together with the carbon atom to which they are attached to form —C(=O)—;

or $R^1$ and $R^2$ are each independently selected from the group consisting of hydrogen, and unsubstituted or substituted $C_1$-$C_6$alkyl;

$R^A$ is hydrogen, halogen, unsubstituted or substituted $C_1$-$C_6$alkyl, unsubstituted or substituted $C_2$-$C_6$alkenyl, unsubstituted or substituted $C_2$-$C_6$alkynyl, unsubstituted or substituted $C_1$-$C_6$heteroalkyl, unsubstituted or substituted monocyclic carbocycle, unsubstituted or substituted bicyclic carbocycle, unsubstituted or substituted monocyclic heterocycle, or unsubstituted or substituted bicyclic heterocycle, wherein if $R^A$ is substituted then $R^A$ is substituted with 1-2 $R^{10}$ and 0-2 $R^{11}$;

$R^B$ is unsubstituted or substituted $C_1$-$C_6$alkyl, unsubstituted or substituted $C_2$-$C_6$alkenyl, unsubstituted or substituted $C_2$-$C_6$alkynyl, unsubstituted or substituted $C_1$-$C_6$heteroalkyl, unsubstituted or substituted monocyclic carbocycle, unsubstituted or substituted bicyclic carbocycle, unsubstituted or substituted monocyclic heterocycle, unsubstituted or substituted bicyclic heterocycle, wherein if $R^B$ is substituted then $R^B$ is substituted with 1-2 $R^{12}$ and 0-2 $R^{13}$;

$A^1$, $A^2$, and $A^3$ are independently $CR^C$ or N;

each $R^C$ is independently hydrogen, halogen, unsubstituted or substituted $C_1$-$C_4$alkyl, unsubstituted or substituted $C_1$-$C_4$fluoroalkyl, unsubstituted or substituted $C_1$-$C_4$alkoxy, unsubstituted or substituted $C_1$-$C_4$fluoroalkoxy, —CN, —OH, —CO$_2$R$^{14}$, —C(=O)NR$^{14}$R$^{15}$, —NR$^{14}$R$^{15}$, —NR$^{14}$C(=O)R$^{15}$, —SR$^{14}$, —S(=O)R$^{15}$, —SO$_2$R$^{15}$, or —SO$_2$NR$^{14}$R$^{15}$;

$R^3$ and $R^4$ are independently hydrogen, unsubstituted or substituted $C_1$-$C_6$ alkyl, unsubstituted or substituted $C_1$-$C_6$fluoroalkyl, or unsubstituted or substituted $C_3$-$C_6$cycloalkyl, wherein any substituted group of $R^3$ and $R^4$ is substituted with 1-4 $R^{16}$;

or $R^3$ and $R^4$ are taken together with the nitrogen atom to which they are attached to form an unsubstituted or substituted monocyclic or bicyclic heterocyclic ring, wherein if the heterocyclic ring is substituted then the heterocyclic ring is substituted with 1-4 $R^{16}$;

$R^5$, $R^6$, $R^7$, and $R^8$ are each independently selected from the group consisting of hydrogen, unsubstituted or substituted $C_1$-$C_6$ alkyl, and unsubstituted or substituted $C_1$-$C_6$fluoroalkyl, unsubstituted or substituted monocyclic carbocycle, unsubstituted or substituted monocyclic heterocycle, wherein any substituted group of $R^5$, $R^6$, $R^7$, and $R^8$ is substituted with 1-4 $R^{16}$;

$R^9$ is hydrogen, unsubstituted or substituted $C_1$-$C_6$ alkyl, unsubstituted or unsubstituted or substituted benzyl, wherein if $R^9$ is substituted then $R^9$ is substituted with 1-4 $R^{16}$;

or $R^4$ and any one of $R^5$, $R^7$, or $R^9$ are taken together with the intervening atoms to which they are attached to form an unsubstituted or substituted monocyclic 4- to 7-membered heterocyclic ring or an unsubstituted or substituted bicyclic 9- to 12-membered heterocyclic ring, wherein if the heterocyclic ring is substituted then the heterocyclic ring is substituted with 1-4 $R^{16}$;

or $R^5$ and any one of $R^6$, $R^7$ or $R^9$ are taken together with the intervening atoms to which they are attached to form an unsubstituted or substituted monocyclic 4- to 7-membered ring or a bicyclic 9- to 12-membered ring, wherein if the heterocyclic ring is substituted then the heterocyclic ring is substituted with 1-4 $R^{16}$;

or $R^7$ and $R^9$ are taken together with the intervening atoms to which they are attached to form an unsubstituted or substituted monocyclic 4- to 7-membered heterocyclic ring or an unsubstituted or substituted bicyclic 9- to 12-membered heterocyclic ring, wherein if the heterocyclic ring is substituted then the heterocyclic ring is substituted with 1-4 $R^{16}$;

each $R^{10}$, $R^{11}$, $R^{12}$ and $R^{13}$ is independently hydrogen, halogen, unsubstituted or substituted $C_1$-$C_4$alkyl, unsubstituted or substituted $C_2$-$C_4$alkenyl, unsubstituted or substituted $C_1$-$C_4$alkoxy, unsubstituted or substituted $C_1$-$C_4$fluoroalkyl, unsubstituted or substituted $C_1$-$C_4$fluoroalkoxy, unsubstituted or substituted monocyclic carbocycle, unsubstituted or substituted monocyclic heterocycle, —CN, —OH, —CO$_2$R$^{14}$, —CH$_2$CO$_2$R$^{14}$, —C(=O)NR$^{14}$R$^{15}$, —CH$_2$C(=O)NR$^{14}$R$^{15}$, —NR$^{14}$R$^{15}$, —CH$_2$NR$^{14}$R$^{15}$, —NR$^{14}$C(=O)R$^{15}$, —CH$_2$NR$^{14}$C(=O)R$^{15}$, —SR$^{14}$, —S(=O)R$^{15}$, —SO$_2$R$^{15}$, or —SO$_2$NR$^{14}$R$^{15}$, wherein if any group of $R^{10}$, $R^{11}$, $R^{12}$, and $R^{13}$ is substituted then the substituted group of $R^{10}$, $R^{11}$, $R^{12}$ and $R^{13}$ is substituted with 1-4 $R^{16}$;

each $R^{16}$ is independently halogen, $C_1$-$C_6$alkyl, heterocycle, —CN, —OR$^{14}$, —CO$_2$R$^{14}$, —C(=O)NR$^{14}$R$^{15}$, —NR$^{14}$R$^{15}$, —NR$^{14}$C(=O)R$^{15}$, —SR$^{14}$, —S(=O)R$^{15}$, —SO$_2$R$^{15}$, or —SO$_2$NR$^{14}$R$^{15}$;

each R$^{14}$ is independently selected from H, unsubstituted or substituted C$_1$-C$_6$alkyl, unsubstituted or substituted C$_1$-C$_6$heteroalkyl, substituted or unsubstituted unsubstituted or substituted C$_3$-C$_{10}$cycloalkyl, substituted or unsubstituted C$_2$-C$_{10}$heterocycloalkyl, substituted or unsubstituted aryl, and substituted or unsubstituted heteroaryl;

each R$^{15}$ is independently selected from H, unsubstituted or substituted C$_1$-C$_6$alkyl, unsubstituted or substituted C$_1$-C$_6$heteroalkyl, substituted or unsubstituted unsubstituted or substituted C$_3$-C$_{10}$cycloalkyl, substituted or unsubstituted C$_2$-C$_{10}$heterocycloalkyl, substituted or unsubstituted aryl, and substituted or unsubstituted heteroaryl; or R$^{14}$ and R$^{15}$ are taken together with the N atom to which they are attached to a substituted or unsubstituted N-containing heterocycle;

m is 1, 2, 3, or 4.

In some embodiments, a compound that has the structure of Formula (I), or a pharmaceutically acceptable salt, solvate, diastereomeric mixture, individual enantiomers or prodrug thereof:

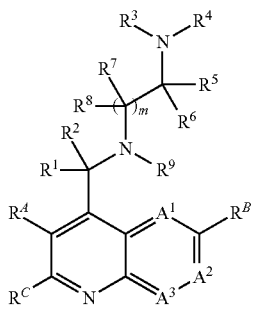

Formula (I)

wherein:

R$^1$ and R$^2$ are taken together with the carbon atom to which they are attached to form —C(=O)—;

or R$^1$ and R$^2$ are each independently selected from the group consisting of hydrogen, and unsubstituted or substituted C$_1$-C$_6$alkyl;

R$^A$ is hydrogen, halogen, unsubstituted or substituted C$_1$-C$_6$alkyl, unsubstituted or substituted C$_2$-C$_6$alkenyl, unsubstituted or substituted C$_2$-C$_6$alkynyl, unsubstituted or substituted C$_1$-C$_6$heteroalkyl, unsubstituted or substituted monocyclic carbocycle, unsubstituted or substituted bicyclic carbocycle, unsubstituted or substituted monocyclic heterocycle, or unsubstituted or substituted bicyclic heterocycle, wherein if R$^A$ is substituted then R$^A$ is substituted with 1-2 R$^{10}$ and 0-2 R$^{11}$;

R$^B$ is unsubstituted or substituted C$_1$-C$_6$alkyl, unsubstituted or substituted C$_2$-C$_6$alkenyl, unsubstituted or substituted C$_2$-C$_6$alkynyl, unsubstituted or substituted C$_1$-C$_6$heteroalkyl, unsubstituted or substituted monocyclic carbocycle, unsubstituted or substituted bicyclic carbocycle, unsubstituted or substituted monocyclic heterocycle, unsubstituted or substituted bicyclic heterocycle, wherein if R$^B$ is substituted then R$^B$ is substituted with 1-2 R$^{12}$ and 0-2 R$^{13}$;

A$^1$, A$^2$, and A$^3$ are independently CR$^C$ or N;

each R$^C$ is independently hydrogen, halogen, unsubstituted or substituted C$_1$-C$_4$alkyl, unsubstituted or substituted C$_1$-C$_4$fluoroalkyl, unsubstituted or substituted C$_1$-C$_4$alkoxy, unsubstituted or substituted C$_1$-C$_4$fluoroalkoxy, —CN, —OH, —CO$_2$R$^{14}$, —C(=O)NR$^{14}$R$^{15}$, —NR$^{14}$R$^{15}$, —NR$^{14}$C(=O)R$^{15}$, —SR$^{14}$, —S(=O)R$^{15}$, —SO$_2$R$^{15}$, or —SO$_2$NR$^{14}$R$^{15}$;

R$^3$ and R$^4$ are independently hydrogen, unsubstituted or substituted C$_1$-C$_6$ alkyl, unsubstituted or substituted C$_1$-C$_6$fluoroalkyl, or unsubstituted or substituted C$_3$-C$_6$cycloalkyl, wherein any substituted group of R$^3$ and R$^4$ is substituted with 1-4 R$^{16}$;

or R$^3$ and R$^4$ are taken together with the nitrogen atom to which they are attached to form an unsubstituted or substituted monocyclic or bicyclic heterocyclic ring, wherein if the heterocyclic ring is substituted then the heterocyclic ring is substituted with 1-4 R$^{16}$;

R$^5$, R$^6$, R$^7$, and R$^8$ are each independently selected from the group consisting of hydrogen, unsubstituted or substituted C$_1$-C$_6$ alkyl, and unsubstituted or substituted C$_1$-C$_6$fluoroalkyl, unsubstituted or substituted monocyclic carbocycle, unsubstituted or substituted monocyclic heterocycle, wherein any substituted group of R$^5$, R$^6$, R$^7$, and R$^8$ is substituted with 1-4 R$^{16}$;

R$^9$ is hydrogen, unsubstituted or substituted C$_1$-C$_6$ alkyl, unsubstituted or unsubstituted or substituted benzyl, wherein if R$^9$ is substituted then R$^9$ is substituted with 1-4 R$^{16}$;

or R$^4$ and any one of R$^5$, R$^7$, or R$^9$ are taken together with the intervening atoms to which they are attached to form an unsubstituted or substituted monocyclic 4- to 7-membered heterocyclic ring or an unsubstituted or substituted bicyclic 9- to 12-membered heterocyclic ring, wherein if the heterocyclic ring is substituted then the heterocyclic ring is substituted with 1-4 R$^{16}$;

or R$^5$ and any one of R$^6$, R$^7$ or R$^9$ are taken together with the intervening atoms to which they are attached to form an unsubstituted or substituted monocyclic 4- to 7-membered ring or a bicyclic 9- to 12-membered ring, wherein if the heterocyclic ring is substituted then the heterocyclic ring is substituted with 1-4 R$^{16}$;

or R$^7$ and R$^9$ are taken together with the intervening atoms to which they are attached to form an unsubstituted or substituted monocyclic 4- to 7-membered heterocyclic ring or an unsubstituted or substituted bicyclic 9- to 12-membered heterocyclic ring, wherein if the heterocyclic ring is substituted then the heterocyclic ring is substituted with 1-4 R$^{16}$;

each R$^{10}$, R$^{11}$, R$^{12}$, and R$^{13}$ is independently hydrogen, halogen, unsubstituted or substituted C$_1$-C$_4$alkyl, unsubstituted or substituted C$_1$-C$_4$alkoxy, unsubstituted or substituted C$_1$-C$_4$fluoroalkyl, unsubstituted or substituted C$_1$-C$_4$fluoroalkoxy, unsubstituted or substituted monocyclic carbocycle, unsubstituted or substituted monocyclic heterocycle, —CN, —OH, —CO$_2$R$^{14}$, —CH$_2$CO$_2$R$^{14}$, —C(=O)NR$^{14}$R$^{15}$, —CH$_2$C(=O)NR$^{14}$R$^{15}$, —NR$^{14}$R$^{15}$, —CH$_2$NR$^{14}$R$^{15}$, —NR$^{14}$C(=O)R$^{15}$, —CH$_2$NR$^{14}$C(=O)R$^{15}$, —SR$^{14}$, —S(=O)R$^{15}$, —SO$_2$R$^{15}$, or —SO$_2$NR$^{14}$R$^{15}$, wherein if any group of R$^{10}$, R$^{11}$, R$^{12}$ and R$^{13}$ is substituted then the substituted group of R$^{10}$, R$^{11}$, R$^{12}$, and R$^{13}$ is substituted with 1-4 R$^{16}$;

each R$^{16}$ is independently halogen, C$_1$-C$_6$alkyl, heterocycle, —CN, —OR$^{14}$, —CO$_2$R$^{14}$, —C(=O)NR$^{14}$R$^{15}$, —NR$^{14}$R$^{15}$, —NR$^{14}$C(=O)R$^{15}$, —SR$^{14}$, —S(=O)R$^{15}$, —SO$_2$R$^{15}$, or —SO$_2$NR$^{14}$R$^{15}$;

each R$^{14}$ is independently selected from H, unsubstituted or substituted C$_1$-C$_6$alkyl, unsubstituted or substituted C$_1$-C$_6$heteroalkyl, substituted or unsubstituted unsubstituted or substituted C$_3$-C$_{10}$cycloalkyl, substituted or unsubstituted C$_2$-C$_{10}$heterocycloalkyl, substituted or unsubstituted aryl, and substituted or unsubstituted heteroaryl;

each $R^{15}$ is independently selected from H, unsubstituted or substituted $C_1$-$C_6$alkyl, unsubstituted or substituted $C_1$-$C_6$heteroalkyl, substituted or unsubstituted unsubstituted or substituted $C_3$-$C_{10}$cycloalkyl, substituted or unsubstituted $C_2$-$C_{10}$heterocycloalkyl, substituted or unsubstituted aryl, and substituted or unsubstituted heteroaryl; or $R^{14}$ and $R^{15}$ are taken together with the N atom to which they are attached to a substituted or unsubstituted N-containing heterocycle;

m is 1, 2, 3, or 4.

For any and all of the embodiments, substituents are selected from among a subset of the listed alternatives. For example, in some embodiments, m is 1, 2, 3, or 4. In other embodiments, m is 1, 2, or 3. In some other embodiments, m is 1 or 2. In yet other embodiments, m is 1.

In some embodiments, $R^1$ and $R^2$ are hydrogen; or $R^1$ and $R^2$ are taken together with the carbon atom to which they are attached to form —C(=O)—; m is 1 or 2.

In some embodiments, $R^1$ and $R^2$ are taken together with the carbon atom to which they are attached to form —C(=O)—; m is 1 or 2.

In some embodiments, $R^1$ and $R^2$ are hydrogen; m is 1 or 2.

In some embodiments, $A^1$, $A^2$, and $A^3$ are $CR^C$.

In some embodiments, $A^1$ is N; and $A^2$ and $A^3$ are $CR^C$.

In some embodiments, $A^1$ and $A^3$ are $CR^C$; and $A^2$ is N.

In some embodiments, $A^1$ and $A^2$ are $CR^C$; and $A^3$ is N.

In some embodiments, $A^1$ and $A^2$ are N; and $A^3$ is $CR^C$.

In some embodiments, $A^1$ and $A^3$ are N; and $A^2$ is $CR^C$.

In some embodiments, $R^3$ and $R^4$ each independently selected from the group consisting of hydrogen, unsubstituted or substituted $C_1$-$C_6$ alkyl, and unsubstituted or substituted $C_1$-$C_6$fluoroalkyl, wherein any substituted group of $R^3$ and $R^4$ is substituted with 1-4 $R^{16}$.

In some embodiments, $R^3$ is hydrogen; $R^6$ is hydrogen; and $R^8$ is hydrogen.

In some embodiments,

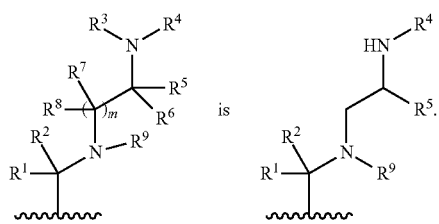

In some embodiments,

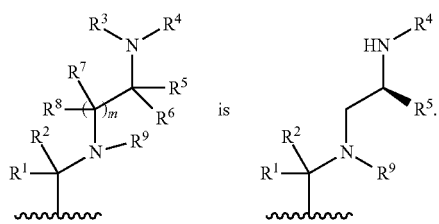

In some embodiments,

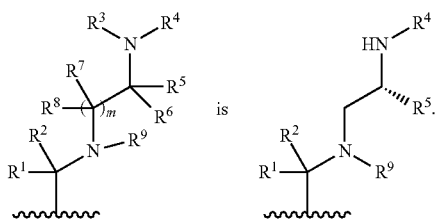

In some embodiments, $R^1$ and $R^2$ are taken together with the carbon atom to which they are attached to form a —C(=O)—.

In some embodiments, the compound of Formula (I) has the structure of Formula (Ia), or a pharmaceutically acceptable salt, solvate, diastereomeric mixture, individual enantiomers or prodrug thereof:

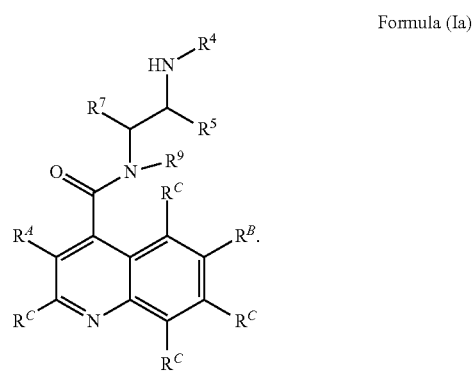

Formula (Ia)

In some embodiments, the compound of Formula (I) has the structure of Formula (Ib), or a pharmaceutically acceptable salt, solvate, diastereomeric mixture, individual enantiomers or prodrug thereof:

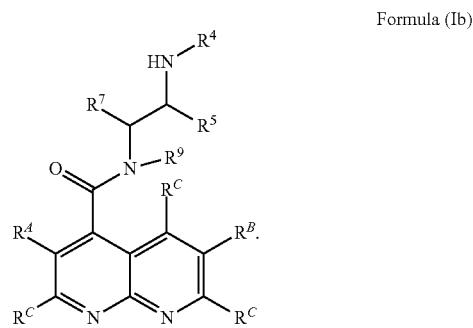

Formula (Ib)

In some embodiments, the compound of Formula (I) has the structure of Formula (Ic), or a pharmaceutically accept able salt, solvate, diastereomeric mixture, individual enantiomers or prodrug thereof:

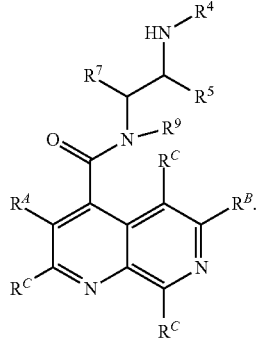

Formula (Ic)

In some embodiments, the compound of Formula (I) has the structure of Formula (Id), or a pharmaceutically acceptable salt, solvate, diastereomeric mixture, individual enantiomers or prodrug thereof:

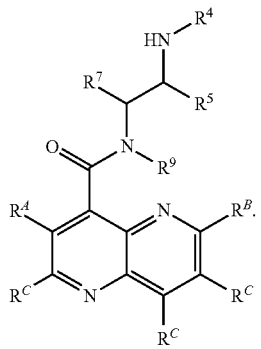

Formula (Id)

In some embodiments, the compound of Formula (I) has the structure of Formula (Ie), or a pharmaceutically acceptable salt, solvate, diastereomeric mixture, individual enantiomers or prodrug thereof:

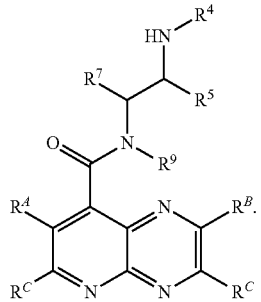

Formula (Ie)

In some embodiments, the compound of Formula (I) has the structure of Formula (If), or a pharmaceutically acceptable salt, solvate, diastereomeric mixture, individual enantiomers or prodrug thereof:

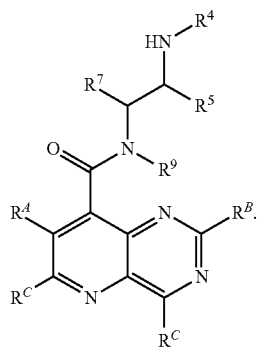

Formula (If)

In some embodiments, $R^{10}$ and $R^{11}$ are hydrogen.

In some embodiments, the compound of Formula (I) has the structure of Formula (Ig), or a pharmaceutically acceptable salt, solvate, diastereomeric mixture, individual enantiomers or prodrug thereof:

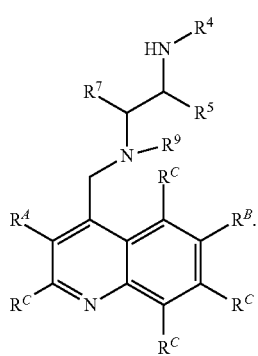

Formula (Ig)

In some embodiments, the compound of Formula (I) has the structure of Formula (Ih), or a pharmaceutically acceptable salt, solvate, diastereomeric mixture, individual enantiomers or prodrug thereof:

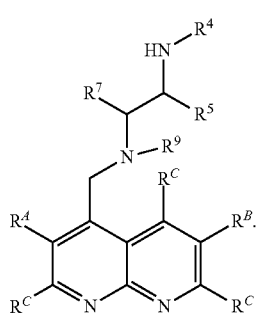

Formula (Ih)

In some embodiments, the compound of Formula (I) has the structure of Formula (Ii), or a pharmaceutically accept able salt, solvate, diastereomeric mixture, individual enantiomers or prodrug thereof:

Formula (Ii)

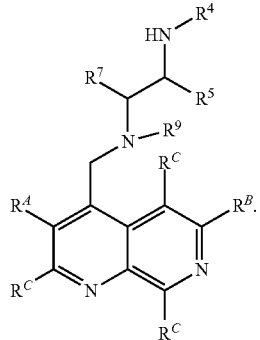

In some embodiments, the compound of Formula (I) has the structure of Formula (Ij), or a pharmaceutically acceptable salt, solvate, diastereomeric mixture, individual enantiomers or prodrug thereof:

Formula (Ij)

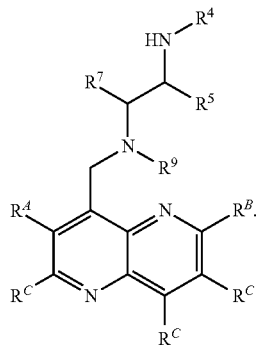

In some embodiments, the compound of Formula (I) has the structure of Formula (Ik), or a pharmaceutically acceptable salt, solvate, diastereomeric mixture, individual enantiomers or prodrug thereof:

Formula (Ik)

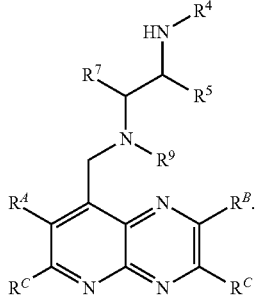

In some embodiments, the compound of Formula (I) has the structure of Formula (Il), or a pharmaceutically acceptable salt, solvate, diastereomeric mixture, individual enantiomers or prodrug thereof:

Formula (Il)

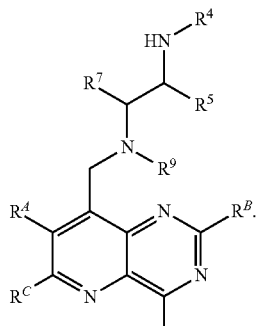

In some embodiments, each $R^C$ is independently hydrogen, F, Cl, Br, methyl, ethyl, n-propyl, i-propyl, n-butyl, i-butyl, sec-butyl, tert-butyl, monofluoromethyl, difluoromethyl, trifluoromethyl, methoxy, ethoxy, trifluormethoxy, —CN, —OH, —CO$_2$R$^{14}$, —C(=O)NR$^{14}$R$^{15}$, —C(=NOR$^{14}$)R$^{15}$, —SR$^{14}$, —S(=O)(C$_1$-C$_4$alkyl), —SO$_2$(C$_1$-C$_4$alkyl), or —SO$_2$NR$^{14}$R$^{15}$.

In some embodiments, each $R^C$ is independently hydrogen, F, Cl, Br, methyl, ethyl, n-propyl, i-propyl, n-butyl, i-butyl, sec-butyl, tert-butyl, monofluoromethyl, difluoromethyl, trifluoromethyl, methoxy, ethoxy, trifluormethoxy, —CN, or —OH.

In some embodiments, $R^4$ is hydrogen, halogen, unsubstituted or substituted C$_1$-C$_6$alkyl, unsubstituted or substituted C$_2$-C$_6$alkenyl, unsubstituted or substituted C$_2$-C$_6$alkynyl, or unsubstituted or substituted C$_1$-C$_6$heteroalkyl, wherein if $R^4$ is substituted then $R^4$ is substituted with 1-2 $R^{10}$ and 0-2 $R^{11}$.

In some embodiments, $R^4$ is a cyclic ring that is an unsubstituted or substituted monocyclic carbocycle, unsubstituted or substituted bicyclic carbocycle, unsubstituted or substituted monocyclic heterocycle, or unsubstituted or substituted bicyclic heterocycle, wherein if $R^4$ is substituted then $R^4$ is substituted with 1-2 $R^{10}$ and 0-2 $R^{11}$.

In some embodiments, $R^4$ is a cyclic ring that is an unsubstituted or substituted monocyclic carbocycle, or unsubstituted or substituted monocyclic heterocycle, wherein if $R^4$ is substituted then $R^4$ is substituted with 1-2 $R^{10}$ and 0-2 $R^{11}$.

In some embodiments, $R^4$ is a cyclic ring that is an unsubstituted or substituted monocyclic carbocycle, or unsubstituted or substituted monocyclic heterocycle, wherein if $R^4$ is substituted then $R^4$ is substituted with $R^{10}$ and $R^{11}$, wherein $R^{10}$ and $R^{11}$ are in an ortho-relationship on $R^4$. In some embodiments, $R^4$ is a cyclic ring that is an unsubstituted or substituted monocyclic carbocycle, or unsubstituted or substituted monocyclic heterocycle, wherein if $R^4$ is substituted then $R^4$ is substituted with $R^{10}$ and $R^{11}$, wherein $R^{10}$ and $R^{11}$ are in a meta-relationship on $R^4$. In some embodiments, $R^4$ is a cyclic ring that is an unsubstituted or substituted monocyclic carbocycle, or unsubstituted or substituted monocyclic heterocycle, wherein if $R^4$ is substituted then $R^4$ is substituted with $R^{10}$ and $R^{11}$, wherein $R^{10}$ and $R^{11}$ are in a para-relationship on $R^4$.

In some embodiments, $R^4$ is an unsubstituted or substituted monocyclic carbocycle, wherein if $R^4$ is substituted then $R^4$ is substituted with $R^{10}$ and $R^{11}$, wherein $R^{10}$ and $R^{11}$ are in a meta-relationship on $R^4$. In some embodiments, $R^4$ is an unsubstituted or substituted monocyclic heterocycle, wherein if $R^A$ is substituted then $R^A$ is substituted with $R^{10}$ and $R^{11}$, wherein $R^{10}$ and $R^{11}$ are in a meta-relationship on $R^A$.

In some embodiments, $R^A$ is an unsubstituted or substituted monocyclic carbocycle, or unsubstituted or substituted bicyclic carbocycle, wherein if $R^A$ is substituted then $R^A$ is substituted with 1-2 $R^{10}$ and 0-2 $R^{11}$.

In some embodiments, $R^A$ is an unsubstituted or substituted monocyclic carbocycle selected from unsubstituted or substituted phenyl, unsubstituted or substituted cyclopropyl, unsubstituted or substituted cyclobutyl, unsubstituted or substituted cyclopentyl, unsubstituted or substituted cyclopentenyl, unsubstituted or substituted cyclohexyl or unsubstituted or substituted cyclohexenyl, wherein if $R^A$ is substituted then $R^A$ is substituted with 1-2 $R^{10}$ and 0-2 $R^{11}$.

In some embodiments, $R^A$ is an unsubstituted or substituted phenyl, wherein if $R^A$ is substituted then $R^A$ is substituted with 1-2 $R^{10}$ and 0-2 $R^{11}$.

In some embodiments, $R^A$ is

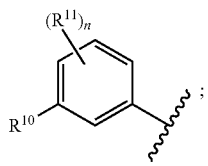

n is 0, 1, or 2.

In some embodiments, $R^A$ is

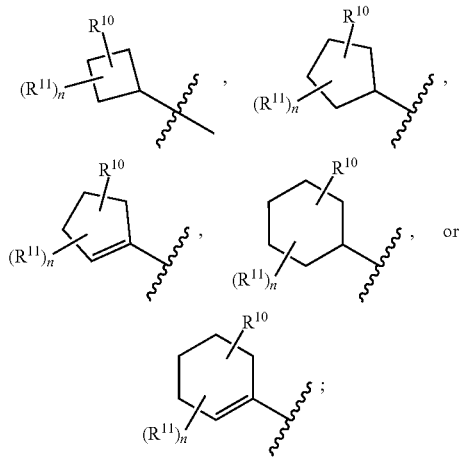

n is 0, 1, or 2.

In some embodiments, $R^A$ is an unsubstituted or substituted bicyclic carbocycle selected from unsubstituted or substituted naphthyl, unsubstituted or substituted indanyl, unsubstituted or substituted indenyl, or unsubstituted or substituted tetrahyodronaphthyl, wherein if $R^A$ is substituted then $R^A$ is substituted with 1-2 $R^{10}$ and 0-2 $R^{11}$.

In some embodiments, $R^A$ is an unsubstituted or substituted monocyclic heterocycle containing 1-4 N atoms and 0 or 1 O or S atom, unsubstituted or substituted monocyclic heterocycle containing 0-4 N atoms and 1 O or S atoms, unsubstituted or substituted bicyclic heterocycle containing 1-4 N atoms and 0 or 1 O or S atoms, or unsubstituted or substituted bicyclic heterocycle containing 0-4 N atoms and 1 O or S atoms, wherein if $R^A$ is substituted then $R^A$ is substituted with 1-2 $R^{10}$ and 0-2 $R^{11}$.

In some embodiments, $R^A$ is an unsubstituted or substituted monocyclic heterocycle selected from unsubstituted or substituted furanyl, unsubstituted or substituted pyrrolyl, unsubstituted or substituted oxazolyl, unsubstituted or substituted thiazolyl, unsubstituted or substituted imidazolyl, unsubstituted or substituted pyrazolyl, unsubstituted or substituted triazolyl, unsubstituted or substituted tetrazolyl, unsubstituted or substituted isoxazolyl, unsubstituted or substituted isothiazolyl, unsubstituted or substituted oxadiazolyl, unsubstituted or substituted thiadiazolyl, unsubstituted or substituted pyridinyl, unsubstituted or substituted pyrimidinyl, unsubstituted or substituted pyrazinyl, unsubstituted or substituted pyridazinyl, and unsubstituted or substituted triazinyl, wherein if $R^A$ is substituted then $R^A$ is substituted with 1-2 $R^{10}$ and 0-2 $R^{11}$.

In some embodiments, $R^A$ is

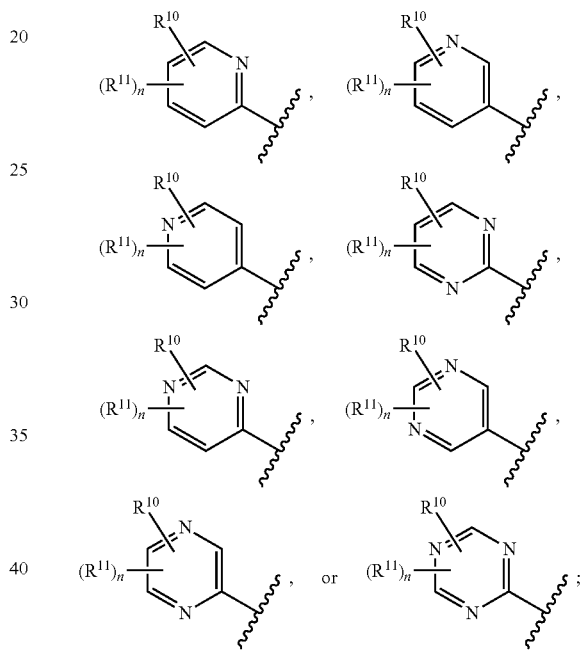

n is 0, 1, or 2

In some embodiments, $R^A$ is

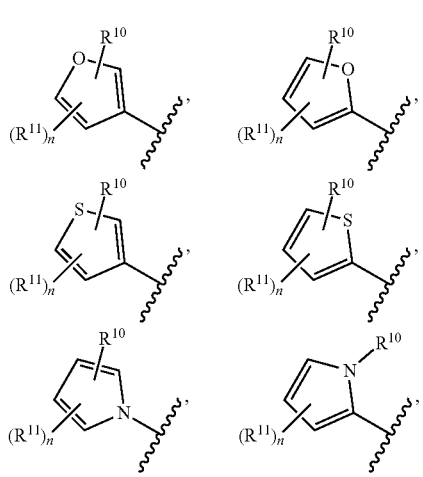

-continued

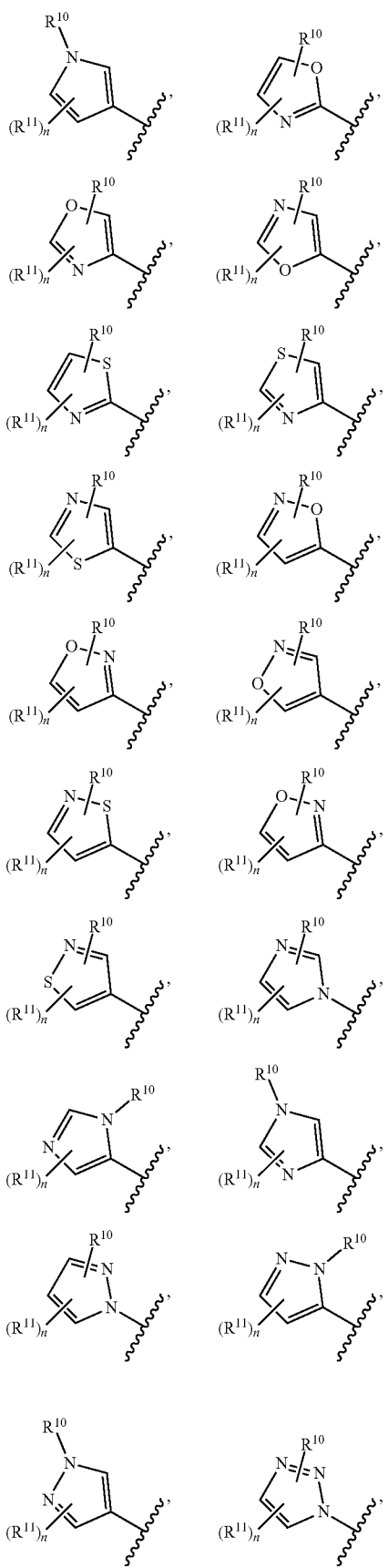

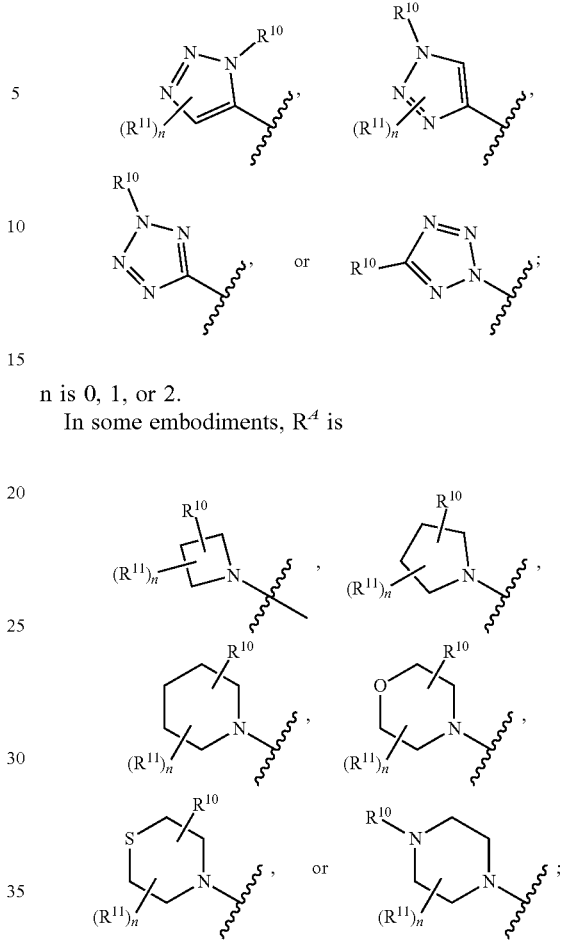

n is 0, 1, or 2.

In some embodiments, $R^A$ is n is 0, 1, or 2.

In some embodiments, $R^A$ is an unsubstituted or substituted bicyclic heterocycle selected from unsubstituted or substituted quinolinyl, unsubstituted or substituted isoquinolinyl, unsubstituted or substituted quinazolinyl, unsubstituted or substituted quinoxalinyl, unsubstituted or substituted naphthyridinyl, unsubstituted or substituted indolyl, unsubstituted or substituted indazolyl, unsubstituted or substituted benzoxazolyl, unsubstituted or substituted benzisoxazolyl, unsubstituted or substituted benzofuranyl, unsubstituted or substituted benzothienyl, unsubstituted or substituted benzothiazolyl, unsubstituted or substituted benzimidazolyl, unsubstituted or substituted purinyl, unsubstituted or substituted cinnolinyl, unsubstituted or substituted phthalazinyl, unsubstituted or substituted pteridinyl, unsubstituted or substituted pyridopyrimidinyl, unsubstituted or substituted pyrazolopyrimidinyl, unsubstituted or substituted azaindolyl, unsubstituted or substituted indolinyl, unsubstituted or substituted isoindolinyl, unsubstituted or substituted indolinonyl, unsubstituted or substituted isoindolinonyl, or unsubstituted or substituted quinolinonyl, wherein if $R^A$ is substituted then $R^A$ is substituted with 1-2 $R^{10}$ and 0-2 $R^{11}$.

In some embodiments, each $R^{10}$ is independently hydrogen, halogen, unsubstituted or substituted $C_1$-$C_4$alkyl, unsubstituted or substituted $C_1$-$C_4$alkoxy, unsubstituted or substituted $C_1$-$C_4$fluoroalkyl, unsubstituted or substituted $C_1$-$C_4$fluoroalkoxy, unsubstituted or substituted monocyclic carbocycle, unsubstituted or substituted monocyclic heterocycle, —CN, —OH, —CO$_2$R$^{14}$, —CH$_2$CO$_2$R$^{14}$, —C(═O)NR$^{14}$R$^{15}$, —CH$_2$C(═O)NR$^{14}$R$^{15}$, NR$^{14}$R$^{15}$, CH$_2$NR$^{14}$R$^{15}$, —NR$^{14}$C(═O)R$^{15}$, —CH$_2$NR$^{14}$C(═O)R$^{15}$, —SR$^{14}$, —S(═O)R$^{15}$, —SO$_2$R$^{15}$, or —SO$_2$NR$^{14}$R$^{15}$, wherein if R$^{10}$ is substituted then R$^{10}$ is substituted with 1-4 R$^{16}$; each R$^{11}$ is independently hydrogen, halogen, unsubstituted or substituted C$_1$-C$_4$alkyl, unsubstituted or substituted C$_1$-C$_4$alkoxy, unsubstituted or substituted C$_1$-C$_4$fluoroalkyl, unsubstituted or substituted C$_1$-C$_4$fluoroalkoxy, —CN, or —OH, wherein if R$^{11}$ is substituted then R$^{11}$ is substituted with 1-4 R$^{16}$.

In some embodiments, each R$^{10}$ is independently hydrogen, halogen, unsubstituted or substituted C$_1$-C$_4$alkyl, unsubstituted or substituted C$_1$-C$_4$alkoxy, C$_1$-C$_4$fluoroalkyl, C$_1$-C$_4$fluoroalkoxy, unsubstituted or substituted phenyl, unsubstituted or substituted monocyclic heterocycle, —CN, —OH, —CO$_2$R$^{14}$, —CH$_2$CO$_2$R$^{14}$, —C(═O)NR$^{14}$R$^{15}$, —CH$_2$C(═O)NR$^{14}$R$^{15}$, —NR$^{14}$R$^{15}$, —CH$_2$NR$^{14}$R$^{15}$, —NR$^{14}$C(═O)R$^{15}$, or —CH$_2$NR$^{14}$C(═O)R$^{15}$, wherein if R$^{10}$ is substituted then R$^{10}$ is substituted with 1-4 R$^{16}$; and each R$^{11}$ is independently hydrogen, halogen, unsubstituted or substituted C$_1$-C$_4$alkyl, C$_1$-C$_4$fluoroalkyl, C$_1$-C$_4$alkoxy, C$_1$-C$_4$fluoroalkoxy, or —CN, wherein if R$^{11}$ is substituted then R$^{11}$ is substituted with —OR$^{14}$ or —NR$^{14}$R$^{15}$.

In some embodiments, each Rth is independently hydrogen, F, Cl, —CH$_3$, —OCH$_3$, —CF$_3$, —OCF$_3$, —CN, —OH, —CO$_2$H, —CH$_2$CO$_2$H, —C(═O)NH$_2$, —CH$_2$C(═O)NH$_2$, —NH$_2$, —CH$_2$NH$_2$, —NHC(═O)CH$_3$, or —CH$_2$NHC(═O)CH$_3$; and each R$^{11}$ is independently hydrogen, F, Cl, —CH$_3$, —OCH$_3$, —CF$_3$, —OCF$_3$, or —CN.

In some embodiments, R$^B$ is a cyclic ring that is an unsubstituted or substituted monocyclic carbocycle, unsubstituted or substituted bicyclic carbocycle, unsubstituted or substituted monocyclic heterocycle, unsubstituted or substituted bicyclic heterocycle, wherein if R$^B$ is substituted then R$^B$ is substituted with 1-2 R$^{12}$ and 0-2 R$^{13}$.

In some embodiments, R$^B$ is a cyclic ring that is an unsubstituted or substituted monocyclic carbocycle, or unsubstituted or substituted monocyclic heterocycle, wherein if R$^B$ is substituted then R$^B$ is substituted with 1-2 R$^{12}$ and 0-2 R$^{13}$.

In some embodiments, R$^B$ is a cyclic ring that is an unsubstituted or substituted monocyclic carbocycle, or unsubstituted or substituted monocyclic heterocycle, wherein if R$^B$ is substituted then R$^B$ is substituted with R$^{12}$ and R$^{13}$, wherein R$^{12}$ and R$^{13}$ are in an ortho relationship on R$^B$. In some embodiments, R$^B$ is a cyclic ring that is an unsubstituted or substituted monocyclic carbocycle, or unsubstituted or substituted monocyclic heterocycle, wherein if R$^B$ is substituted then R$^B$ is substituted with R$^{12}$ and R$^{13}$, wherein R$^{12}$ and R$^{13}$ are in a meta-relationship on R$^B$. In some embodiments, R$^B$ is a cyclic ring that is an unsubstituted or substituted monocyclic carbocycle, or unsubstituted or substituted monocyclic heterocycle, wherein if R$^B$ is substituted then R$^B$ is substituted with R$^{12}$ and R$^{13}$, wherein R$^{12}$ and R$^{13}$ are in a para-relationship on R$^B$.

In some embodiments, R$^B$ is an unsubstituted or substituted monocyclic carbocycle, wherein if R$^B$ is substituted then R$^B$ is substituted with R$^{12}$ and R$^{13}$, wherein R$^{12}$ and R$^{13}$ are in a meta-relationship on R$^B$. In some embodiments, R$^B$ is an unsubstituted or substituted monocyclic heterocycle, wherein if R$^B$ is substituted then R$^B$ is substituted with R$^{12}$ and R$^{13}$, wherein R$^{12}$ and R$^{13}$ are in a meta-relationship on R$^B$.

In some embodiments, R$^B$ is an unsubstituted or substituted monocyclic carbocycle, or unsubstituted or substituted bicyclic carbocycle, wherein if R$^B$ is substituted then R$^B$ is substituted with 1-2 R$^{12}$ and 0-2 R$^{13}$.

In some embodiments, R$^B$ is an unsubstituted or substituted monocyclic carbocycle selected from unsubstituted or substituted phenyl, unsubstituted or substituted cyclopropyl, unsubstituted or substituted cyclobutyl, unsubstituted or substituted cyclopentyl, unsubstituted or substituted cyclopentenyl, unsubstituted or substituted cyclohexyl, or unsubstituted or substituted cyclohexenyl, wherein if R$^B$ is substituted then R$^B$ is substituted with 1-2 R$^{12}$ and 0-2 R$^{13}$.

In some embodiments, R$^B$ is an unsubstituted or substituted phenyl, wherein if R$^B$ is substituted then R$^B$ is substituted with 1-2 R$^{12}$ and 0-2 R$^{13}$.

In some embodiments, R$^B$ is

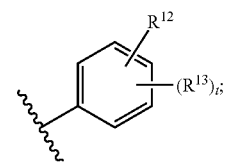

t is 0, 1, or 2.

In some embodiments, R$^B$ is

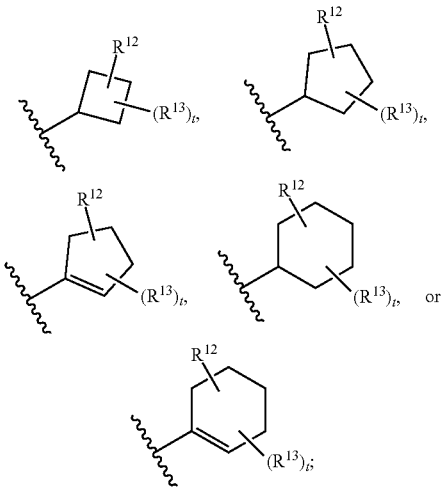

t is 0, 1, or 2.

In some embodiments, R$^B$ is an unsubstituted or substituted bicyclic carbocycle selected from unsubstituted or substituted naphthyl, unsubstituted or substituted indanyl, unsubstituted or substituted indenyl, or unsubstituted or substituted tetrahyodronaphthyl, wherein if R$^B$ is substituted then R$^B$ is substituted with 1-2 R$^{12}$ and 0-2 R$^{13}$.

In some embodiments, R$^B$ is an unsubstituted or substituted monocyclic heterocycle containing 1-4 N atoms and 0 or 1 O or S atom, unsubstituted or substituted monocyclic heterocycle containing 0-4 N atoms and 1 O or S atoms, unsubstituted or substituted bicyclic heterocycle containing 1-4 N atoms and 0 or 1 O or S atoms, or unsubstituted or substituted bicyclic heterocycle containing 0-4 N atoms and 1 O or S atoms, wherein if R$^B$ is substituted then R$^B$ is substituted with 1-2 R$^{12}$ and 0-2 R$^{13}$.

In some embodiments, R$^B$ is an unsubstituted or substituted monocyclic heterocycle selected from unsubstituted or substituted furanyl, unsubstituted or substituted pyrrolyl, unsubstituted or substituted oxazolyl, unsubstituted or substituted thiazolyl, unsubstituted or substituted imidazolyl, unsubstituted or substituted pyrazolyl, unsubstituted or substituted triazolyl, unsubstituted or substituted tetrazolyl, unsubstituted or substituted isoxazolyl, unsubstituted or substituted isothiazolyl, unsubstituted or substituted oxadiazolyl, unsubstituted or substituted thiadiazolyl, unsubstituted or substituted pyridinyl, unsubstituted or substituted pyrimidinyl, unsubstituted or substituted pyrazinyl, unsubstituted or substituted pyridazinyl, and unsubstituted or substituted triazinyl, wherein if $R^B$ is substituted then $R^B$ is substituted with 1-2 $R^{12}$ and 0-2 $R^{13}$.

In some embodiments, $R^B$ is

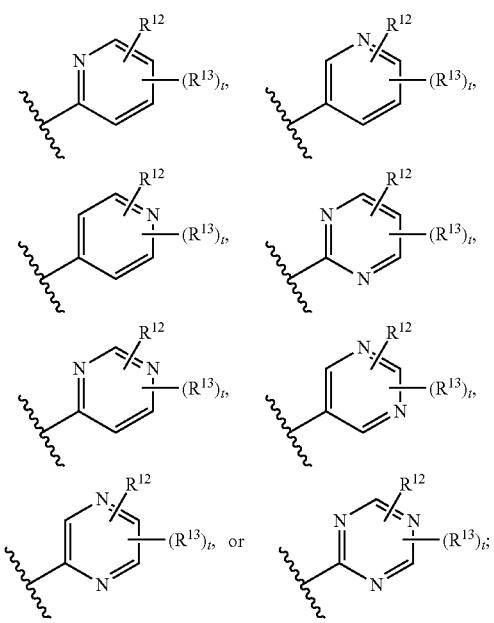

t is 0, 1, or 2

In some embodiments, $R^B$ is

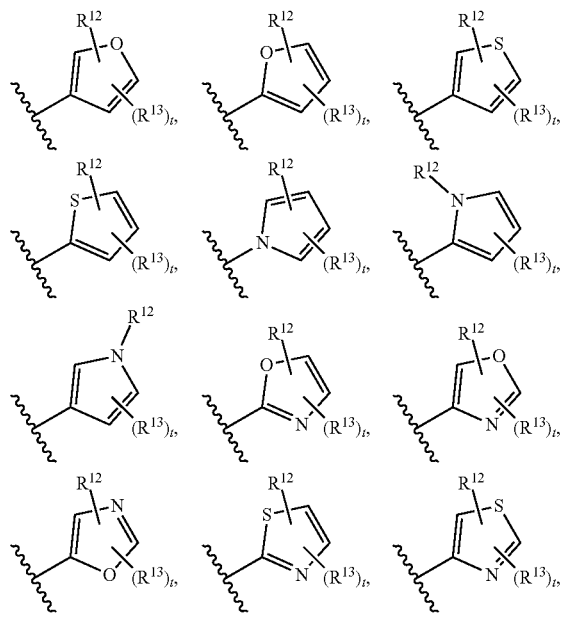

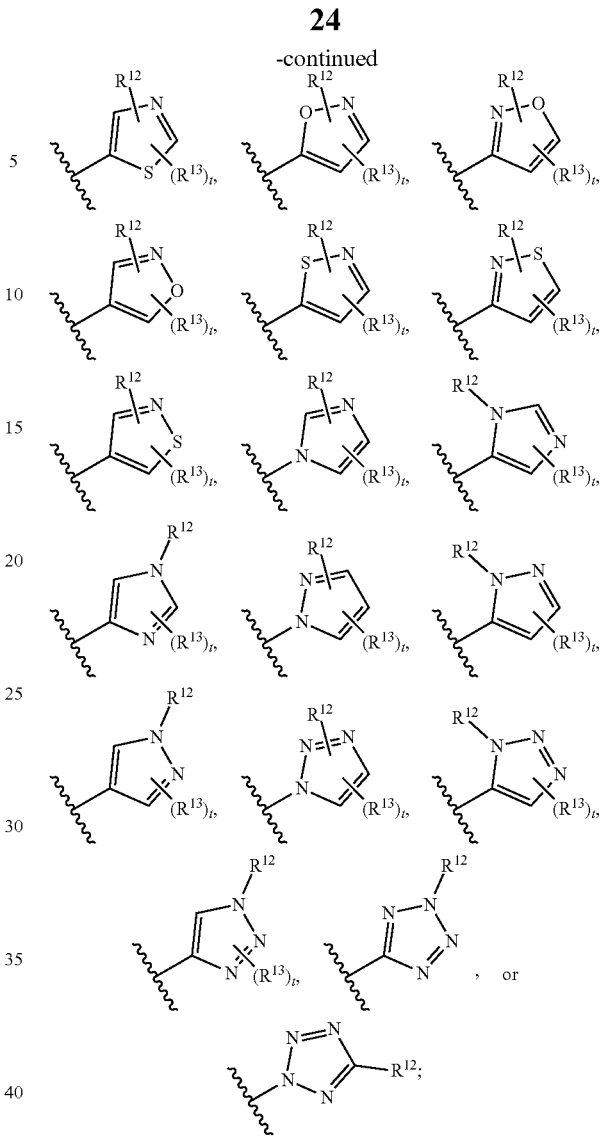

t is 0, 1, or 2.

In some embodiments, $R^B$ is

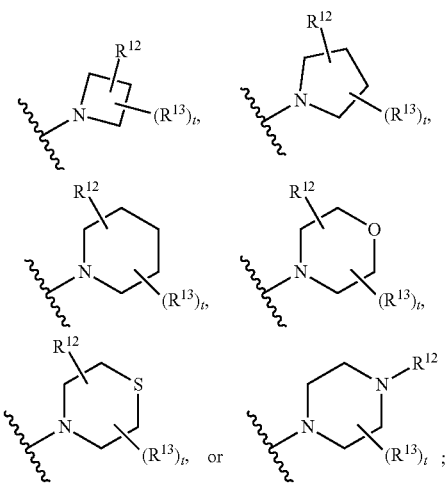

t is 0, 1, or 2.

In some embodiments, $R^B$ is an unsubstituted or substituted bicyclic heterocycle selected from unsubstituted or substituted quinolinyl, unsubstituted or substituted isoquinolinyl, unsubstituted or substituted quinazolinyl, unsubstituted or substituted quinoxalinyl, unsubstituted or substituted naphthyridinyl, unsubstituted or substituted indolyl, unsubstituted or substituted indazolyl, unsubstituted or substituted benzoxazolyl, unsubstituted or substituted benzisoxazolyl, unsubstituted or substituted benzofuranyl, unsubstituted or substituted benzothienyl, unsubstituted or substituted benzothiazolyl, unsubstituted or substituted benzimidazolyl, unsubstituted or substituted purinyl, unsubstituted or substituted cinnolinyl, unsubstituted or substituted phthalazinyl, unsubstituted or substituted pteridinyl, unsubstituted or substituted pyridopyrimidinyl, unsubstituted or substituted pyrazolopyrimidinyl, unsubstituted or substituted azaindolyl, unsubstituted or substituted indolinyl, unsubstituted or substituted isoindolinyl, unsubstituted or substituted indolinonyl, unsubstituted or substituted isoindolinonyl, or unsubstituted or substituted quinolinonyl, wherein if $R^B$ is substituted then $R^B$ is substituted with 1-2 $R^{12}$ and 0-2 $R^{13}$.

In some embodiments, each $R^{12}$ is independently hydrogen, halogen, unsubstituted or substituted $C_1$-$C_4$alkyl, unsubstituted or substituted $C_1$-$C_4$alkoxy, unsubstituted or substituted $C_1$-$C_4$fluoroalkyl, unsubstituted or substituted $C_1$-$C_4$fluoroalkoxy, unsubstituted or substituted monocyclic carbocycle, unsubstituted or substituted monocyclic heterocycle, —CN, —OH, —CO$_2$R$^{14}$, —CH$_2$CO$_2$R$^{14}$, —C(=O)NR$^{14}$R$^{15}$, —CH$_2$C(=O)NR$^{14}$R$^{15}$, —NR$^{14}$R$^{15}$, —CH$_2$NR$^{14}$R$^{15}$, —NR$^{14}$C(=O)R$^{15}$, —CH$_2$NR$^{14}$C(=O)R$^{15}$, —SR$^{14}$, —S(=O)R$^{15}$, —SO$_2$R$^{15}$, or —SO$_2$NR$^{14}$R$^{15}$, wherein if $R^{12}$ is substituted then $R^{12}$ is substituted with $R^{16}$; each $R^{13}$ is independently hydrogen, halogen, unsubstituted or substituted $C_1$-$C_4$alkyl, unsubstituted or substituted $C_1$-$C_4$alkoxy, unsubstituted or substituted $C_1$-$C_4$fluoroalkyl, unsubstituted or substituted $C_1$-$C_4$fluoroalkoxy, unsubstituted or substituted monocyclic carbocycle, unsubstituted or substituted monocyclic heterocycle, —CN, —OH, wherein if $R^{13}$ is substituted then $R^{13}$ is substituted with $R^{16}$.

In some embodiments, each $R^{12}$ is independently hydrogen, F, Cl, —CH$_3$, —OCH$_3$, —CF$_3$, —OCF$_3$, —CN, —OH, —CO$_2$H, —CH$_2$CO$_2$H, —C(=O)NH$_2$, —CH$_2$C(=O)NH$_2$, —NH$_2$, —CH$_2$NH$_2$, or —SO$_2$NH$_2$; each $R^{13}$ is independently hydrogen, F, Cl, —CH$_3$, —OCH$_3$, —CF$_3$, —OCF$_3$, —CN, or —OH.

In some embodiments, each $R^{10}$ is independently hydrogen, F, Cl, —CH$_3$, —OCH$_3$, —CF$_3$, —OCF$_3$, —CN, —OH, —CO$_2$H, —CH$_2$CO$_2$H, —C(=O)NH$_2$, —CH$_2$C(=O)NH$_2$, —NH$_2$, —CH$_2$NH$_2$, —NHC(=O)CH$_3$, or —CH$_2$NHC(=O)CH$_3$; and each $R^{11}$ is independently hydrogen, F, Cl, —CH$_3$, —OCH$_3$, —CF$_3$, —OCF$_3$, or —CN.

In some embodiments, $R^4$ is hydrogen, or unsubstituted or substituted $C_1$-$C_6$ alkyl, wherein if $R^4$ is substituted then it is substituted with 1-4 $R^{16}$; $R^5$ is hydrogen, or unsubstituted or substituted $C_1$-$C_6$ alkyl, wherein if $R^5$ is substituted then it is substituted with 1-4 $R^{16}$; $R^7$ is hydrogen; or $R^4$ and $R^5$ are taken together with the nitrogen atom to which they are attached to form a monocyclic 4- to 7-membered heterocyclic ring, wherein if the heterocyclic ring is substituted then the heterocyclic ring is substituted with 1-4 $R^{16}$; or $R^4$ and $R^7$ are taken together with the nitrogen atom to which they are attached to form a monocyclic 4- to 7-membered heterocyclic ring, wherein if the heterocyclic ring is substituted then the heterocyclic ring is substituted with 1-4 $R^{16}$ In some embodiments, $R^4$ is hydrogen, methyl, ethyl, n-propyl, i-propyl, n-butyl, butyl, sec-butyl, or tert-butyl; $R^5$ is hydrogen, methyl, ethyl, n-propyl, i-propyl, n-butyl, i-butyl, sec-butyl, or tert-butyl; $R^7$ is hydrogen; or $R^4$ and $R^5$ are taken together with the nitrogen atom to which they are attached to form an unsubstituted or substituted monocyclic 4- to 7-membered heterocyclic ring selected from unsubstituted or substituted azetidinyl, unsubstituted or substituted pyrrolidinyl, unsubstituted or substituted pyrrolidinonyl, unsubstituted or substituted piperidinyl, unsubstituted or substituted morpholinyl, unsubstituted or substituted thiomorpholinyl, unsubstituted or substituted piperazinyl, or unsubstituted or substituted azepanyl, wherein if the heterocyclic ring is substituted then the heterocyclic ring is substituted with 1-4 $R^{16}$; or $R^4$ and $R^7$ are taken together with the nitrogen atom to which they are attached to form an unsubstituted or substituted monocyclic 4- to 7-membered heterocyclic ring selected from unsubstituted or substituted azetidinyl, unsubstituted or substituted pyrrolidinyl, unsubstituted or substituted pyrrolidinonyl, unsubstituted or substituted piperidinyl, unsubstituted or substituted morpholinyl, unsubstituted or substituted thiomorpholinyl, unsubstituted or substituted piperazinyl, or unsubstituted or substituted azepanyl, wherein if the heterocyclic ring is substituted then the heterocyclic ring is substituted with 1-4 $R^{16}$.

In some embodiments, $R^4$ and $R^5$ are taken together with the nitrogen atom to which they are attached to form:

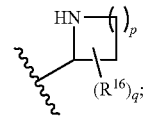

p is 1, 2, or 3; and q is 0, 1, or 2.

In some embodiments, $R^4$ and $R^5$ are taken together with the nitrogen atom to which they are attached to form:

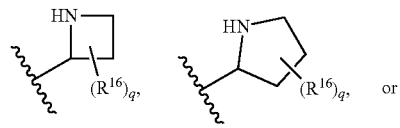

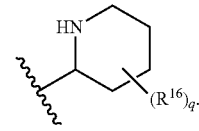

In some embodiments, $R^4$ and $R^5$ are taken together with the nitrogen atom to which they are attached to form:

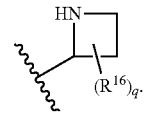

In some embodiments, $R^4$ and $R^5$ are taken together with the nitrogen atom to which they are attached to form:

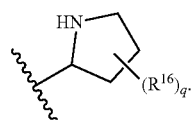

In some embodiments, $R^4$ and $R^5$ are taken together with the nitrogen atom to which they are attached to form:

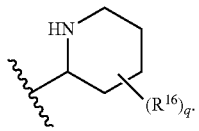

In some embodiments,

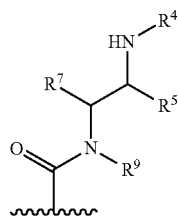

p is 1, 2, or 3; and q is 0, 1, or 2.

In some embodiments,

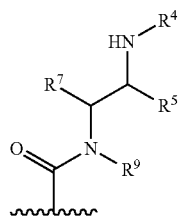

p is 1, 2, or 3; and q is 0, 1, or 2.

In some embodiments, $R^4$ is hydrogen, methyl, ethyl, n-propyl, i-propyl, n-butyl, butyl, sec-butyl, or tert-butyl; $R^5$ is hydrogen, methyl, ethyl, n-propyl, i-propyl, n-butyl, i-butyl, sec-butyl, or tert-butyl; and $R^7$ is hydrogen.

In some embodiments,

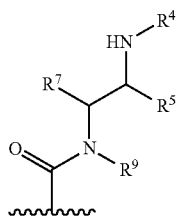

p is 1, 2, or 3; and q is 0, 1, or 2.

In some embodiments, p is 1. In some embodiments, p is 2. In some embodiments, p is 3.

In some embodiments, q is 0. In some embodiments, q is 1. In some embodiments, q is 2.

In some embodiments,

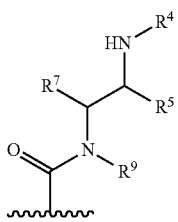

In some embodiments,

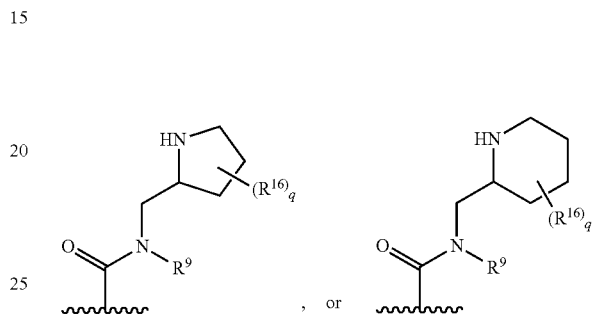

In some embodiments,

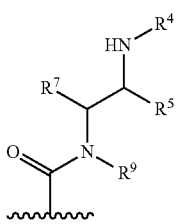

p is 1, 2, or 3; and q is 0, 1, or 2.

In some embodiments,

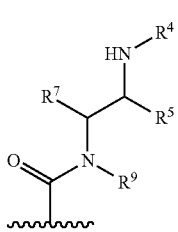

In some embodiments,

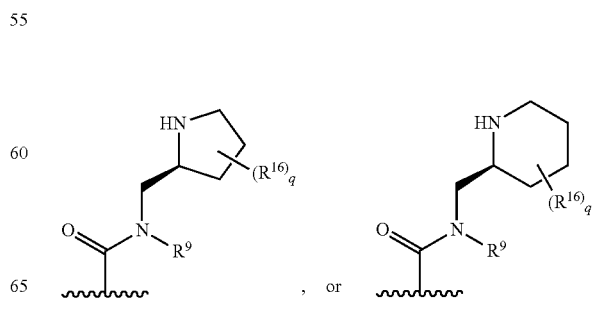

In some embodiments,

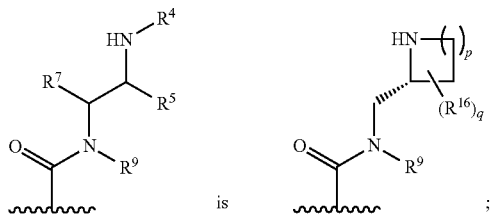

p is 1, 2, or 3; and q is 0, 1, or 2.

In some embodiments,

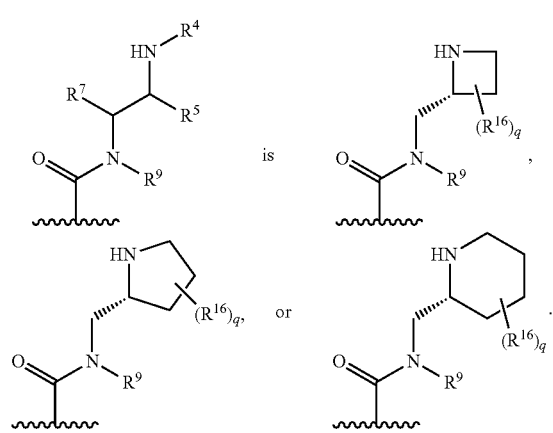

In some embodiments, $R^9$ is hydrogen, unsubstituted or substituted $C_1$-$C_6$ alkyl, or unsubstituted or substituted benzyl, wherein if $R^9$ is substituted then $R^9$ is substituted with 1-4 $R^{16}$.

In some embodiments, $R^9$ is methyl, ethyl, n-propyl, i-propyl, n-butyl, i-butyl, sec-butyl, tert-butyl, or benzyl.

In some embodiments, $R^9$ is methyl, or ethyl.

In some embodiments, $R^9$ is methyl.

In some embodiments, $R^9$ is as described in Table 1 or Table 2.

In some embodiments, $R^{10}$ is as described in Table 1 or Table 2.

In some embodiments, $R^{11}$ is as described in Table 1 or Table 2.

In some embodiments, $R^{12}$ is as described in Table 1 or Table 2.

In some embodiments, $R^{13}$ is as described in Table 1 or Table 2.

In some embodiments, $R^A$ is as described in Table 3. In some embodiments, $R^B$ is as described in Table 3.

Any combination of the groups described above for the various variables is contemplated herein. Throughout the specification, groups and substituents thereof are chosen by one skilled in the field to provide stable moieties and compounds.

Exemplary compounds of Formula (I) include the compounds described in the following Tables:

TABLE 1

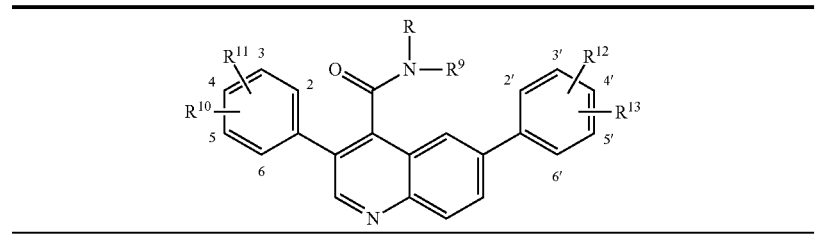

| Cpd No. | R | $R^9$ | $R^{10}$ | $R^{11}$ | $R^{12}$ | $R^{13}$ |
|---|---|---|---|---|---|---|
| 1-1 | ⟨pyrrolidinyl-NH⟩ | $CH_3$ | 3-$CH_3$ | 5-Cl | 3'-OH | H |
| 1-2 | ⟨CH(NH$_2$)CH$_2$⟩ | $CH_3$ | 3-Cl | 5-$CH_3$ | 3'-OH | H |
| 1-3 | ⟨CH(NH$_2$)CH$_2$⟩ | $CH_3$ | 3-$CH_3$ | 5-Cl | 3'-OH | H |

TABLE 1-continued
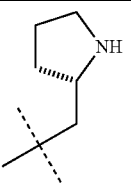
| Cpd No. | R | R⁹ | R¹⁰ | R¹¹ | R¹² | R¹³ |
| --- | --- | --- | --- | --- | --- | --- |
| 1-4 | 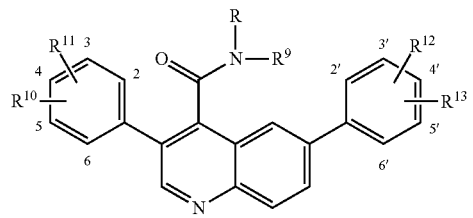 | $CH_3$ | 3-$CH_3$ | 5-F | 3'-OH | H |
| 1-5 | 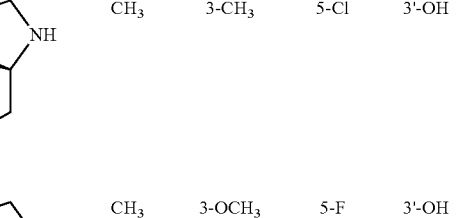 | $CH_3$ | 3-$CH_3$ | 5-Cl | 3'-OH | H |
| 1-6 | 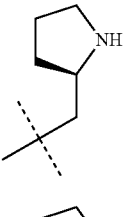 | $CH_3$ | 3-$OCH_3$ | 5-F | 3'-OH | H |
| 1-7 | 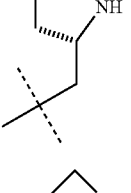 | $CH_3$ | 3-$CH_3$ | 5-F | 3'-OH | H |
| 1-8 | 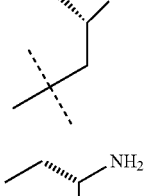 | $CH_3$ | 3-$CH_3$ | 5-Cl | 3'-OH | 5'-$CONH_2$ |
| 1-9 | 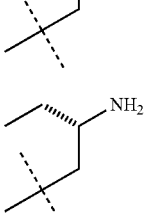 | $CH_3$ | 3-$CH_3$ | 5-F | 3'-OMe | 5'-CN |
| 1-10 | 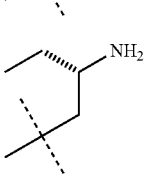 | $CH_3$ | 3-$CH_3$ | 5-F | 3'-OH | 5'-CN |
| 1-11 | 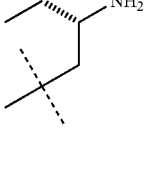 | $CH_3$ | 3-$CH_3$ | 5-F | 3'-OH | 6'-$CH_3$ |

TABLE 1-continued

| Cpd No. | R | R⁹ | R¹⁰ | R¹¹ | R¹² | R¹³ |
|---|---|---|---|---|---|---|
| 1-12 | (S)-2-aminobutyl-neopentyl | CH₃ | 3-CH₃ | 5-F | 3'-CN | 2'-CH₃ |
| 1-13 | (S)-2-aminobutyl-neopentyl | CH₃ | 3-CH₃ | 5-F | 3'-F | 2'-CH₃ |
| 1-14 | (S)-2-aminobutyl-neopentyl | CH₃ | 3-CH₃ | 5-F | 3'-CN | 6'-CH₃ |
| 1-15 | (S)-2-aminobutyl-neopentyl | CH₃ | 3-CH₃ | 5-F | 3'-CN | 5'-F |
| 1-16 | pyrrolidinylmethyl | CH₃ | 3-CH₃ | 5-F | 3-CN | H |
| 1-17 | (S)-2-aminobutyl-neopentyl | CH₃ | 3-CH₃ | 5-F | 3'-OMe | 5'-F |
| 1-18 | (S)-2-aminobutyl-neopentyl | CH₃ | 3-F | H | 3'-OH | H |
| 1-19 | (R)-2-aminobutyl-neopentyl | CH₃ | 3-CH₃ | 5-F | 3'-CN | 5'-OMe |

TABLE 1-continued

| Cpd No. | R | R⁹ | R¹⁰ | R¹¹ | R¹² | R¹³ |
|---|---|---|---|---|---|---|
| 1-20 | (S)-2-aminobutyl group | CH₃ | 3-CH₃ | 5-F | 3'-CN | 5'-F |
| 1-21 | (pyrrolidin-2-yl)methyl | CH₃ | 3-CH₃ | 5-F | 3'-CN | 5'-OMe |
| 1-22 | (pyrrolidin-2-yl)methyl | CH₃ | 3-F | 5-F | 3'-CN | 5'-F |
| 1-23 | (pyrrolidin-2-yl)methyl | CH₃ | 3-F | 5-F | 3'-OH | 2'-F |
| 1-24 | (pyrrolidin-2-yl)methyl | CH₃ | 3-CH₃ | 5-F | 3'-CN | 5'-F |
| 1-25 | (pyrrolidin-2-yl)methyl | CH₃ | 3-F | 5-F | 3'-CN | 2'-F |
| 1-26 | (pyrrolidin-2-yl)methyl | CH₃ | 3-F | 5-F | 3'-CONH₂ | 5'-F |

TABLE 1-continued

| Cpd No. | R | R⁹ | R¹⁰ | R¹¹ | R¹² | R¹³ |
|---|---|---|---|---|---|---|
| 1-27 | (S)-pyrrolidin-2-ylmethyl | CH₃ | 3-F | 5-F | 3'-CN | 6'-OMe |
| 1-28 | (S)-pyrrolidin-2-ylmethyl | CH₃ | 3-F | 5-F | 3'-CN | 6'-F |
| 1-29 | morpholin-3-ylmethyl | CH₃ | 3-CH₃ | 5-F | 3'-OH | H |
| 1-30 | (S)-pyrrolidin-2-ylmethyl | CH₃ | 3-F | 5-F | 3'-CN | 5'-OMe |
| 1-31 | (S)-pyrrolidin-2-ylmethyl | CH₃ | 3-F | 5-F | 3'-OH | 2'-Cl |
| 1-32 | (S)-pyrrolidin-2-ylmethyl | CH₃ | 3-F | 5-F | 3'-CN | 5'-OMe |
| 1-33 | (S)-pyrrolidin-2-ylmethyl | CH₃ | 3-CH₃ | 5-F | 3'-CONH₂ | 5'-F |

TABLE 1-continued
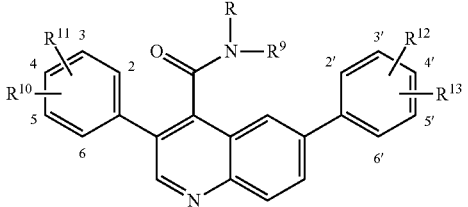
| Cpd No. | R | R⁹ | R¹⁰ | R¹¹ | R¹² | R¹³ |
|---|---|---|---|---|---|---|
| 1-34 | 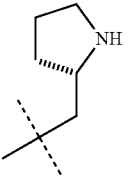 | $CH_3$ | 3-F | 5-OH | 3'-CN | 5'-F |
| 1-35 | 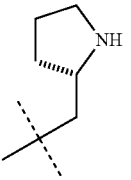 | $CH_3$ | 3-$CH_2CH_2OH$ | 5-F | 3'-CN | 5'-F |
| 1-36 | 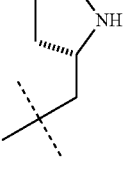 | $CH_3$ | 3-$CH_3$ | 5-F | 3'-F | 5'-$CO_2H$ |
| 1-37 | 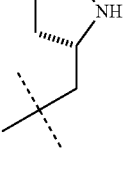 | $CH_3$ | 3-$CH_3$ | 5-F | 3'-F | 5'-O$(CH_2)_3CO_2H$ |
| 1-38 | 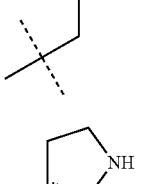 | $CH_3$ | 3-F | 5-F | 3'-OH | 5'-CN |
| 1-39 | 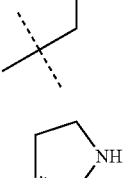 | $CH_3$ | 3-$OCH_2CH_2OH$ | 5-F | 3'-CN | 5'-F |
| 1-40 | 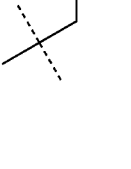 | $CH_3$ | 3-$CH_3$ | 5-F | 3'-CN | 5'-$CF_3$ |

TABLE 1-continued
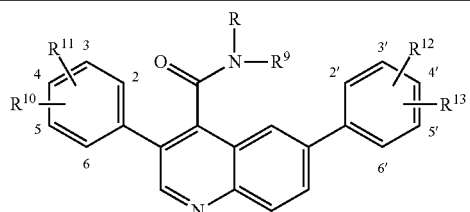
| Cpd No. | R | R⁹ | R¹⁰ | R¹¹ | R¹² | R¹³ |
|---|---|---|---|---|---|---|
| 1-41 | pyrrolidinyl-CH₂-C(CH₃)₂- | CH₃ | 3-CH₃ | 5-F | 3'-OH | 2'-Cl |
| 1-42 | pyrrolidinyl-CH₂-C(CH₃)₂- | CH₃ | 3-OCH₂CH₂OCH₃ | 5-F | 3'-CN | 5'-F |
| 1-43 | pyrrolidinyl-CH₂-C(CH₃)₂- | CH₃ | 3-CH₃ | 5-F | 3'-OH | 2'-CH₂OCH₃ |
| 1-44 | pyrrolidinyl-CH₂-C(CH₃)₂- | CH₃ | 3-CH₃ | 5-F | 3'-CO₂H | H |
| 1-45 | pyrrolidinyl-CH₂-C(CH₃)₂- | CH₃ | 3-CH₂CH₂OH | 5-F | 3'-CN | 2-CH₃ |
| 1-46 | pyrrolidinyl-CH₂-C(CH₃)₂- | CH₃ | 3-CH₃ | 5-F | 4'-CO₂H | H |
| 1-47 | pyrrolidinyl-CH₂-C(CH₃)₂- | CH₃ | 3-CH₃ | 5-F | 2'-CO₂H | H |

TABLE 1-continued
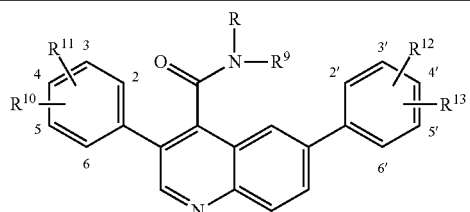
| Cpd No. | R | R⁹ | R¹⁰ | R¹¹ | R¹² | R¹³ |
|---|---|---|---|---|---|---|
| 1-48 | pyrrolidinyl-CH₂- | CH₃ | 3-CH₃ | 5-F | 3'-CH₂CO₂H | H |
| 1-49 | pyrrolidinyl-CH₂- | CH₃ | 3-CH₃ | 5-F | 3'-CH₂CO₂CH₃ | H |
| 1-50 | pyrrolidinyl-CH₂- | CH₃ | 3-CH₃ | 5-F | 3'-(CH₂)₂CO₂H | H |
| 1-51 | pyrrolidinyl-CH₂- | CH₃ | 3-CH₃ | 5-F | 3'-CN | 2'-CH₃ |
| 1-52 | pyrrolidinyl-CH₂- | CH₃ | 3-CH₃ | 5-F | 3'-CN | 6'-CH₃ |
| 1-53 | pyrrolidinyl-CH₂- | CH₃ | 3-CH₃ | 5-F | 3'-CONH₂ | 2'-F |
| 1-54 | pyrrolidinyl-CH₂- | CH₃ | 3-CH₃ | 5-F | 3'-CONH₂ | 4'-F |

TABLE 1-continued
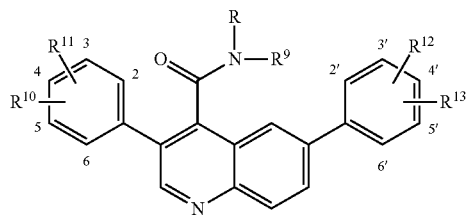
| Cpd No. | R | R⁹ | R¹⁰ | R¹¹ | R¹² | R¹³ |
|---|---|---|---|---|---|---|
| 1-55 | ⟨ethyl-CH-NH₂⟩ | CH₃ | 3-F | 5-F | 3'-CN | 5'-F |
| 1-56 | ⟨pyrrolidin-2-ylmethyl⟩ | CH₃ | 2-F | 5-F | 3'-CN | 5'-F |
| 1-57 | ⟨pyrrolidin-2-ylmethyl⟩ | CH₃ | 2-Cl | 5-CH₃ | 3'-CN | 5'-F |
| 1-58 | ⟨pyrrolidin-2-ylmethyl⟩ | CH₃ | 2-CH₃ | 5-F | 3'-CN | 5'-F |
| 1-59 | ⟨pyrrolidin-2-ylmethyl⟩ | CH₃ | 3-CH₃ | 5-F | 3'-CH₂CO₂H | 5'-F |
| 1-60 | ⟨pyrrolidin-2-ylmethyl⟩ | CH₃ | 3-CH₃ | 5-F | 3'-SO₂NH₂ | H |
| 1-61 | ⟨pyrrolidin-3-yl⟩ | CH₃ | 3-CH₃ | 5-F | 3'-F | 5'-F |

TABLE 1-continued
| Cpd No. | R | R⁹ | R¹⁰ | R¹¹ | R¹² | R¹³ |
|---|---|---|---|---|---|---|
| 1-62 | 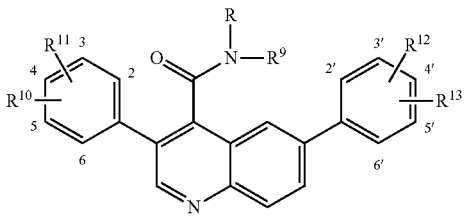 | CH₃ | 3-OCH₂CO₂H | 5-F | 3'-F | 5'-F |
| 1-63 | 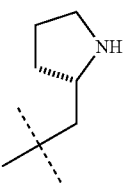 | CH₃ | 3-CH₃ | 5-F | 3'-F | 5'-F |
| 1-64 | 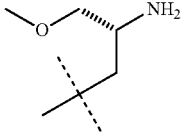 | CH₃ | 3-CH₃ | 5-F | 3'-OCH₃ | 6'-Cl |
| 1-65 | 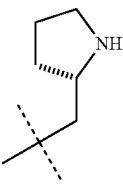 | CH₃ | 3-OCH₂CO₂H | 5-Cl | 3'-CN | 5'-F |
| 1-66 | 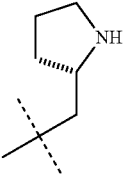 | CH₃ | 3-CH₃ | 5-F | 3'-SONH₂ | 5'-F |
| 1-67 | 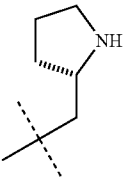 | CH₃ | 3-F | 2-F | 3'-CN | 5'-F |
| 1-68 | 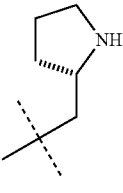 | CH₃ | 3-CH₃ | 5-F | 3'-F | 5'-F |

TABLE 1-continued
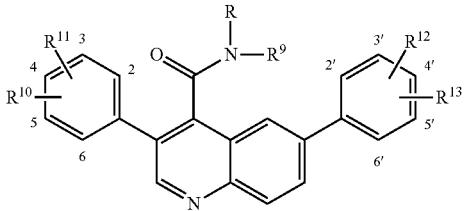
| Cpd No. | R | R⁹ | R¹⁰ | R¹¹ | R¹² | R¹³ |
|---|---|---|---|---|---|---|
| 1-69 | 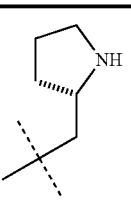 | CH₃ | 3-C(CH₃)₂OH | 5-F | 3'-CN | 5'-F |
| 1-70 | 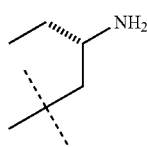 | CH₃ | 3-CH₃ | 5-F | 3'-CF₃ | 5'-F |
| 1-71 | 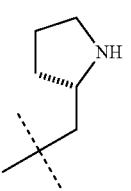 | CH₃ | 3-C(CH₃)=CH₂ | 5-F | 3'-CN | 5'-F |
| 1-72 | 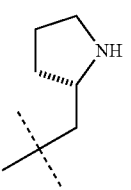 | CH₃ | 3-CH₃ | 5-F | 3'-CONH₂ | 4'-OH |
| 1-73 | 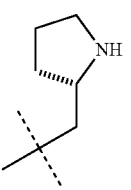 | CH₃ | 3-CONMe₂ | H | 3'-OH | H |
| 1-74 | 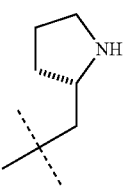 | CH₃ | 3-CH₃ | 5-F | 3'-CH₂CONH₂ | 5'-F |
| 1-75 | 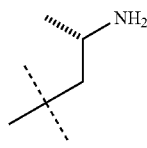 | CH₃ | 3-CH₃ | 5-F | 3'-CONH₂ | 5'-OCH₃ |

TABLE 1-continued
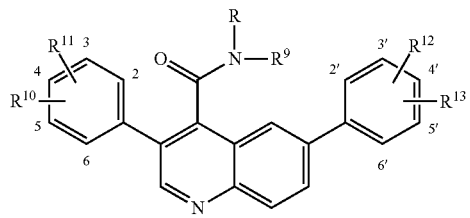
| Cpd No. | R | R⁹ | R¹⁰ | R¹¹ | R¹² | R¹³ |
|---|---|---|---|---|---|---|
| 1-76 | pyrrolidine | CH₃ | 3-CH₃ | 5-F | 3'-CN | 5'-CONHCH₃ |
| 1-77 | pyrrolidine | CH₃ | 3-CH₃ | 5-F | 3'-CN | 2'-OH |
| 1-78 | pyrrolidine | CH₃ | 3-CH₃ | 5-F | 3'-CONH₂ | 5'-CN |
| 1-79 | fluoropyrrolidine | CH₃ | 3-CH₃ | 5-F | 3'-CN | 5'-F |
| 1-80 | azetidine | CH₃ | 3-CH₃ | 5-Cl | 3'-CN | 5'-F |
| 1-81 | azetidine | CH₃ | 3-CH₃ | 5-Cl | 3'-CONH₂ | 5'-F |
| 1-82 | azetidine | CH₃ | 3-Cl | 5-Cl | 3'-CN | 5'-F |

TABLE 1-continued
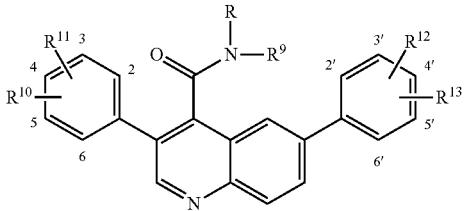
| Cpd No. | R | R⁹ | R¹⁰ | R¹¹ | R¹² | R¹³ |
|---|---|---|---|---|---|---|
| 1-83 | 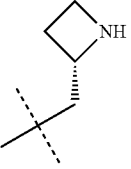 | CH₃ | 3-Cl | 5-Cl | 3'-CONH₂ | 5'-F |
| 1-84 | 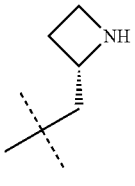 | CH₃ | 3-CH₃ | 5-Cl | 3'-CN | 2'-OH |
| 1-85 | 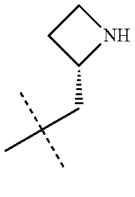 | CH₃ | 3-Cl | 5-Cl | 3'-CN | 2'-OH |
| 1-86 | 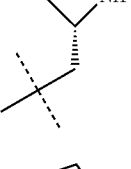 | CH₃ | 3-Cl | 5-F | 3'-CN | 2'-OH |
| 1-87 | 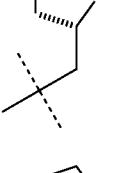 | CH₃ | 3-Cl | 5-F | 3'-CN | 2'-OH |
| 1-88 | 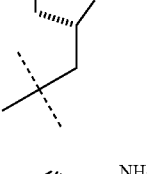 | CH₃ | 3-Cl | 5-F | 3'-CONH₂ | 5'-F |
| 1-89 |  | CH₃ | 3-CH₃ | 5-F | 3'-F | 5'-F |

TABLE 1-continued

| Cpd No. | R | R⁹ | R¹⁰ | R¹¹ | R¹² | R¹³ |
|---|---|---|---|---|---|---|
| 1-90 | (3-fluoropyrrolidin-2-ylmethyl, with neopentyl linker) | $CH_3$ | 3-$CH_3$ | 5-F | 3'-CN | 5'-F |
| 1-91 | (pyrrolidin-2-ylmethyl, with neopentyl linker) | $CH_3$ | 3-$CH_3$ | 5-F | 3'-F | 2'-OH |

Compounds in Table 1 are named:

1-1: 3-(3-chloro-5-methylphenyl)-6-(3-hydroxyphenyl)-N-methyl-N-[(2S)-pyrrolidin-2-ylmethyl]quinoline-4-carboxamide;

1-2: N-[(2S)-2-aminopropyl]-3-(3-chloro-5-methylphenyl)-6-(3-hydroxyphenyl)-N-methylquinoline-4-carboxamide;

1-3: N-[(2S)-2-aminobutyl]-3-(3-chloro-5-methylphenyl)-6-(3-hydroxyphenyl)-N-methylquinoline-4-carboxamide;

1-4: 3-(3-fluoro-5-methylphenyl)-6-(3-hydroxyphenyl)-N-methyl-N-[(2S)-pyrrolidin-2-ylmethyl]quinoline-4-carboxamide;

1-5: 3-(3-chloro-5-methylphenyl)-6-(3-hydroxyphenyl)-N-methyl-N-[(2R)-pyrrolidin-2-ylmethyl]quinoline-4-carboxamide;

1-6: 3-(3-fluoro-5-methoxyphenyl)-6-(3-hydroxyphenyl)-N-methyl-N-[(2S)-pyrrolidin-2-ylmethyl]quinoline-4-carboxamide;

1-7: N-[(2S)-azetidin-2-ylmethyl]-3-(3-fluoro-5-methylphenyl)-6-(3-hydroxyphenyl)-N-methylquinoline-4-carboxamide;

1-8: N-[(2S)-2-aminobutyl]-6-(3-carbamoyl-5-hydroxyphenyl)-3-(3-chloro-5-methylphenyl)-N-methylquinoline-4-carboxamide;

1-9: N-[(2S)-2-aminobutyl]-6-(3-cyano-5-methoxyphenyl)-3-(3-fluoro-5-methylphenyl)-N-methylquinoline-4-carboxamide;

1-10: N-[(2S)-2-aminobutyl]-6-(3-cyano-5-hydroxyphenyl)-3-(3-fluoro-5-methylphenyl)-N-methylquinoline-4-carboxamide;

1-11: N-[(2S)-2-aminobutyl]-3-(3-fluoro-5-methylphenyl)-6-(5-hydroxy-2-methylphenyl)-N-methylquinoline-4-carboxamide;

1-12: N-[(2S)-2-aminobutyl]-6-(3-cyano-2-methylphenyl)-3-(3-fluoro-5-methylphenyl)-N-methylquinoline-4-carboxamide;

1-13: N-[(2S)-2-aminobutyl]-6-(3-fluoro-2-methylphenyl)-3-(3-fluoro-5-methylphenyl)-N-methylquinoline-4-carboxamide;

1-14: N-[(2S)-2-aminobutyl]-6-(5-cyano-2-methylphenyl)-3-(3-fluoro-5-methylphenyl)-N-methylquinoline-4-carboxamide;

1-15: N-[(2S)-2-aminobutyl]-6-(3-cyano-5-fluorophenyl)-3-(3-fluoro-5-methylphenyl)-N-methylquinoline-4-carboxamide;

1-16: 6-(3-cyanophenyl)-3-(3-fluoro-5-methylphenyl)-N-methyl-N-[(2S)-pyrrolidin-2-ylmethyl]quinoline-4-carboxamide;

1-17: N-[(2S)-2-aminobutyl]-6-(3-fluoro-5-methoxyphenyl)-3-(3-fluoro-5-methylphenyl)-N-methylquinoline-4-carboxamide;

1-18: 3-(3-fluorophenyl)-6-(3-hydroxyphenyl)-N-methyl-N-[(2S)-pyrrolidin-2-ylmethyl]quinoline-4-carboxamide;

1-19: N-[(2S)-2-aminopropyl]-6-(3-cyano-5-methoxyphenyl)-3-(3-fluoro-5-methylphenyl)-N-methylquinoline-4-carboxamide;

1-20: N-[(2S)-2-aminopropyl]-6-(3-cyano-5-fluorophenyl)-3-(3-fluoro-5-methylphenyl)-N-methylquinoline-4-carboxamide;

1-21: 6-(3-cyano-5-methoxyphenyl)-3-(3-fluoro-5-methylphenyl)-N-methyl-N-[(2S)-pyrrolidin-2-ylmethyl]quinoline-4-carboxamide;

1-22: 6-(3-cyano-5-fluorophenyl)-3-(3,5-difluorophenyl)-N-methyl-N-[(2S)-pyrrolidin-2-ylmethyl]quinoline-4-carboxamide;

1-23: 3-(3,5-difluorophenyl)-6-(2-fluoro-3-hydroxyphenyl)-N-methyl-N-[(2S)-pyrrolidin-2-ylmethyl]quinoline-4-carboxamide;

1-24: 6-(3-cyano-5-fluorophenyl)-3-(3-fluoro-5-methylphenyl)-N-methyl-N-[(2S)-pyrrolidin-2-ylmethyl]quinoline-4-carboxamide;

1-25: 6-(3-cyano-2-fluorophenyl)-3-(3,5-difluorophenyl)-N-methyl-N-[(2S)-pyrrolidin-2-ylmethyl]quinoline-4-carboxamide;

1-26: 6-(3-carbamoyl-5-fluorophenyl)-3-(3,5-difluorophenyl)-N-methyl-N-[(2S)-pyrrolidin-2-ylmethyl]quinoline-4-carboxamide;

1-27: 6-(5-cyano-2-methoxyphenyl)-3-(3,5-difluorophenyl)-N-methyl-N-[(2S)-pyrrolidin-2-ylmethyl]quinoline-4-carboxamide;

1-28: 6-(5-cyano-2-methoxyphenyl)-3-(3,5-difluorophenyl)-N-methyl-N-[(2S)-pyrrolidin-2-ylmethyl]quinoline-4-carboxamide;

1-29: 3-(3-fluoro-5-methylphenyl)-6-(3-hydroxyphenyl)-N-methyl-N-(morpholin-3-ylmethyl)quinoline-4-carboxamide;

1-30: 6-(3-cyano-5-methoxyphenyl)-3-(3,5-difluorophenyl)-N-methyl-N-[(2S)-pyrrolidin-2-ylmethyl]quinoline-4-carboxamide;

1-31: 6-(2-chloro-3-hydroxyphenyl)-3-(3,5-difluorophenyl)-N-methyl-N-[(2S)-pyrrolidin-2-ylmethyl]quinoline-4-carboxamide;

1-32: N-[(2S)-2-aminobutyl]-6-(3-cyano-5-methoxyphenyl)-3-(3,5-difluorophenyl)-N-methylquinoline-4-carboxamide;

1-33: 6-(3-carbamoyl-5-fluorophenyl)-3-(3-fluoro-5-methylphenyl)-N-methyl-N-[(2S)-pyrrolidin-2-ylmethyl]quinoline-4-carboxamide;

1-34: 6-(3-cyano-5-fluorophenyl)-3-(3-fluoro-5-hydroxyphenyl)-N-methyl-N-[(2S)-pyrrolidin-2-ylmethyl]quinoline-4-carboxamide;

1-35: 6-(3-cyano-5-fluorophenyl)-3-[3-fluoro-5-(2-hydroxyethyl)phenyl]-N-methyl-N-[(2S)-pyrrolidin-2-ylmethyl]quinoline-4-carboxamide;

1-36: 3-fluoro-5-[3-(3-fluoro-5-methylphenyl)-4-{methyl[(2S)-pyrrolidin-2-ylmethyl]carbamoyl}quinolin-6-yl]benzoic acid;

1-37: 4-{3-[6-(3-cyano-5-fluorophenyl)-4-{methyl[(2S)-pyrrolidin-2-ylmethyl]carbamoyl}quinolin-3-yl]-5-fluorophenoxy}butanoic acid;

1-38: N-[(2S)-2-aminobutyl]-6-(3-cyano-5-hydroxyphenyl)-3-(3,5-difluorophenyl)-N-methylquinoline-4-carboxamide;

1-39: 6-(3-cyano-5-fluorophenyl)-3-[3-fluoro-5-(2-hydroxyethoxy)phenyl]-N-methyl-N-[(2S)-pyrrolidin-2-ylmethyl]quinoline-4-carboxamide;

1-40: 6-[3-cyano-5-(trifluoromethyl)phenyl]-3-(3-fluoro-5-methylphenyl)-N-methyl-N-[(2S)-pyrrolidin-2-ylmethyl]quinoline-4-carboxamide;

1-41: 6-(2-chloro-3-hydroxyphenyl)-3-(3-fluoro-5-methylphenyl)-N-methyl-N-[(2S)-pyrrolidin-2-ylmethyl]quinoline-4-carboxamide;

1-42: 6-(3-cyano-5-fluorophenyl)-3-[3-fluoro-5-(2-methoxyethoxy)phenyl]-N-methyl-N-[(2S)-pyrrolidin-2-ylmethyl]quinoline-4-carboxamide;

1-43: 3-(3-fluoro-5-methylphenyl)-6-[3-hydroxy-2-(methoxymethyl)phenyl]-N-methyl-N-[(2S)-pyrrolidin-2-ylmethyl]quinoline-4-carboxamide 1-44: 3-[3-(3-fluoro-5-methylphenyl)-4-{methyl[(2S)-pyrrolidin-2-ylmethyl]carbamoyl}quinolin-6-yl]benzoic acid;

1-45: 6-(3-cyano-2-methylphenyl)-3-[3-fluoro-5-(2-hydroxyethyl)phenyl]-N-methyl-N-[(2S)-pyrrolidin-2-ylmethyl]quinoline-4-carboxamide;

1-46: 4-[3-(3-fluoro-5-methylphenyl)-4-{methyl[(2S)-pyrrolidin-2-ylmethyl]carbamoyl}quinolin-6-yl]benzoic acid;

1-47: 2-[3-(3-fluoro-5-methylphenyl)-4-{methyl[(2S)-pyrrolidin-2-ylmethyl]carbamoyl}quinolin-6-yl]benzoic acid;

1-48: 2-{3-[3-(3-fluoro-5-methylphenyl)-4-{methyl[(2S)-pyrrolidin-2-ylmethyl]carbamoyl}quinolin-6-yl]phenyl}acetic acid;

1-49: methyl 2-{3-[3-(3-fluoro-5-methylphenyl)-4-{methyl[(2S)-pyrrolidin-2-ylmethyl]carbamoyl}quinolin-6-yl]phenyl}acetate;

1-50: 3-{3-[3-(3-fluoro-5-methylphenyl)-4-{methyl[(2S)-pyrrolidin-2-ylmethyl]carbamoyl}quinolin-6-yl]phenyl}propanoic acid;

1-51: 6-(3-cyano-2-methylphenyl)-3-(3,5-difluorophenyl)-N-methyl-N-[(2S)-pyrrolidin-2-ylmethyl]quinoline-4-carboxamide;

1-52: 6-(5-cyano-2-methylphenyl)-3-(3,5-difluorophenyl)-N-methyl-N-[(2S)-pyrrolidin-2-ylmethyl]quinoline-4-carboxamide;

1-53: 6-(3-carbamoyl-2-fluorophenyl)-3-(3-fluoro-5-methylphenyl)-N-methyl-N-[(2S)-pyrrolidin-2-ylmethyl]quinoline-4-carboxamide;

1-54: 6-(3-carbamoyl-4-fluorophenyl)-3-(3-fluoro-5-methylphenyl)-N-methyl-N-[(2S)-pyrrolidin-2-ylmethyl]quinoline-4-carboxamide;

1-55: N-[(2S)-2-aminobutyl]-6-(3-cyano-5-fluorophenyl)-3-(3,5-difluorophenyl)-N-methylquinoline-4-carboxamide;

1-56: 6-(3-cyano-5-fluorophenyl)-3-(2,5-difluorophenyl)-N-methyl-N-[(2S)-pyrrolidin-2-ylmethyl]quinoline-4-carboxamide;

1-57: 3-(2-chloro-5-methylphenyl)-6-(3-cyano-5-fluorophenyl)-N-methyl-N-[(2S)-pyrrolidin-2-ylmethyl]quinoline-4-carboxamide 1-58: 6-(3-cyano-5-fluorophenyl)-3-(5-fluoro-2-methylphenyl)-N-methyl-N-[(2S)-pyrrolidin-2-ylmethyl]quinoline-4-carboxamide 1-59: 2-{3-fluoro-5-[3-(3-fluoro-5-methylphenyl)-4-{methyl[(2S)-pyrrolidin-2-ylmethyl]carbamoyl}quinolin-6-yl]phenyl}acetic acid;

1-60: 3-(3-fluoro-5-methylphenyl)-N-methyl-N-[(2S)-pyrrolidin-2-ylmethyl]-6-(3-sulfamoylphenyl)quinoline-4-carboxamide;

1-61: 6-(3,5-difluorophenyl)-3-(3-fluoro-5-methylphenyl)-N-methyl-N-[(3S)-pyrrolidin-3-yl]quinoline-4-carboxamide;

1-62: 6-(3,5-difluorophenyl)-3-(3-fluoro-5-methylphenyl)-N-methyl-N-[(2S)-pyrrolidin-2-ylmethyl]quinoline-4-carboxamide;

1-63: 6-(6-carbamoylpyrazin-2-yl)-3-(3-fluoro-5-methylphenyl)-N-methyl-N-[(2S)-pyrrolidin-2-ylmethyl]quinoline-4-carboxamide;

1-64: 6-(2-chloro-5-methoxyphenyl)-3-(3-fluoro-5-methylphenyl)-N-methyl-N-[(2S)-pyrrolidin-2-ylmethyl]quinoline-4-carboxamide;

1-65: 2-{3-chloro-5-[6-(3-cyano-5-fluorophenyl)-4-{methyl[(2S)-pyrrolidin-2-ylmethyl]carbamoyl}quinolin-3-yl]phenoxy}acetic acid;

1-66: 3-(3-fluoro-5-methylphenyl)-6-(3-fluoro-5-sulfamoylphenyl)-N-methyl-N-[(2S)-pyrrolidin-2-ylmethyl]quinoline-4-carboxamide;

1-67: 6-(3-cyano-5-fluorophenyl)-3-(2,3-difluorophenyl)-N-methyl-N-[(2S)-pyrrolidin-2-ylmethyl]quinoline-4-carboxamide;

1-68: N-[(2S)-2-amino-3-methylbutyl]-6-(3,5-difluorophenyl)-3-(3-fluoro-5-methylphenyl)-N-methylquinoline-4-carboxamide;

1-69: 6-(3-cyano-5-fluorophenyl)-3-[3-fluoro-5-(2-hydroxypropan-2-yl)phenyl]-N-methyl-N -[(2S)-pyrrolidin-2-ylmethyl]quinoline-4-carboxamide;

1-70: N-[(2S)-2-aminobutyl]-6-[3-fluoro-5-(trifluoromethyl)phenyl]-3-(3-fluoro-5-methylphenyl)-N-methylquinoline-4-carboxamide;

1-71: 6-(3-cyano-5-fluorophenyl)-3-[3-fluoro-5-(prop-1-en-2-yl)phenyl]-N-methyl-N-[(2S) -pyrrolidin-2-ylmethyl]quinoline-4-carboxamide;

1-72: 6-(3-carbamoyl-4-hydroxyphenyl)-3-(3-fluoro-5-methylphenyl)-N-methyl-N-[(2S) -pyrrolidin-2-ylmethyl]quinoline-4-carboxamide;

1-73: 3-[3-(dimethylcarbamoyl)phenyl]-6-(3-hydroxyphenyl)-N-methyl-N-[(2S)-pyrrolidin-2-ylmethyl]quinoline-4-carboxamide;

1-74: 6- [3-(carbamoylmethyl)-5-fluorophenyl]-3-(3-fluoro-5-methylphenyl)-N-methyl-N -[(2S)-pyrrolidin-2-ylmethyl]quinoline-4-carboxamide;

1-75: N- [(2S)-2-aminopropyl]-6-(3-carbamoyl-5-methoxyphenyl)-3-(3-fluoro-5-methylphenyl) -N-methylquinoline-4-carboxamide;

1-76: 3-(4-{[(2S)-2-aminopropyl](methyl)carbamoyl}-3-(3-fluoro-5-methylphenyl)quinolin-6-yl)-5-methoxybenzoic acid;

1-76: 6-[3-cyano-5-(methylcarbamoyl)phenyl]-3-(3-fluoro-5-methylphenyl)-N-methyl-N-[(2S) -pyrrolidin-2-ylmethyl]quinoline-4-carboxamide;

1-77: 6-(3-cyano-2-hydroxyphenyl)-3-(3-fluoro-5-methylphenyl)-N-methyl-N-[(2S)-pyrrolidin -2-ylmethyl]quinoline-4-carboxamide;

1-78: 6-(3-carbamoyl-5-cyanophenyl)-3-(3,5-difluorophenyl)-N-methyl-N-[(2S)-pyrrolidin-2-ylmethyl]quinoline-4-carboxamide;

1-79: 6-(3-cyano-5-fluorophenyl)-3-(3-fluoro-5-methylphenyl)-N-{[(2S,4R)-4-fluoropyrrolidin -2-yl]methyl}-N-methylquinoline-4-carboxamide;

1-80: N-[(2S)-azetidin-2-ylmethyl]-3-(3-chloro-5-methylphenyl)-6-(3-cyano-5-fluorophenyl)-N -methylquinoline-4-carboxamide;

1-81: N-[(2S)-azetidin-2-ylmethyl]-6-(3-carbamoyl-5-fluorophenyl)-3-(3-chloro-5-methylphenyl)-N-methylquinoline-4-carboxamide;

1-82: N-[(2S)-azetidin-2-ylmethyl]-6-(3-cyano-5-fluorophenyl)-3-(3,5-dichlorophenyl)-N -methylquinoline-4-carboxamide;

1-83: N-[(2S)-azetidin-2-ylmethyl]-6-(3-carbamoyl-5-fluorophenyl)-3-(3,5-dichlorophenyl)-N -methylquinoline-4-carboxamide;

1-84: N-[(2S)-azetidin-2-ylmethyl]-3-(3-chloro-5-methylphenyl)-6-(3-cyano-2-hydroxyphenyl) -N-methylquinoline-4-carboxamide;

1-85: N-[(2S)-azetidin-2-ylmethyl]-6-(3-cyano-2-hydroxyphenyl)-3-(3,5-dichlorophenyl)-N -ethylquinoline-4-carboxamide;

1-86: N-[(2S)-azetidin-2-ylmethyl]-3-(3-chloro-5-fluorophenyl)-6-(3-cyano-2-hydroxyphenyl) -N-methylquinoline-4-carboxamide;

1-87: 3-(3-chloro-5-fluorophenyl)-6-(3-cyano-2-hydroxyphenyl)-N-methyl-N-[(2S)-pyrrolidin -2-ylmethyl]quinoline-4-carboxamide;

1-88: 6-(3-carbamoyl-5-methylphenyl)-3-(3-chloro-5-fluorophenyl)-N-methyl-N-[(2S) -pyrrolidin-2-ylmethyl]quinoline-4-carboxamide;

1-89: N-[(2S)-2-amino-4-fluorobutyl]-6-(3,5-difluorophenyl)-3-(3-fluoro-5-methylphenyl)-N -methylquinoline-4-carboxamide;

1-90: 6-(3-cyano-5-fluorophenyl)-3-(3-fluoro-5-methylphenyl)-N- {[(2S,4S)-4-fluoropyrrolidin -2-yl]methyl}-N-methylquinoline-4-carboxamide;

1-91: 6-(3-fluoro-2-hydroxyphenyl)-3-(3-fluoro-5-methylphenyl)-N-methyl-N-[(2S)-pyrrolidin -2-ylmethyl]quinoline-4-carboxamide.

In some embodiments, provided herein is a pharmaceutically acceptable salt of a compound that is described in Table 1.

TABLE 2

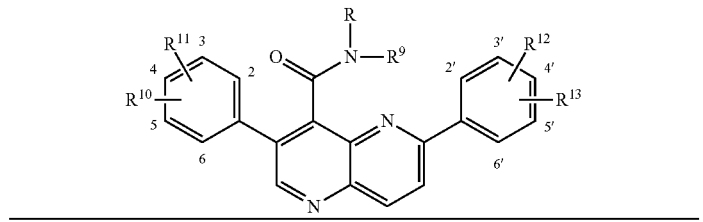

| Cpd No. | R | $R^9$ | $R^{10}$ | $R^{11}$ | $R^{12}$ | $R^{13}$ |
|---|---|---|---|---|---|---|
| 2-1 | 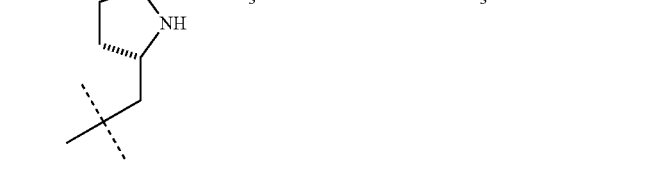 | $CH_3$ | 3-Cl | 5-$CH_3$ | 3'-OH | H |
| 2-2 | 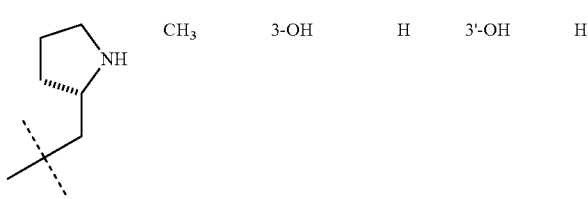 | $CH_3$ | 3-OH | H | 3'-OH | H |

TABLE 2-continued
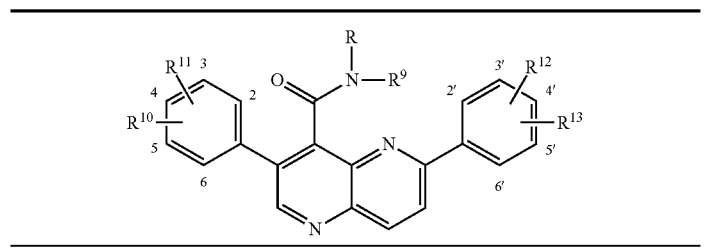
| Cpd No. | R | $R^9$ | $R^{10}$ | $R^{11}$ | $R^{12}$ | $R^{13}$ |
|---|---|---|---|---|---|---|
| 2-3 | pyrrolidinyl-CH2- | $CH_3$ | 3-Cl | 5-$CH_3$ | 3'-OH | 6'-F |
| 2-4 | pyrrolidinyl-CH2- | $CH_3$ | 3-Cl | 5-$CH_3$ | 3'-OH | 5'-CN |
| 2-5 | CH(NH2)-C(CH3)2- | $CH_3$ | 3-$CH_3$ | 5-$CH_3$ | 3'-OH | 5'-CN |
| 2-6 | CH(NH2)-C(CH3)2- | $CH_3$ | 3-Cl | 5-$CH_3$ | 3'-OH | 5'-CN |
| 2-7 | CH(NH2)-C(CH3)2- | $CH_3$ | 3-F | 5-$CH_3$ | 3'-OH | 5'-CN |
| 2-8 | pyrrolidinyl-CH2- | $CH_3$ | 3-(pyrazol-1-yl) | H | 3'-OH | H |
| 2-9 | pyrrolidinyl-CH2- | $CH_3$ | 3-F | 5-F | 3'-OH | H |

TABLE 2-continued
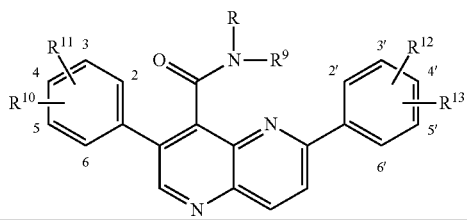
| Cpd No. | R | R⁹ | R¹⁰ | R¹¹ | R¹² | R¹³ |
|---|---|---|---|---|---|---|
| 2-10 | | CH₃ | 3-CH₂CH₂OH | H | 3'-CN | 5'-F |
| 2-11 | | CH₃ | H | H | 3'-CN | 5'-F |
| 2-12 | | CH₃ | 3-MeO | H | 3'-CN | 5'-F |
| 2-13 | | CH₃ | 3-F | H | 3'-CN | 5'-F |
| 2-14 | | CH₃ | 3-CH₂NHAc | H | 3'-CN | 5'-F |
| 2-15 | | CH₃ | 3-CN | H | 3'-CN | 5'-F |
| 2-16 | | CH₃ | 3-F | 5-F | 3'-CN | 5'-F |

TABLE 2-continued
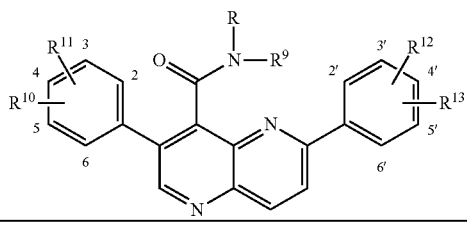
| Cpd No. | R | R⁹ | R¹⁰ | R¹¹ | R¹² | R¹³ |
|---|---|---|---|---|---|---|
| 2-17 | pyrrolidinyl-CH₂- | CH₃ | 3-CH₃ | 5-F | 3'-CN | 5'-F |
| 2-18 | pyrrolidinyl-CH₂- | CH₃ | 3-OMe | 5-F | 3'-CN | 5'-F |
| 2-19 | pyrrolidinyl-CH₂- | CH₃ | 3-F | 5-F | 3'-CN | H |
| 2-20 | pyrrolidinyl-CH₂- | CH₃ | 3-CH₂CO₂H | H | 3'-OH | H |
| 2-21 | pyrrolidinyl-CH₂- | CH₃ | 3-CH₂CO₂Me | H | 3'-OH | H |
| 2-22 | pyrrolidinyl-CH₂- | CH₃ | 3-CH₂—CH₂CO₂H | H | 3'-OH | H |
| 2-23 | pyrrolidinyl-CH₂- | CH₃ | 3-CH₂—CH₂CO₂Me | H | 3'-OH | H |

TABLE 2-continued

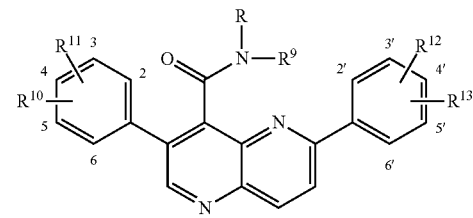

| Cpd No. | R | R⁹ | R¹⁰ | R¹¹ | R¹² | R¹³ |
| --- | --- | --- | --- | --- | --- | --- |
| 2-24 | (2S)-pyrrolidin-2-ylmethyl with neopentyl linker | CH₃ | 3-CH₃ | 5-F | 3'-CONH₂ | 5'-F |

Compounds in Table 2 are named:

2-1: 3-(3-chloro-5-methylphenyl)-6-(3-hydroxyphenyl)-N-methyl-N-[(2S)-pyrrolidin-2-ylmethyl]-1,5-naphthyridine-4-carboxamide;

2-2: 3,6-bis(3-hydroxyphenyl)-N-methyl-N-[(2S)-pyrrolidin-2-ylmethyl]-1,5-naphthyridine-4-carboxamide;

2-3: 3-(3-chloro-5-methylphenyl)-6-(2-fluoro-5-hydroxyphenyl)-N-methyl-N-[(2S)-pyrrolidin -2-ylmethyl]- 1,5-naphthyridine-4-carboxamide;

2-4: 3-(3-chloro-5-methylphenyl)-6-(3-cyano-5-hydroxyphenyl)-N-methyl-N-[(2S)-pyrrolidin -2-ylmethyl]- 1,5-naphthyridine-4-carboxamide;

2-5: N-[(2S)-2-aminobutyl]-6-(3-cyano-5-hydroxyphenyl)-3-(3,5-dimethylphenyl)-N-methyl -1,5-naphthyridine-4-carboxamide;

2-6: N-[(2S)-2-aminobutyl]-3-(3-chloro-5-methylphenyl)-6-(3-cyano-5-hydroxyphenyl)-N -methyl-1,5-naphthyridine-4-carboxamide;

2-7: N-[(2S)-2-aminobutyl]-6-(3-cyano-5-hydroxyphenyl)-3-(3-fluoro-5-methylphenyl)-N -methyl-1,5-naphthyridine-4-carboxamide;

2-8: 6-(3-hydroxyphenyl)-N-methyl-3-[3-(1H-pyrazol-1-yl)phenyl]-N-[(2S)-pyrrolidin-2-ylmethyl]-1,5-naphthyridine-4-carboxamide;

2-9: 3-(3,5-difluorophenyl)-6-(3-hydroxyphenyl)-N-methyl-N-[(2S)-pyrrolidin-2-ylmethyl]-1,5-naphthyridine-4-carboxamide;

2-10: 6-(3-cyano-5-fluorophenyl)-3[3-(2-hydroxyethyl)phenyl]-N-methyl-N-[(2S)-pyrrolidin-2-ylmethyl]-1,5-naphthyridine-4-carboxamide;

2-11: 6-(3-cyano-5-fluorophenyl)-N-methyl-3-phenyl-N-[(2S)-pyrrolidin-2-ylmethyl]-1,5-naphthyridine-4-carboxamide;

2-12: 6-(3-cyano-5-fluorophenyl)-3-(3-methoxyphenyl)-N-methyl-N-[(2S)-pyrrolidin-2-ylmethyl]-1,5-naphthyridine-4-carboxamide;

2-13: 6-(3-cyano-5-fluorophenyl)-3-(3-fluorophenyl)-N-methyl-N-[(2S)-pyrrolidin-2-ylmethyl]-1,5-naphthyridine-4-carboxamide;

2-14: 6-(3-cyano-5-fluorophenyl)-3-[3-(acetamidomethyl)phenyl]-N-methyl-N-[(2S)-pyrrolidin -2-ylmethyl]-1,5-naphthyridine-4-carboxamide;

2-15: 6-(3-cyano-5-fluorophenyl)-3-(3-cyanophenyl)-N-methyl-N-[(2S)-pyrrolidin-2-ylmethyl]-1,5-naphthyridine-4-carboxamide;

2-16: 6-(3-cyano-5-fluorophenyl)-3-(3,5-difluorophenyl)-N-methyl-N-[(2S)-pyrrolidin-2-ylmethyl]-1,5-naphthyridine-4-carboxamide;

2-17: 6-(3-cyano-5-fluorophenyl)-3-(3-fluoro-5-methylphenyl)-N-methyl-N-[(2S)-pyrrolidin-2-ylmethyl]-1,5-naphthyridine-4-carboxamide;

2-18: 6-(3-cyano-5-fluorophenyl)-3-(3-fluoro-5-methoxyphenyl)-N-methyl-N-[(2S)-pyrrolidin -2-ylmethyl]- 1,5-naphthyridine-4-carboxamide;

2-19: 6-(3-cyanophenyl)-3-(3,5-difluorophenyl)-N-methyl-N-[(2S)-pyrrolidin-2-ylmethyl]-1,5-naphthyridine-4-carboxamide;

2-20: 2-{3-[6-(3-hydroxyphenyl)-4-[methyl(pyrrolidin-2-ylmethyl)carbamoyl]-1,5-naphthyridin-3-yl]phenyl}acetic acid;

2-21: methyl 2-{3-[6-(3-hydroxyphenyl)-4-{methyl[(2S)-pyrrolidin-2-ylmethyl]carbamoyl}-1,5-naphthyridin-3-yl]phenyl}acetate;

2-22: 3-{3-[6-(3-hydroxyphenyl)-4-{methyl[(2S)-pyrrolidin-2-ylmethyl]carbamoyl}-1,5-naphthyridin-3-yl]phenyl}propanoic acid;

2-23: methyl 3-{3-[6-(3-hydroxyphenyl)-4-{methyl[(2S)-pyrrolidin-2-ylmethyl]carbamoyl}-1,5-naphthyridin-3-yl]phenyl}propanoate;

2-24: 6-(3-carbamoyl-5-fluorophenyl)-3-(3-fluoro-5-methylphenyl)-N-methyl-N-[(2S) -pyrrolidin-2-ylmethyl]-1,5-naphthyridine-4-carboxamide.

In some embodiments, provided herein is a pharmaceutically acceptable salt of a compound that is described in Table 2.

TABLE 3

| Cpd No. | R | A¹ | R^A | R^B |
|---|---|---|---|---|
| 3-1 | pyrrolidin-2-ylmethyl (NH) | N | H | 3-hydroxyphenyl |
| 3-2 | pyrrolidin-2-ylmethyl (NH) | N | 3-fluoro-5-methylphenyl | pyrrolidin-1-yl |
| 3-3 | pyrrolidin-2-ylmethyl (NH) | N | 3-fluoro-5-methylphenyl | 3-hydroxypiperidin-1-yl |
| 3-4 | pyrrolidin-2-ylmethyl (NH) | N | pyrrolidin-1-yl | 3-hydroxyphenyl |
| 3-5 | pyrrolidin-2-ylmethyl (NH) | N | 6-methylpyridin-2-yl | 3-hydroxyphenyl |
| 3-6 | pyrrolidin-2-ylmethyl (NH) | N | 2,6-dimethylmorpholin-4-yl | 3-hydroxyphenyl |
| 3-6 | pyrrolidin-2-ylmethyl (NH) | N | Cl | 3-hydroxyphenyl |

TABLE 3-continued

| Cpd No. | R | A¹ | R^A | R^B |
|---|---|---|---|---|
| 3-7 | 2-pyrrolidinylmethyl (NH) | N | ethynyl | 3-cyano-5-fluorophenyl |
| 3-8 | 2-pyrrolidinylmethyl (NH) | CH | 3-fluoro-5-methylphenyl | 5-cyanopyridin-3-yl |
| 3-9 | 2-pyrrolidinylmethyl (NH) | N | cyclopent-1-en-1-yl | 3-cyano-5-fluorophenyl |
| 3-10 | 2-pyrrolidinylmethyl (NH) | CH | 3-fluoro-5-methylphenyl | 1-methyl-1H-pyrazol-4-yl |
| 3-11 | 2-pyrrolidinylmethyl (NH) | N | piperidin-1-yl | 3-hydroxyphenyl |
| 3-12 | 2-pyrrolidinylmethyl (NH) | N | morpholin-4-yl | 3-hydroxyphenyl |
| 3-13 | 2-pyrrolidinylmethyl (NH) | CH | 3-fluoro-5-methylphenyl | 6-cyanopyridin-2-yl |

TABLE 3-continued

| Cpd No. | R | A¹ | Rᴬ | Rᴮ |
|---|---|---|---|---|
| 3-14 | (S)-pyrrolidin-2-ylmethyl | CH | 3-fluoro-5-methylphenyl | 4-cyanopyridin-2-yl |
| 3-15 | (S)-pyrrolidin-2-ylmethyl | CH | 3-fluoro-5-methylphenyl | 6-amino-5-cyanopyridin-3-yl |
| 3-16 | (S)-pyrrolidin-2-ylmethyl | CH | 3-fluoro-5-methylphenyl | 2-cyanopyridin-4-yl |
| 3-17 | (S)-pyrrolidin-2-ylmethyl | CH | 3-(hydroxymethyl)pyrrolidin-1-yl | 3-hydroxyphenyl |
| 3-18 | (S)-pyrrolidin-2-ylmethyl | N | prop-1-yn-1-yl | 3-hydroxyphenyl |
| 3-19 | (S)-pyrrolidin-2-ylmethyl | CH | 3-fluoro-5-methylphenyl | 6-cyanopyrimidin-4-yl |
| 3-20 | (S)-pyrrolidin-2-ylmethyl | CH | (2R,6S)-2,6-dimethylmorpholin-4-yl | 3-hydroxyphenyl |

TABLE 3-continued

| Cpd No. | R | A¹ | R^A | R^B |
|---|---|---|---|---|
| 3-21 | pyrrolidine | CH | 2,6-dimethylmorpholine | 3-hydroxyphenyl |
| 3-22 | pyrrolidine | CH | 3-fluoro-5-methylphenyl | 5-cyano-2,4-dimethylpyridin-3-yl |
| 3-33 | pyrrolidine | CH | 3-fluoro-5-methylphenyl | 2-carbamoylpyridin-4-yl |
| 3-34 | pyrrolidine | CH | 2-fluoro-3,5-dimethylphenyl | 3-cyano-5-fluorophenyl |
| 3-35 | pyrrolidine | CH | 3-fluoro-5-methylpyridinyl | 6-carbamoylpyridin-2-yl |
| 3-36 | pyrrolidine | N | 2,6-dimethylmorpholine | 3-cyano-5-fluorophenyl |

TABLE 3-continued

| Cpd No. | R | A¹ | R^A | R^B |
|---|---|---|---|---|
| 3-37 | (S)-pyrrolidin-2-ylmethyl with gem-dimethyl | CH | 3-fluoro-5-methylphenyl | 5-cyano-2-(methylamino)pyridin-3-yl |
| 3-38 | (S)-pyrrolidin-2-ylmethyl with gem-dimethyl | CH | 3-fluoro-5-methylphenyl | 5-cyano-2-(dimethylamino)pyridin-3-yl |
| 3-39 | (S)-pyrrolidin-2-ylmethyl with gem-dimethyl | CH | 3-fluoro-5-methylphenyl | 5-cyano-2-methylpyridin-3-yl |
| 3-40 | (S)-pyrrolidin-2-ylmethyl with gem-dimethyl | CH | 3-fluoro-5-(2-hydroxyethyl)phenyl | 5-cyanopyridin-3-yl |
| 3-41 | (S)-2-aminobutyl with gem-dimethyl | CH | 3-fluoro-5-methylphenyl | 5-cyano-2-(dimethylamino)pyridin-3-yl |
| 3-42 | (S)-pyrrolidin-2-ylmethyl with gem-dimethyl | N | (S)-2-phenylmorpholin-4-yl | 3-cyano-5-fluorophenyl |

TABLE 3-continued

| Cpd No. | R | A¹ | R^A | R^B |
|---|---|---|---|---|
| 3-43 | (S)-pyrrolidinyl-CH₂-C(CH₃)₂- | N | isopentyl | 3-cyano-5-fluorophenyl |
| 3-44 | (S)-pyrrolidinyl-CH₂-C(CH₃)₂- | CH | 3-fluoro-5-methylphenyl | 6-carbamoylpyrazin-2-yl |
| 3-45 | (S)-pyrrolidinyl-CH₂-C(CH₃)₂- | CH | (2S,6R)-2,6-dimethylmorpholin-4-yl | 3-cyano-5-fluorophenyl |
| 3-46 | (S)-pyrrolidinyl-CH₂-C(CH₃)₂- | CH | 3-fluoro-5-methylphenyl | 6-(methylcarbamoyl)pyridin-2-yl |
| 3-47 | (S)-pyrrolidinyl-CH₂-C(CH₃)₂- | N | (2S)-2-phenylmorpholin-4-yl | 3-cyano-5-fluorophenyl |
| 3-48 | (S)-pyrrolidinyl-CH₂-C(CH₃)₂- | CH | 3-fluoro-5-methylphenyl | pyridin-3-yl |

TABLE 3-continued

| Cpd No. | R | A¹ | R^A | R^B |
|---|---|---|---|---|
| 3-49 | pyrrolidine-CH₂- | N | 2,2,6,6-tetramethylmorpholin-4-yl | 3-cyano-5-fluorophenyl |
| 3-50 | pyrrolidine-CH₂- | CH | 3-fluoro-5-methylphenyl | 3-carbamoyl-4,5-difluorophenyl |
| 3-51 | pyrrolidine-CH₂- | CH | 3-fluoro-5-methylphenyl | 6-aminopyridin-2-yl |
| 3-52 | pyrrolidine-CH₂- | CH | 3-fluoro-5-methylphenyl | 3-carbamoyl-2,5-difluorophenyl |
| 3-53 | pyrrolidine-CH₂- | CH | 3-fluoro-5-methylphenyl | 6-methoxypyridin-2-yl |
| 3-54 | pyrrolidine-CH₂- | CH | 6-(trifluoromethyl)indolin-1-yl | 3-cyano-5-fluorophenyl |

TABLE 3-continued

| Cpd No. | R | A¹ | R^A | R^B |
|---|---|---|---|---|
| 3-55 | pyrrolidinyl-CH₂-C(CH₃)₂- | N | 5-(trifluoromethyl)isoindolin-2-yl | 3-cyano-5-fluorophenyl |
| 3-56 | pyrrolidinyl-CH₂-C(CH₃)₂- | CH | 3-fluoro-5-methylphenyl | 5-cyano-2-hydroxypyridin-3-yl |
| 3-57 | pyrrolidinyl-CH₂-C(CH₃)₂- | CH | 3-fluoro-5-methylphenyl | 6-carbamoyl-3-methylpyridin-2-yl |
| 3-58 | pyrrolidinyl-CH₂-C(CH₃)₂- | CH | 3-fluoro-5-(2-hydroxyethyl)phenyl | 5-carbamoylpyridin-3-yl |
| 3-59 | pyrrolidinyl-CH₂-C(CH₃)₂- | CH | 3-fluoro-5-methylphenyl | 5-fluoropyridin-3-yl |
| 3-60 | pyrrolidinyl-CH₂-C(CH₃)₂- | CH | 3-fluoro-5-methylphenyl | 1H-indol-6-yl |

TABLE 3-continued

| Cpd No. | R | A¹ | R^A | R^B |
|---|---|---|---|---|
| 3-61 | pyrrolidin-2-ylmethyl | CH | 3-fluoro-5-methylphenyl | 1H-indol-4-yl |
| 3-62 | pyrrolidin-2-ylmethyl | CH | 3-fluoro-5-methylphenyl | 2-amino-5-fluoropyridin-3-yl |
| 3-64 | pyrrolidin-2-ylmethyl | CH | 2,6-dimethylmorpholin-4-yl | 3-carbamoyl-5-fluorophenyl |
| 3-65 | pyrrolidin-2-ylmethyl | CH | 3-fluoro-5-methylphenyl | 4-methylpyridin-3-yl |
| 3-66 | pyrrolidin-2-ylmethyl | CH | 3-fluoro-5-methylphenyl | 1-oxoisoindolin-4-yl |
| 3-67 | 3-aminopentyl | CH | 3-fluoro-5-methylphenyl | 6-carbamoylpyridin-2-yl |

TABLE 3-continued

| Cpd No. | R | A¹ | R^A | R^B |
|---|---|---|---|---|
| 3-68 | pyrrolidin-2-ylmethyl (NH) | CH | 3-fluoro-5-methylphenyl | 5-chloropyridin-3-yl |
| 3-69 | pyrrolidin-2-ylmethyl (NH) | N | 3-azabicyclo[3.1.0]hexan-3-yl | 3-cyano-5-fluorophenyl |
| 3-70 | pyrrolidin-2-ylmethyl (NH) | N | 8-oxa-3-azabicyclo[3.2.1]octan-3-yl | 3-cyano-5-fluorophenyl |
| 3-71 | pyrrolidin-2-ylmethyl (NH) | CH | 3-fluoro-5-methylphenyl | pyrimidin-5-yl |
| 3-72 | pyrrolidin-2-ylmethyl (NH) | CH | 3-fluoro-5-methylphenyl | 4-cyano-6-morpholinopyridin-2-yl |
| 3-73 | pyrrolidin-2-ylmethyl (NH) | CH | 3-fluoro-5-methylphenyl | 6-(trifluoromethyl)-2-oxo-2,3-dihydro-1H-benzo[d]imidazol-4-yl |

TABLE 3-continued

| Cpd No. | R | A¹ | R^A | R^B |
|---|---|---|---|---|
| 3-74 | pyrrolidin-2-ylmethyl (NH) | CH | 3-fluoro-5-methylphenyl | 4-fluoropyridin-3-yl |
| 3-75 | pyrrolidin-2-ylmethyl (NH) | CH | 3-fluoro-5-methylphenyl | 4-chloropyridin-3-yl |
| 3-76 | pyrrolidin-2-ylmethyl (NH) | N | 3,3-difluoropyrrolidin-1-yl | 3-cyano-5-fluorophenyl |
| 3-77 | pyrrolidin-2-ylmethyl (NH) | CH | 3,5-difluorophenyl | 6-carbamoylpyridin-2-yl |
| 3-78 | pyrrolidin-2-ylmethyl (NH) | CH | 3-fluoro-5-methylphenyl | 6-carbamoyl-3-fluoropyridin-2-yl |
| 3-79 | pyrrolidin-2-ylmethyl (NH) | CH | 3,5-difluorophenyl | 6-carbamoyl-3-methylpyridin-2-yl |

TABLE 3-continued
| Cpd No. | R | A¹ | R^A | R^B |
|---|---|---|---|---|
| 3-80 | 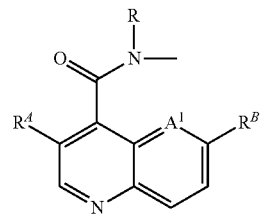 | CH | 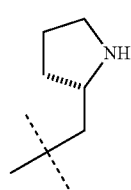 | 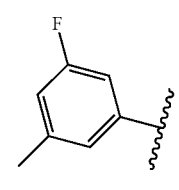 [SMILES: *c1cc(C)cc(F)c1] |
| 3-81 | 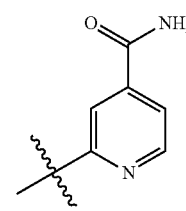 | CH | 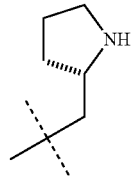 | 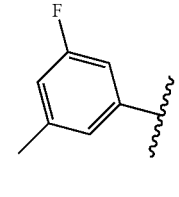 [SMILES: *c1cc(C)cc(F)c1] |
| 3-82 | 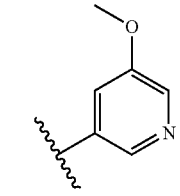 | CH | 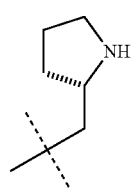 | 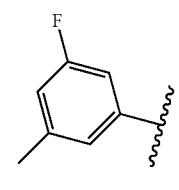 [SMILES: *c1cc(C)cc(F)c1] |
| 3-83 | 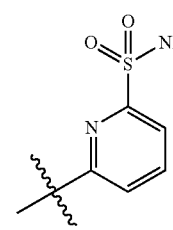 | CH | 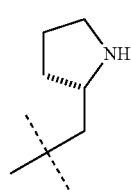 | 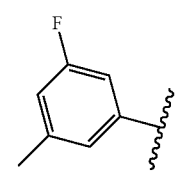 [SMILES: *c1cc(C)cc(F)c1] |
| 3-84 | 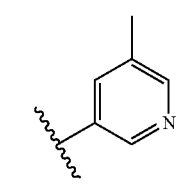 [SMILES: *c1cncc(C)c1] | CH | 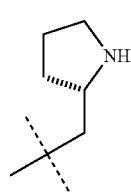 | 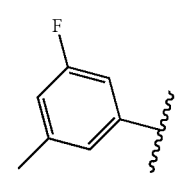 [SMILES: *c1cc(C)cc(F)c1] |
| 3-85 | 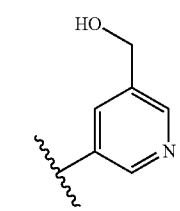 [SMILES: *c1cncc(CO)c1] | CH | 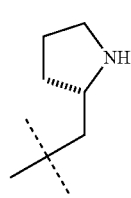 | 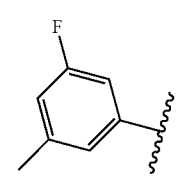 [SMILES: *c1cc(C)cc(F)c1] |

TABLE 3-continued

| Cpd No. | R | A[1] | R[A] | R[B] |
|---|---|---|---|---|
| 3-86 | (S)-pyrrolidin-2-ylmethyl | CH | 3-fluoro-5-methylphenyl | 5-(difluoromethoxy)pyridin-3-yl |
| 3-87 | (S)-1-(ethoxycarbonyl)pyrrolidin-2-ylmethyl | CH | 3,5-difluorophenyl | 6-carbamoylpyridin-2-yl |
| 3-88 | (S)-pyrrolidin-2-ylmethyl | CH | 3-chloro-5-methylphenyl | 6-carbamoylpyridin-2-yl |
| 3-89 | (S)-pyrrolidin-2-ylmethyl | CH | 3-chloro-5-methylphenyl | 6-carbamoyl-3-fluoropyridin-2-yl |
| 3-90 | (S)-pyrrolidin-2-ylmethyl | CH | 3-chloro-5-methylphenyl | 6-carbamoyl-3-methylpyridin-2-yl |
| 3-91 | (S)-pyrrolidin-2-ylmethyl | CH | 3-chloro-5-methylphenyl | 6-carbamoyl-3-chloropyridin-2-yl |

TABLE 3-continued

| Cpd No. | R | A¹ | R⁴ | R^B |
|---|---|---|---|---|
| 3-92 | azetidine-CH₂-C(CH₃)₂- | CH | 3-F-5-Me-phenyl | 6-carbamoylpyridin-2-yl |
| 3-93 | azetidine-CH₂-C(CH₃)₂- | CH | 3-F-5-Me-phenyl | 6-carbamoyl-3-fluoropyridin-2-yl |
| 3-94 | azetidine-CH₂-C(CH₃)₂- | CH | 3-F-5-Me-phenyl | 6-carbamoyl-3-methylpyridin-2-yl |
| 3-95 | azetidine-CH₂-C(CH₃)₂- | CH | 3-F-5-Me-phenyl | 6-carbamoyl-3-chloropyridin-2-yl |
| 3-96 | pyrrolidine-CH₂-C(CH₃)₂- | CH | 3,5-diCl-phenyl | 6-carbamoylpyridin-2-yl |
| 3-97 | pyrrolidine-CH₂-C(CH₃)₂- | CH | 3,5-diCl-phenyl | 6-carbamoyl-3-fluoropyridin-2-yl |

TABLE 3-continued

| Cpd No. | R | A¹ | R^A | R^B |
|---|---|---|---|---|
| 3-98 | (S)-pyrrolidin-2-ylmethyl (neopentyl-linked) | CH | 3,5-dichlorophenyl | 5-methyl-6-carbamoylpyridin-2-yl |
| 3-99 | (S)-pyrrolidin-2-ylmethyl | CH | 3,5-dichlorophenyl | 5-chloro-6-carbamoylpyridin-2-yl |
| 3-100 | (S)-azetidin-2-ylmethyl | CH | 3,5-dichlorophenyl | 6-carbamoylpyridin-2-yl |
| 3-101 | (S)-azetidin-2-ylmethyl | CH | 3,5-dichlorophenyl | 5-fluoro-6-carbamoylpyridin-2-yl |
| 3-102 | (S)-azetidin-2-ylmethyl | CH | 3,5-dichlorophenyl | 5-methyl-6-carbamoylpyridin-2-yl |
| 3-103 | (R)-azetidin-2-ylmethyl | CH | 3,5-dichlorophenyl | 5-chloro-6-carbamoylpyridin-2-yl |

TABLE 3-continued

| Cpd No. | R | A¹ | R^A | R^B |
|---|---|---|---|---|
| 3-104 | (S)-1-methylpyrrolidin-2-ylmethyl | CH | 3-fluoro-5-methylphenyl | 6-carbamoylpyridin-2-yl |
| 3-105 | (S)-pyrrolidin-2-ylmethyl | CH | 3-fluoro-5-methylphenyl | 5-(trifluoromethyl)pyridin-3-yl |
| 3-106 | (S)-pyrrolidin-2-ylmethyl | CH | 3-fluoro-5-methylphenyl | 4-oxo-3,4-dihydro-2H-benzo[e][1,3]oxazin-6-yl |
| 3-107 | (S)-pyrrolidin-2-ylmethyl | CH | 3-fluoro-5-methylphenyl | 3,5-difluoro-2-hydroxyphenyl |

Compounds in Table 3 are named:

3-1: 6-(3-hydroxyphenyl)-N-methyl-N-[(2S)-pyrrolidin-2-ylmethyl]-1,5-naphthyridine-4-carboxamide;

3-2: 3-(3-fluoro-5-methylphenyl)-N-methyl-6-(pyrrolidin-1-yl)-N-[(2S)-pyrrolidin-2-ylmethyl]-1,5-naphthyridine-4-carboxamide;

3-3: 3-(3-fluoro-5-methylphenyl)-6-(3-hydroxypiperidin-1-yl)-N-methyl-N-[(2S)-pyrrolidin-2-ylmethyl]-1,5-naphthyridine-4-carboxamide;

3-4: 6-(3-hydroxyphenyl)-N-methyl-3-(pyrrolidin-1-yl)-N-[(2S)-pyrrolidin-2-ylmethyl]-1,5-naphthyridine-4-carboxamide;

3-5: 6-(3-hydroxyphenyl)-N-methyl-3-(6-methylpyridin-2-yl)-N-[(2S)-pyrrolidin-2-ylmethyl]-1,5-naphthyridine-4-carboxamide;

3-6: 3-(2,6-dimethylmorpholin-4-yl)-6-(3-hydroxyphenyl)-N-methyl-N-[(2S)-pyrrolidin-2-ylmethyl]-1,5-naphthyridine-4-carboxamide;

3-7: 6-(3-cyano-5-fluorophenyl)-N-methyl-3-(prop-1-yn-1-yl)-N-[(2S)-pyrrolidin-2-ylmethyl]-1,5-naphthyridine-4-carboxamide;

3-8: 6-(5-cyanopyridin-3-yl)-3-(3-fluoro-5-methylphenyl)-N-methyl-N-[(2S)-pyrrolidin-2-ylmethyl]quinoline-4-carboxamide;

3-9: 6-(3-cyano-5-fluorophenyl)-3-(cyclopent-1-en-1-yl)-N-methyl-N-[(2S)-pyrrolidin-2-ylmethyl]-1,5-naphthyridine-4-carboxamide;

3-10: 3-(3-fluoro-5-methylphenyl)-N-methyl-6-(1-methyl-1H-pyrazol-4-yl)-N-[(2S)-pyrrolidin-2-ylmethyl]quinoline-4-carboxamide;

3-11: 6-(3-hydroxyphenyl)-N-methyl-3-(piperidin-1-yl)-N-[(2S)-pyrroldin-2-ylmethyl]-1,5-naphthyridine-4-carboxamide;

3-12: 6-(3-hydroxyphenyl)-N-methyl-3-(morpholin-4-yl)-N-[(2S)-pyrrolidin-2-ylmethyl]-1,5-naphthyridine-4-carboxamide;

3-13: 6-(6-cyanopyridin-2-yl)-3-(3-fluoro-5-methylphenyl)-N-methyl-N-[(2S)-pyrrolidin-2-ylmethyl]quinoline-4-carboxamide;

3-14: 6-(4-cyanopyridin-2-yl)-3-(3-fluoro-5-methylphenyl)-N-methyl-N-[(2S)-pyrrolidin-2-ylmethyl]quinoline-4-carboxamide;

3-15: 6-(2-amino-5-cyanopyridin-3-yl)-3-(3-fluoro-5-methylphenyl)-N-methyl-N-[(2S)-pyrrolidin-2-ylmethyl]quinoline-4-carboxamide;

3-16: 6-(2-cyanopyridin-4-yl)-3-(3-fluoro-5-methylphenyl)-N-methyl-N-[(2S)-pyrrolidin-2-ylmethyl]quinoline-4-carboxamide;

3-17: 3-[3-(hydroxymethyl)pyrrolidin-1-yl]-6-(3-hydroxyphenyl)-N-methyl-N-[(2S)-pyrrolidin-2-ylmethyl]-1,5-naphthyridine-4-carboxamide;

3-18: 6-(3-hydroxyphenyl)-N-methyl-3-(prop-1-yn-1-yl)-N-((2S)-pyrrolidin-2-ylmethyl)-1,5-naphthyridine-4-carboxamide;

3-19: 6-(4-cyanopyrimidin-2-yl-3-(3-fluoro-5-methylphenyl)-N-methyl-N-[(2S)-pyrrolidin-2-ylmethyl]quinoline-4-carboxamide;

3-20: 3-(cis-2,6-dimethylmorpholin-4-yl)-6-(3-hydroxyphenyl)-N-methyl-N-[(2S)-pyrrolidin-2-ylmethyl]quinoline-4-carboxamide;

3-21: 3-(trans-2,6-dimethylmorpholin-4-yl-6-(3-hydroxyphenyl)-N-methyl-N-[(2S)-pyrrolidin-2-ylmethyl]quinoline-4-carboxamide;

3-22: 6-(5-cyano-2,4-dimethylpyridin-3-yl)-3-(3-fluoro-5-methylphenyl)-N-methyl-N-[(2S)-pyrrolidin-2-ylmethyl]quinoline-4-carboxamide;

3-33: 6-(2-carbamoylpyridin-4-yl)-3-(3-fluoro-5-methylphenyl)-N-methyl-N-[(2S)-pyrrolidin-2-ylmethyl]quinoline-4-carboxamide;

3-34: 6-(3-cyano-5-fluorophenyl)-3-(2-fluoro-3,5-dimethylphenyl)-N-methyl-N-[(2S)-pyrrolidin-2-ylmethyl]quinoline-4-carboxamide;

3-35: 6-(3-cyano-5-fluorophenyl)-3-(2,6-dimethylmorpholin-4-yl)-N-methyl-N-[(2S)-pyrrolidin-2-ylmethyl]-1,5-naphthyridine-4-carboxamide;

3-36: 6-(3-cyano-5-fluorophenyl)-3-(2,6-dimethylmorpholin-4-yl)-N-methyl-N-[(2S)-pyrrolidin-2-ylmethyl]-1,5-naphthyridine-4-carboxamide;

3-37: 6-[5-cyano-2-(methylamino)pyridin-3-yl]-3-(3-fluoro-5-methylphenyl)-N-methyl-N-[(2S)-pyrrolidin-2-ylmethyl]quinoline-4-carboxamide;

3-38: 6-[5-cyano-2-(dimethylamino)pyridin-3-yl]-3-(3-fluoro-5-methylphenyl)-N-methyl-N-[(2S)-pyrrolidin-2-ylmethyl]quinoline-4-carboxamide;

3-39: 6-(5-cyano-2-methylpyridin-3-yl)-3-(3-fluoro-5-methylphenyl)-N-methyl-N-[(2S)-pyrrolidin-2-ylmethyl]quinoline-4-carboxamide;

3-40: 6-(5-cyanopyridin-3-yl)-3-[3-fluoro-5-(2-hydroxyethyl)phenyl]-N-methyl-N-[(2S)-pyrrolidin-2-ylmethyl]quinoline-4-carboxamide;

3-41: N-[(2S)-2-aminobutyl]-6-[5-cyano-2-(dimethylamino)pyridin-3-yl]-3-(3-fluoro-5-methylphenyl)-N-methylquinoline-4-carboxamide;

3-42: 6-(3-cyano-5-fluorophenyl)-N-methyl-3-[(2R)-2-phenylmorpholin-4-yl]-N-[(2S)-pyrrolidin-2-ylmethyl]-1,5-naphthyridine-4-carboxamide;

3-43: 6-(3-cyano-5-fluorophenyl)-N-methyl-3-(3-methylbutyl)-N-[(2S)-pyrrolidin-2-ylmethyl]-1,5-naphthyridine-4-carboxamide;

3-44: 6-(6-carbamoylpyrazin-2-yl)-3-(3-fluoro-5-methylphenyl)-N-methyl-N-[(2S)-pyrrolidin-2-ylmethyl]quinoline-4-carboxamide;

3-45: 6-(3-cyano-5-fluorophenyl)-3-(2,6-dimethylmorpholin-4-yl)-N-methyl-N-[(2S)-pyrrolidin-2-ylmethyl]quinoline-4-carboxamide;

3-46: 3-(3-fluoro-5-methylphenyl)-N-methyl-6-[6-(methylcarbamoyl)pyridin-2-yl]-N-[(2S)-pyrrolidin-2-ylmethyl]quinoline-4-carboxamide;

3-47: 6-(3-cyano-5-fluorophenyl)-N-methyl-3-[(2S)-2-phenylmorpholin-4-yl]-N-[(2S)-pyrrolidin-2-ylmethyl]-1,5-naphthyridine-4-carboxamide;

3-48: 3-(3-fluoro-5-methylphenyl)-N-methyl-6-(pyridin-3-yl)-N-[(2S)-pyrrolidin-2-ylmethyl]quinoline-4-carboxamide;

3-49: 6-(3-cyano-5-fluorophenyl)-N-methyl-N-[(2S)-pyrrolidin-2-ylmethyl]-3-(2,2,6,6-tetramethylmorpholin-4-yl)-1,5-naphthyridine-4-carboxamide;

3-50: 6-(3-carbamoyl-4,5-difluorophenyl)-3-(3-fluoro-5-methylphenyl)-N-methyl-N-[(2S)-pyrrolidin-2-ylmethyl]quinoline-4-carboxamide;

3-51: 6-(6-aminopyridin-2-yl)-3-(3-fluoro-5-methylphenyl)-N-methyl-N-[(2S)-pyrrolidin-2-ylmethyl]quinoline-4-carboxamide;

3-52: 6-(3-carbamoyl-2,5-difluorophenyl)-3-(3-fluoro-5-methylphenyl)-N-methyl-N-[(2S)-pyrrolidin-2-ylmethyl]quinoline-4-carboxamide;

3-53: 3-(3-fluoro-5-methylphenyl)-6-(6-methoxypyridin-2-yl)-N-methyl-N-[(2S)-pyrrolidin-2-ylmethyl]quinoline-4-carboxamide;

3-54: 6-(3-cyano-5-fluorophenyl)-N-methyl-N-[(2S)-pyrrolidin-2-ylmethyl]-3-[5-(trifluoromethyl)-2,3-dihydro-1H-indol-1-yl]-1,5-naphthyridine-4-carboxamide;

3-55: 6-(3-cyano-5-fluorophenyl)-N-methyl-N-[(2S)-pyrrolidin-2-ylmethyl]-3-[5-(trifluoromethyl)-2,3-dihydro-1H-isoindol-2-yl]-1,5-naphthyridine-4-carboxamide;

3-56: 6-(5-cyano-2-hydroxypyridin-3-yl)-3-(3-fluoro-5-methylphenyl)-N-methyl-N-[(2S)-pyrrolidin-2-ylmethyl]quinoline-4-carboxamide;

3-57: 6-(6-carbamoyl-3-methylpyridin-2-yl)-3-(3-fluoro-5-methylphenyl)-N-methyl-N-[(2S)-pyrrolidin-2-ylmethyl]quinoline-4-carboxamide;

3-58: 6-(5-carbamoylpyridin-3-yl)-3-[3-fluoro-5-(2-hydroxyethyl)phenyl]-N-methyl-N-[(2S)-pyrrolidin-2-ylmethyl]quinoline-4-carboxamide;

3-59: 3-(3-fluoro-5-methylphenyl)-6-(5-fluoropyridin-3-yl)-N-methyl-N-[(2S)-pyrrolidin-2-ylmethyl]quinoline-4-carboxamide;

3-60: 3-(3-fluoro-5-methylphenyl)-6-(1H-indol-6-yl)-N-methyl-N-[(2S)-pyrrolidin-2-ylmethyl]quinoline-4-carboxamide;

3-61: 3-(3-fluoro-5-methylphenyl)-6-(1H-indol-4-yl)-N-methyl-N-[(2S)-pyrrolidin-2-ylmethyl]quinoline-4-carboxamide;

3-62: 6-(2-amino-5-fluoropyridin-3-yl)-3-(3-fluoro-5-methylphenyl)-N-methyl-N-[(2S)-pyrrolidin-2-ylmethyl]quinoline-4-carboxamide;

3-64: 6-(3-carbamoyl-5-fluorophenyl)-3-[(cis)-2,6-dimethylmorpholin-4-yl]-N-methyl-N-[(2S)-pyrrolidin-2-ylmethyl]quinoline-4-carboxamide;

3-65: 3-(3-fluoro-5-methylphenyl)-N-methyl-6-(4-methylpyridin-3-yl)-N-[(2S)-pyrrolidin-2-ylmethyl]quinoline-4-carboxamide;

3-66: 3-(3-fluoro-5-methylphenyl)-N-methyl-6-(1-oxo-2,3-dihydro-1H-isoindol-4-yl)-N-[(2S)-pyrrolidin-2-ylmethyl]quinoline-4-carboxamide;

3-67: N-[(2S)-2-aminobutyl]-6-(6-carbamoylpyridin-2-yl)-3-(3-fluoro-5-methylphenyl)-N-methylquinoline-4-carboxamide;

3-68: 6-(5-chloropyridin-3-yl)-3-(3-fluoro-5-methylphenyl)-N-methyl-N-[(2S)-pyrrolidin-2-ylmethyl]quinoline-4-carboxamide;

3-69: 3-{3-azabicyclo[3.1.0]hexan-3-yl}-6-(3-cyano-5-fluorophenyl)-N-methyl-N-[(2S)-pyrrolidin-2-ylmethyl]-1,5-naphthyridine-4-carboxamide;

3-70: 6-(3-cyano-5-fluorophenyl)-N-methyl-3-{8-oxa-3-azabicyclo[3.2.1]octan-3-yl}-N-[(2S) -pyrrolidin-2-ylmethyl]-1,5-naphthyridine-4-carboxamide;

3-71: 3-(3-fluoro-5-methylphenyl)-N-methyl-6-(pyrimidin-5-yl)-N-[(2S)-pyrrolidin-2-ylmethyl]quinoline-4-carboxamide;

3-72: 6-[4-cyano-6-(morpholin-4-yl)pyridin-2-yl]-3-(3-fluoro-5-methylphenyl)-N-methyl-N -[(2S)-pyrrolidin-2-ylmethyl]quinoline-4-carboxamide;

3-73: 3-(3-fluoro-5-methylphenyl)-N-methyl-6-[2-oxo-6-(trifluoromethyl)-2,3-dihydro-1H-1,3-benzodiazol-4-yl]-N-[(2S)-pyrrolidin-2-ylmethyl]quinoline-4-carboxamide;

3-74: 3-(3-fluoro-5-methylphenyl)-6-(4-fluoropyridin-3-yl)-N-methyl-N-[(2S)-pyrrolidin-2-ylmethyl]quinoline-4-carboxamide;

3-75: 6-(4-chloropyridin-3-yl)-3-(3-fluoro-5-methylphenyl)-N-methyl-N-[(2S)-pyrrolidin-2-ylmethyl]quinoline-4-carboxamide;

3-76: 6-(3-cyano-5-fluorophenyl)-3-(3,3-difluoropyrrolidin-1-yl)-N-methyl-N-[(2S)-pyrrolidin -2-ylmethyl]-1,5-naphthyridine-4-carboxamide;

3-77: 6-(6-carbamoylpyridin-2-yl)-3-(3,5-difluorophenyl)-N-methyl-N-[(2S)-pyrrolidin-2-ylmethyl]quinoline-4-carboxamide;

3-78: 6-(6-carbamoyl-3-fluoropyridin-2-yl)-3-(3-fluoro-5-methylphenyl)-N-methyl-N-[(2S) -pyrrolidin-2-ylmethyl] quinoline-4-carboxamide;

3-79: 6-(6-carbamoyl-3-methylpyridin-2-yl)-3-(3,5-difluorophenyl)-N-methyl-N-[(2S) -pyrrolidin-2-ylmethyl]quinoline-4-carboxamide;

3-80: 6-(4-carbamoylpyridin-2-yl)-3-(3-fluoro-5-methylphenyl)-N-methyl-N-[(2S)-pyrrolidin -2-ylmethyl]quinoline-4-carboxamide;

3-81: 3-(3-fluoro-5-methylphenyl)-6-(5-methoxypyridin-3-yl)-N-methyl-N-[(2S)-pyrrolidin-2-ylmethyl]quinoline-4-carboxamide;

3-82: 3-(3-fluoro-5-methylphenyl)-N-methyl-N-[(2S)-pyrrolidin-2-ylmethyl]-6-(6-sulfamoylpyridin-2-yl)quinoline-4-carboxamide;

3-83: 3-(3-fluoro-5-methylphenyl)-N-methyl-6-(5-methylpyridin-3-yl)-N-[(2S)-pyrrolidin-2-ylmethyl]quinoline-4-carboxamide;

3-84: 3-(3-fluoro-5-methylphenyl)-6-[5-(hydroxymethyl)pyridin-3-yl]-N-methyl-N-[(2S) -pyrrolidin-2-ylmethyl]quinoline-4-carboxamide;

3-85: 3-(3-chloro-5-methylphenyl)-6-(5-hydroxypyridin-3-yl)-N,7-dimethyl-N-[(2S)-pyrrolidin -2-ylmethyl]-3,4-dihydroquinazoline-4-carboxamide;

3-86: 6-[5-(difluoromethoxy)pyridin-3-yl]-3-(3-fluoro-5-methylphenyl)-N-methyl-N-[(2S) -pyrrolidin-2-ylmethyl]quinoline-4-carboxamide;

3-87: ethyl (2S)-2-({1-[6-(6-carbamoylpyridin-2-yl)-3-(3-fluoro-5-methylphenyl)quinolin-4-yl]-N-methylformamido}methyl)pyrrolidine-1-carboxylate;

3-88: 6-(6-carbamoylpyridin-2-yl)-3-(3-chloro-5-methylphenyl)-N-methyl-N-[(2S)-pyrrolidin-2-ylmethyl]quinoline-4-carboxamide;

3-89: 6-(6-carbamoyl-3-fluoropyridin-2-yl)-3-(3-chloro-5-methylphenyl)-N-methyl-N-[(2S) -pyrrolidin-2-ylmethyl]quinoline-4-carboxamide;

3-90: 6-(6-carbamoyl-3-methylpyridin-2-yl)-3-(3-chloro-5-methylphenyl)-N-methyl-N-[(2S) -pyrrolidin-2-ylmethyl]quinoline-4-carboxamide;

3-91: 6-(6-carbamoyl-3-chloropyridin-2-yl)-3-(3-chloro-5-methylphenyl)-N-methyl-N-[(2S) -pyrrolidin-2-ylmethyl]quinoline-4-carboxamide;

3-92: N-[(2S)-azetidin-2-ylmethyl]-6-(6-carbamoylpyridin-2-yl)-3-(3-fluoro-5-methylphenyl) -N-methylquinoline-4-carboxamide;

3-93: N-[(2S)-azetidin-2-ylmethyl]-6-(6-carbamoyl-3-fluoropyridin-2-yl)-3-(3-fluoro-5-methylphenyl)-N-methylquinoline-4-carboxamide;

3-94: N-[(2S)-azetidin-2-ylmethyl]-6-(6-carbamoyl-3-methylpyridin-2-yl)-3-(3-fluoro-5-methylphenyl)-N-methylquinoline-4-carboxamide;

3-95: N-[(2S)-azetidin-2-ylmethyl]-6-(6-carbamoyl-3-chloropyridin-2-yl)-3-(3-fluoro-5-methylphenyl)-N-methylquinoline-4-carboxamide;

3-96: 6-(6-carbamoylpyridin-2-yl)-3-(3,5-dichlorophenyl)-N-methyl-N-[(2S)-pyrrolidin-2-ylmethyl]quinoline-4-carboxamide;

3-97: 6-(6-carbamoyl-3-fluoropyridin-2-yl)-3-(3,5-dichlorophenyl)-N-methyl-N-[(2S) -pyrrolidin-2-ylmethyl]quinoline-4-carboxamide;

3-98: 6-(6-carbamoyl-3-methylpyridin-2-yl)-3-(3,5-dichlorophenyl)-N-methyl-N-[(2S) -pyrrolidin-2-ylmethyl]quinoline-4-carboxamide;

3-99: 6-(6-carbamoyl-3-chloropyridin-2-yl)-3-(3,5-dichlorophenyl)-N-methyl-N-[(2S) -pyrrolidin-2-ylmethyl]quinoline-4-carboxamide;

3-100: N-[(2S)-azetidin-2-ylmethyl]-6-(6-carbamoylpyridin-2-yl)-3-(3,5-dichlorophenyl)-N -methylquinoline-4-carboxamide;

3-101: N-[(2S)-azetidin-2-ylmethyl]-6-(6-carbamoyl-3-fluoropyridin-2-yl)-3-(3,5-dichlorophenyl)-N-methylquinoline-4-carboxamide;

3-102: N-[(2S)-azetidin-2-ylmethyl]-6-(6-carbamoyl-3-methylpyridin-2-yl)-3-(3,5-dichlorophenyl)-N-methylquinoline-4-carboxamide;

3-103: N-[(2S)-azetidin-2-ylmethyl]-6-(6-carbamoyl-3-chloropyridin-2-yl)-3-(3,5-dichlorophenyl)-N-methylquinoline-4-carboxamide;

3-104: 6-(6-carbamoylpyridin-2-yl)-3-(3-fluoro-5-methylphenyl)-N-methyl-N-{[(2S)-1-methylpyrrolidin-2-yl]methyl}quinoline-4-carboxamide;

3-105: 3-(3-fluoro-5-methylphenyl)-N-methyl-N-[(2S)-pyrrolidin-2-ylmethyl]-6-[5-(trifluoromethyl)pyridin-3-yl]quinoline-4-carboxamide;

3-106: 3-(3-fluoro-5-methylphenyl)-N-methyl-6-(4-oxo-3,4-dihydro-2H-1,3-benzoxazin-6-yl) -N-[(2S)-pyrrolidin-2-ylmethyl]quinoline-4-carboxamide;

3-107: 6-(3,5-difluoro-2-hydroxyphenyl)-3-(3-fluoro-5-methylphenyl)-N-methyl-N-[(2S) -pyrrolidin-2-ylmethyl]quinoline-4-carboxamide.

In some embodiments, provided herein is a pharmaceutically acceptable salt of a compound that is described in Table 3.

In one aspect, compounds described herein are in the form of pharmaceutically acceptable salts. As well, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

"Pharmaceutically acceptable," as used herein, refers a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19. P. H. Stahl and C. G. Wermuth, editors, *Handbook of Pharmaceutical Salts: Properties, Selection and Use*, Weinheim/Zürich: Wiley-VCH/VHCA, 2002. Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible and this capability can be manipulated as one aspect of delayed and sustained release behaviours. Also, because the salt-forming molecule can be in equilibrium with a neutral form, passage through biological membranes can be adjusted.

In some embodiments, pharmaceutically acceptable salts are obtained by reacting a compound of Formula (I) with an acid. In some embodiments, the compound of Formula (I) (i.e. free base form) is basic and is reacted with an organic acid or an inorganic acid. Inorganic acids include, but are not limited to, hydrochloric acid, hydrobromic acid, sulfuric acid, phosphoric acid, nitric acid, and metaphosphoric acid. Organic acids include, but are not limited to, 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; isobutyric acid; lactic acid (DL); lactobionic acid; lauric acid; maleic acid; malic acid (−L); malonic acid; mandelic acid (DL); methanesulfonic acid; naphthalene-1,5-disulfonic acid; naphthalene-2-sulfonic acid; nicotinic acid; oleic acid; oxalic acid; palmitic acid; pamoic acid; phosphoric acid; proprionic acid; pyroglutamic acid (−L); salicylic acid; sebacic acid; stearic acid; succinic acid; sulfuric acid; tartaric acid (+L); thiocyanic acid; toluenesulfonic acid (p); and undecylenic acid.

In some embodiments, a compound of Formula (I) is prepared as a chloride salt, sulfate salt, bromide salt, mesylate salt, maleate salt, citrate salt or phosphate salt.

In some embodiments, pharmaceutically acceptable salts are obtained by reacting a compound of Formula (I) with a base. In some embodiments, the compound of Formula (I) is acidic and is reacted with a base. In such situations, an acidic proton of the compound of Formula (I) is replaced by a metal ion, e.g., lithium, sodium, potassium, magnesium, calcium, or an aluminum ion. In some cases, compounds described herein coordinate with an organic base, such as, but not limited to, ethanolamine, diethanolamine, triethanolamine, tromethamine, meglumine, N-methylglucamine, dicyclohexylamine, tris(hydroxymethyl)methylamine. In other cases, compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, potassium carbonate, sodium hydroxide, lithium hydroxide, and the like. In some embodiments, the compounds provided herein are prepared as a sodium salt, calcium salt, potassium salt, magnesium salt, meglumine salt, N-methylglucamine salt or ammonium salt.

It should be understood that a reference to a pharmaceutically acceptable salt includes the solvent addition forms. In some embodiments, solvates contain either stoichiometric or non-stoichiometric amounts of a solvent, and are formed during the process of crystallization with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

The methods and formulations described herein include the use of N-oxides (if appropriate), or pharmaceutically acceptable salts of compounds having the structure of Formula (I), as well as active metabolites of these compounds having the same type of activity.

In some embodiments, sites on the organic radicals (e.g. alkyl groups, aromatic rings) of compounds of Formula (I) are susceptible to various metabolic reactions. Incorporation of appropriate substituents on the organic radicals will reduce, minimize or eliminate this metabolic pathway. In specific embodiments, the appropriate substituent to decrease or eliminate the susceptibility of the aromatic ring to metabolic reactions is, by way of example only, a halogen, deuterium, an alkyl group, a haloalkyl group, or a deuteroalkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, sulfur, fluorine chlorine, iodine, phosphorus, such as, for example, $^{2}H$, $^{3}H$, $^{13}C$, $^{14}C$, $^{15}N$, $^{18}O$, $^{17}O$, $^{35}S$, $^{18}F$, $^{36}Cl$, $^{123}I$, $^{124}I$, $^{125}I$, $^{131}I$, $^{32}P$ and $^{33}P$. In one aspect, isotopically-labeled compounds described herein, for example those into which radioactive isotopes such as $^{3}H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

In some embodiments, the compounds of Formula (I) possess one or more stereocenters and each stereocenter exists independently in either the R or S configuration. In some embodiments, the compound of Formula (I) exists in the R configuration. In some embodiments, the compound of Formula (I) exists in the S configuration. The compounds presented herein include all diastereomeric, individual enantiomers, atropisomers, and epimeric forms as well as the appropriate mixtures thereof. The compounds and methods provided herein include all cis, trans, syn, anti, entgegen (E), and zusammen (Z) isomers as well as the appropriate mixtures thereof Individual stereoisomers are obtained, if desired, by methods such as, stereoselective synthesis and/or the separation of stereoisomers by chiral chromatographic columns or the separation of diastereomers by either non-chiral or chiral chromatographic columns or crystallization and recrystallization in a proper solvent or a mixture of solvents. In certain embodiments, compounds of Formula (I) are prepared as their individual stereoisomers by reacting a racemic mixture of the compound with an optically active resolving agent to form a pair of diastereoisomeric compounds/salts, separating the diastereomers and recovering the optically pure individual enantiomers. In some embodiments, resolution of individual enantiomers is carried out using covalent diastereomeric derivatives of the compounds described herein. In another embodiment, diastereomers are separated by separation/resolution techniques based upon differences in solubility. In other embodiments, separation of steroisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In some embodiments, stereoisomers are obtained by stereoselective synthesis.

In some embodiments, compounds described herein are prepared as prodrugs. A "prodrug" refers to an agent that is converted into the parent drug in vivo. Prodrugs are often useful because, in some situations, they are easier to administer than the parent drug. They are, for instance, bioavailable by oral administration whereas the parent is not. Further or alternatively, the prodrug also has improved solubility in pharmaceutical compositions over the parent drug. In some embodiments, the design of a prodrug increases the effective water solubility. An example, without limitation, of a prodrug is a compound described herein, which is administered as an ester (the "prodrug") but then is metabolically hydrolyzed to provide the active entity. A further example of a prodrug is a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

Prodrugs of the compounds described herein include, but are not limited to, esters, ethers, carbonates, thiocarbonates, N-acyl derivatives, N-acyloxyalkyl derivatives, N-alkyloxyacyl derivatives, quaternary derivatives of tertiary amines, N-Mannich bases, Schiff bases, amino acid conjugates, phosphate esters, and sulfonate esters. See for example Design of Prodrugs, Bundgaard, A. Ed., Elseview, 1985 and Method in Enzymology, Widder, K. et al., Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, p. 113-191; and Bundgaard, H., Advanced Drug Delivery Review, 1992, 8, 1-38, each of which is incorporated herein by reference. In some embodiments, a hydroxyl group in the compounds disclosed herein is used to form a prodrug, wherein the hydroxyl group is incorporated into an acyloxyalkyl ester, alkoxycarbonyloxyalkyl ester, alkyl ester, aryl ester, phosphate ester, sugar ester, ether, and the like. In some embodiments, a hydroxyl group in the compounds disclosed herein is a prodrug wherein the hydroxyl is then metabolized in vivo to provide a carboxylic acid group. In some embodiments, a carboxyl group is used to provide an ester or amide (i.e. the prodrug), which is then metabolized in vivo to provide a carboxylic acid group. In some embodiments, compounds described herein are prepared as alkyl ester prodrugs.

Prodrug forms of the herein described compounds, wherein the prodrug is metabolized in vivo to produce a compound of Formula (I) as set forth herein are included within the scope of the claims. In some cases, some of the herein-described compounds is a prodrug for another derivative or active compound.

In some embodiments, any one of the hydroxyl group(s), amino group(s) and/or carboxylic acid group(s) are functionalized in a suitable manner to provide a prodrug moiety. In some embodiments, the prodrug moiety is as described above.

In additional or further embodiments, the compounds described herein are metabolized upon administration to an organism in need to produce a metabolite that is then used to produce a desired effect, including a desired therapeutic effect.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

Synthesis of Compounds

Compounds of Formula (I) described herein are synthesized using standard synthetic techniques or using methods known in the art in combination with methods described herein.

Unless otherwise indicated, conventional methods of mass spectroscopy, NMR, HPLC, protein chemistry, biochemistry, recombinant DNA techniques and pharmacology are employed.

Compounds are prepared using standard organic chemistry techniques such as those described in, for example, March's Advanced Organic Chemistry, 6$^{th}$ Edition, John Wiley and Sons, Inc. Alternative reaction conditions for the synthetic transformations described herein may be employed such as variation of solvent, reaction temperature, reaction time, as well as different chemical reagents and other reaction conditions.

In some embodiments, compounds described herein are prepared as described in Scheme A.

Scheme A

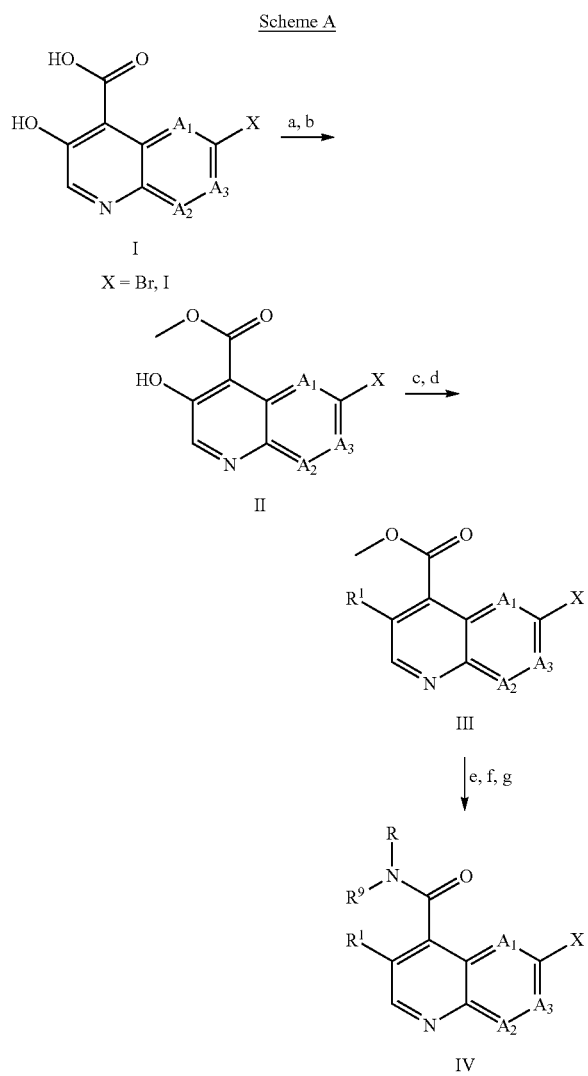

a: MeOH, H$_2$SO$_4$
b: R$^2$B(OH)$_2$, Pd
c: Tf$_2$O, Et$_3$N
d: R$^1$B(OH)$_2$, Pd
e: LiOH, water, THF
f: RR$^9$NH, HATU
g: deprotection Compound I is reacted with an alcohol such as methanol in the presence of a strong acid such as sulfuric acid to form ester and is followed by an organometallic coupling reaction such as Suzuki-Miyaura reaction with R$^2$B(OH)$_2$ leads to formation of compound II. Formation of the triflate on compound II, followed by another organometallic coupling reaction such as Suzuki-Miyaura reaction with R$^1$B(OH)$_2$ yields compound III. Hydrolysis of the ester under basic condition gives rise to the acid which is coupled with the mono-protected diamine (RR$^9$NH, where R containing a protected amino group), in the presence of a coupling reagent such as HATU, and subsquent removal of all protecting groups using appropriate deprotection methods such as acid, yields the compound IV.

In some other embodiments, the intermediate III is synthesized as outlined in Scheme B.

Scheme B

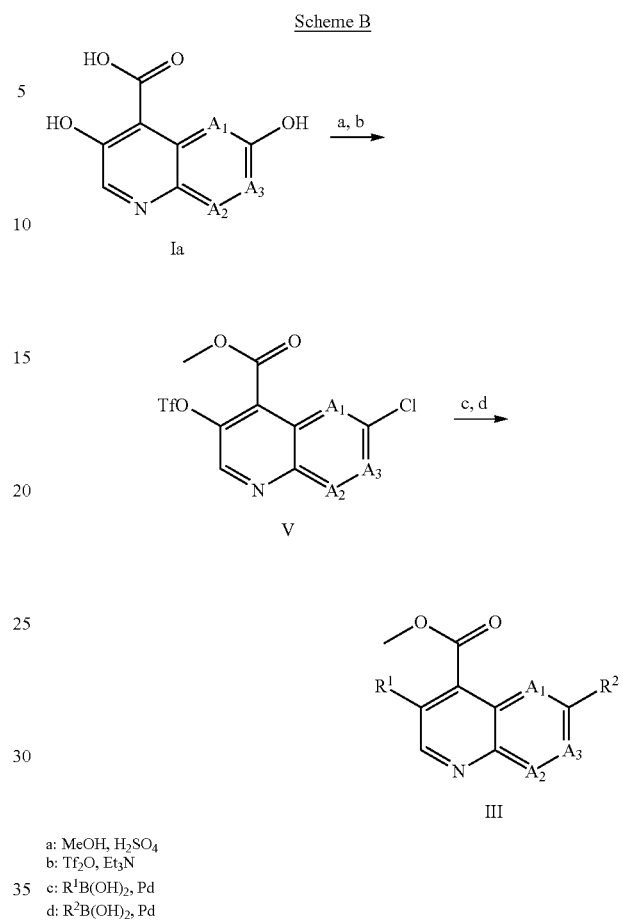

a: MeOH, H$_2$SO$_4$
b: Tf$_2$O, Et$_3$N
c: R$^1$B(OH)$_2$, Pd
d: R$^2$B(OH)$_2$, Pd

Compound Ia is reacted with an alcohol such as methanol in the presence of a strong acid such as sulfuric acid to form ester and is followed by formation of the triflate to produce V. Two consecutive but selective Suzuki-Miyaura reactions with R$^1$B(OH)$_2$ and R$^2$B(OH)$_2$ leads to formation of compound III.

Intermediate IIIb is synthesized as outlined in Scheme C

Scheme C

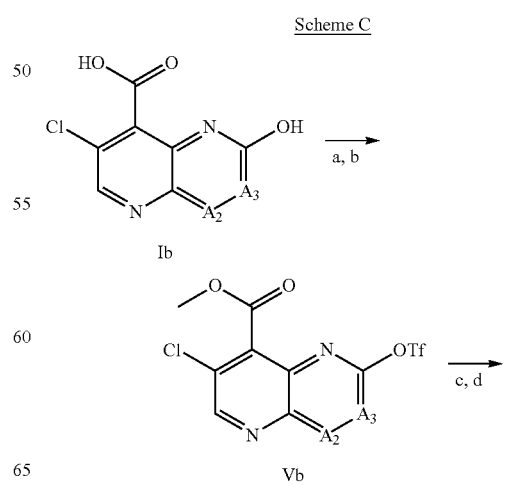

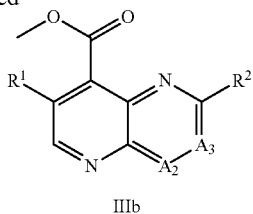

IIIb a: MeOH, H₂SO₄
b: Tf₂O, Et₃N
c: R²B(OH)₂, Pd
d: R¹B(OH)₂, Pd

Compound Ib is reacted with an alcohol such as methanol in the presence of a strong acid such as sulfuric acid to form ester and followed by formation of the triflate to produce Vb. Two consecutive but selective Suzuki-Miyaura reactions with R²B(OH)₂ and then R¹B(OH)₂ leads to formation of compound IIIb. Following the same route in Scheme A from III to IV, the final desired compounds are obtained.

In some embodiments, compounds described herein are prepared as described in Scheme D using Ib as the starting material.

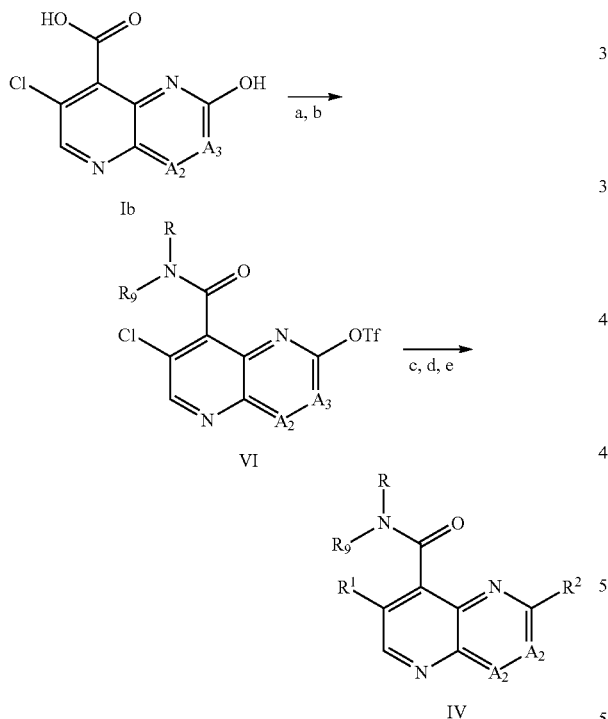

a: RR⁹NH, HATU, DMF
b: Tf₂O, Et₃N
c: R²B(OH)₂, Pd or amine, heating
d: R¹B(OH)₂, Pd or amine, Pd, base
e: deprotection Compound Ib is coupled with the mono-protected diamine (RR⁹NH, where R containing a protected amino group), in the presence of a coupling reagent such as HATU, followed by formation of the triflate to produce VI. Two consecutive but selective Suzuki-Miyaura reactions with R²B(OH)₂ and then R¹B (OH)₂ or other similar coupling reactions and subsequent removal of all protecting groups using appropriate deprotection methods such as acid, yield the compound IV. Alternatively, R¹ or R² is a substituted amino group, where R² is introduced by heating of VI with an amine in step c, and R¹ is introduced by Buchwald-Hartwig amination of chloride with an amine in step d.

In some embodiments, compounds described herein are prepared as described in Scheme E using V as the starting material.

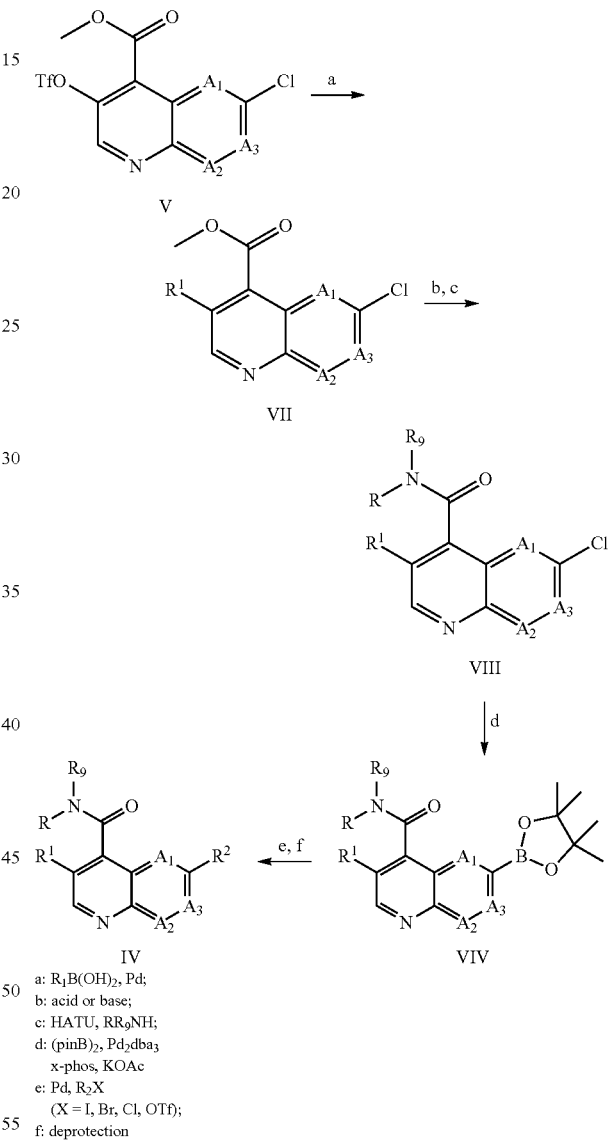

a: R₁B(OH)₂, Pd;
b: acid or base;
c: HATU, RR₉NH;
d: (pinB)₂, Pd₂dba₃ x-phos, KOAc
e: Pd, R₂X (X = I, Br, Cl, OTf);
f: deprotection Compound V which is described in the previous Scheme II undergoes a selective Suzuki-Miyaura reaction to obtain compound VII. The ester of VII is removed by acid or base, followed by a coupling reaction with the amine RR₉NH to form amide compound VIII. The boronic ester VIV is formed when VIII is reacted with (pinB)₂ in the presence of a palladium catalyst such as Pd₂dba₃ with a ligand such as x-Phos. A Suzuki-Miyaura reaction with a halogen of triflate of R₂, followed by deprotection yields the desired compound IV.

In some embodiments, the compounds obtained from the above mentioned methods are prepared as racemic or diastereomic mixtures. In some other embodiments, racemic mixtures of the compounds are separated to obtain optically pure (or optically enriched) isomers by the use of common chiral separation methods such as chiral HPLC, chiral supercritical fluid chromatographic system (SFC), simulated moving bed chromatography (SMB), and the like.

In some other embodiments, diastereomic mixtures of the compounds are separated to obtain optically pure (or optically enriched) isomers by the use of crystallization methods or common non-chiral chromatography methods such as silica gel chromatography or chiral chromatography methods such as chiral HPLC, chiral supercritical fluid chromatographic system (SFC), simulated moving bed chromatography (SMB), and the like.

In some embodiments, compounds described herein are synthesized as outlined in the Examples.

Certain Terminology

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

As used herein, $C_1$-$C_x$ includes $C_1$-$C_2$, $C_1$-$C_3$ ... $C_1$-$C_x$. By way of example only, a group designated as "$C_1$-$C_6$" indicates that there are one to six carbon atoms in the moiety, i.e. groups containing 1 carbon atom, 2 carbon atoms, 3 carbon atoms or 4 carbon atoms. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso -butyl, sec-butyl, and t-butyl.

An "alkyl" group refers to an aliphatic hydrocarbon group. The alkyl group is branched or straight chain. In some embodiments, the "alkyl" group has 1 to 10 carbon atoms, i.e. a $C_1$-$C_{10}$alkyl. Whenever it appears herein, a numerical range such as "1 to 10" refers to each integer in the given range; e.g., "1 to 10 carbon atoms" means that the alkyl group consist of 1 carbon atom, 2 carbon atoms, 3 carbon atoms, etc., up to and including 10 carbon atoms, although the present definition also covers the occurrence of the term "alkyl" where no numerical range is designated. In some embodiments, an alkyl is a $C_1$-$C_6$alkyl. In one aspect the alkyl is methyl, ethyl, propyl, iso-propyl, n-butyl, iso-butyl, sec-butyl, or t-butyl. Typical alkyl groups include, but are in no way limited to, methyl, ethyl, propyl, isopropyl, butyl, isobutyl, sec-butyl, tertiary butyl, pentyl, neopentyl, or hexyl.

An "alkylene" group refers refers to a divalent alkyl radical. Any of the above mentioned monovalent alkyl groups may be an alkylene by abstraction of a second hydrogen atom from the alkyl. In some embodiments, an alkelene is a $C_1$-$C_6$alkylene. In other embodiments, an alkylene is a $C_1$-$C_4$alkylene. Typical alkylene groups include, but are not limited to, —$CH_2$—, —$CH_2CH_2$—, —$CH_2CH_2CH_2$—, —$CH_2CH_2CH_2CH_2$—, and the like. In some embodiments, an alkylene is —$CH_2$—.

An "alkoxy" group refers to a (alkyl)O— group, where alkyl is as defined herein.

The term "alkylamine" refers to the —N(alkyl)$_x$H$_y$ group, where x is 0 and y is 2, or where x is 1 and y is 1, or where x is 2 and y is 0.

An "hydroxyalkyl" refers to an alkyl in which one hydrogen atom is replaced by a hydroxyl. In some embodiments, a hydroxyalkyl is a $C_1$-$C_4$hydroxyalkyl. Typical hydroxyalkyl groups include, but are not limited to, —$CH_2OH$, —$CH_2CH_2OH$, —$CH_2CH_2CH_2OH$, —$CH_2CH_2CH_2CH_2OH$, and the like.

An "aminoalkyl" refers to an alkyl in which one hydrogen atom is replaced by an amino. In some embodiments, aminoalkyl is a $C_1$-$C_4$aminoalkyl. Typical aminoalkyl groups include, but are not limited to, —$CH_2NH_2$, —$CH_2CH_2NH_2$, —$CH_2CH_2CH_2NH_2$, —$CH_2CH_2CH_2CH_2NH_2$, and the like.

The term "alkenyl" refers to a type of alkyl group in which at least one carbon-carbon double bond is present. In one embodiment, an alkenyl group has the formula —C(R)=CR$_2$, wherein R refers to the remaining portions of the alkenyl group, which may be the same or different. In some embodiments, R is H or an alkyl. In some embodiments, an alkenyl is selected from ethenyl (i.e., vinyl), propenyl (i.e., allyl), butenyl, pentenyl, pentadienyl, and the like. Non-limiting examples of an alkenyl group include —CH=$CH_2$, —C($CH_3$)=$CH_2$, —CH=$CHCH_3$, —C($CH_3$)=$CHCH_3$, and —$CH_2$CH=$CH_2$.

The term "alkynyl" refers to a type of alkyl group in which at least one carbon-carbon triple bond is present. In one embodiment, an alkenyl group has the formula —C≡C—R, wherein R refers to the remaining portions of the alkynyl group. In some embodiments, R is H or an alkyl. In some embodiments, an alkynyl is selected from ethynyl, propynyl, butynyl, pentynyl, hexynyl, and the like. Non-limiting examples of an alkynyl group include —C≡CH, —C≡CCH$_3$ —C≡CCH$_2$CH$_3$, —CH$_2$C≡CH.

The term "heteroalkyl" refers to an alkyl group in which one or more skeletal atoms of the alkyl are selected from an atom other than carbon, e.g., oxygen, nitrogen (e.g. —NH—, —N(alkyl)—, sulfur, or combinations thereof. A heteroalkyl is attached to the rest of the molecule at a carbon atom of the heteroalkyl. In one aspect, a heteroalkyl is a $C_1$-$C_6$heteroalkyl.

The term "aromatic" refers to a planar ring having a delocalized π-electron system containing 4n+2 π electrons, where n is an integer. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "carbocyclic" or "carbocycle" refers to a ring or ring system where the atoms forming the backbone of the ring are all carbon atoms. The term thus distinguishes carbocyclic from "heterocyclic" rings or "heterocycles" in which the ring backbone contains at least one atom which is different from carbon. In some embodiments, at least one of the two rings of a bicyclic carbocycle is aromatic. In some embodiments, both rings of a bicyclic carbocycle are aromatic. Carbocycles include aryls and cycloalkyls.

As used herein, the term "aryl" refers to an aromatic ring wherein each of the atoms forming the ring is a carbon atom. In one aspect, aryl is phenyl or a naphthyl. In some embodiments, an aryl is a phenyl. In some embodiments, an aryl is a phenyl, naphthyl, indanyl, indenyl, or tetrahyodronaphthyl. In some embodiments, an aryl is a $C_6$-$C_{10}$aryl. Depending on the structure, an aryl group is a monoradical or a diradical (i.e., an arylene group).

The term "cycloalkyl" refers to a monocyclic or polycyclic aliphatic, non-aromatic radical, wherein each of the atoms forming the ring (i.e. skeletal atoms) is a carbon atom. In some embodiments, cycloalkyls are spirocyclic or bridged compounds. In some embodiments, cycloalkyls are optionally fused with an aromatic ring, and the point of attachment is at a carbon that is not an aromatic ring carbon atom. Cycloalkyl groups include groups having from 3 to 10 ring atoms. In some embodiments, cycloalkyl groups are selected from among cyclopropyl, cyclobutyl, cyclopentyl, cyclopentenyl, cyclohexyl, cyclohexenyl, cycloheptyl, cyclooctyl, spiro[2.2]pentyl, norbornyl and bicycle[1.1.1]pentyl. In some embodiments, a cycloalkyl is a $C_3$-$C_6$cycloalkyl.

The term "halo" or, alternatively, "halogen" or "halide" means fluoro, chloro, bromo or iodo. In some embodiments, halo is fluoro, chloro, or bromo.

The term "fluoroalkyl" refers to an alkyl in which one or more hydrogen atoms are replaced by a fluorine atom. In one aspect, a fluoralkyl is a $C_1$-$C_6$fluoroalkyl.

The term "heterocycle" or "heterocyclic" refers to heteroaromatic rings (also known as heteroaryls) and heterocycloalkyl rings containing one to four heteroatoms in the ring(s), where each heteroatom in the ring(s) is selected from O, S and N, wherein each heterocyclic group has from 3 to 10 atoms in its ring system, and with the proviso that any ring does not contain two adjacent O or S atoms. Non-aromatic heterocyclic groups (also known as heterocycloalkyls) include rings having 3 to 10 atoms in its ring system and aromatic heterocyclic groups include rings having 5 to 10 atoms in its ring system. The heterocyclic groups include benzo-fused ring systems. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1H-benzo[d]imidazol-2(3H)-onyl, benzo[d]thiazol-2(3H)-onyl, and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups are either C-attached (or C-linked) or N-attached where such is possible. For instance, a group derived from pyrrole includes both pyrrol-1-yl (N -attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles are optionally substituted with one or two oxo (=O) moieties, such as pyrrolidin-2-one. In some embodiments, at least one of the two rings of a bicyclic heterocycle is aromatic. In some embodiments, both rings of a bicyclic heterocycle are aromatic.

The terms "heteroaryl" or, alternatively, "heteroaromatic" refers to an aryl group that includes one or more ring heteroatoms selected from nitrogen, oxygen and sulfur. Illustrative examples of heteroaryl groups include monocyclic heteroaryls and bicycicic heteroaryls. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Monocyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, bicyclic heteroaryl is a $C_6$-$C_9$heteroaryl.

A "heterocycloalkyl" group refers to a cycloalkyl group that includes at least one heteroatom selected from nitrogen, oxygen and sulfur. In some embodiments, a heterocycloalkyl is fused with an aryl or heteroaryl. In some embodiments, the heterocycloalkyl is oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, piperidin-2-onyl, pyrrolidine-2,5-dithionyl, pyrrolidine-2,5-dionyl, pyrrolidinonyl, imidazolidinyl, imidazolidin-2-onyl, or thiazolidin-2-onyl. The term heterocycloalkyl also includes all ring forms of the carbohydrates, including but not limited to the monosaccharides, the disaccharides and the oligosaccharides. In one aspect, a heterocycloalkyl is a $C_2$-$C_{10}$heterocycloalkyl. In another aspect, a heterocycloalkyl is a $C_4$-$C_{10}$heterocycloalkyl. In some embodiments, a heterocycloalkyl contains 0-2 N atoms in the ring. In some embodiments, a heterocycloalkyl contains 0-2 N atoms, 0-2 O atoms and 0-1 S atoms in the ring.

The term "bond" or "single bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term "moiety" refers to a specific segment or functional group of a molecule. Chemical moieties are often recognized chemical entities embedded in or appended to a molecule.

The term "optionally substituted" or "substituted" means that the referenced group is optionally substituted with one or more additional group(s) individually and independently selected from halogen, —CN, —NH$_2$, —NH(alkyl), —N(alkyl)$_2$, —OH, —CO$_2$H, —CO$_2$alkyl, —C(=O)NH$_2$, —C(=O)NH(alkyl), —C(=O)N(alkyl)$_2$, —S(=O)$_2$NH$_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, optional substituents are independently selected from halogen, —CN, —NH$_2$, —NH(CH$_3$), —N(CH$_3$)$_2$, —OH, —CO$_2$H, —CO$_2$($C_1$-$C_4$alkyl), —C(=O)NH$_2$, —C(=O)NH($C_1$-$C_4$alkyl), —C(=O)N($C_1$-$C_4$alkyl)$_2$, —S(=O)$_2$NH$_2$, —S(=O)$_2$NH($C_1$-$C_4$alkyl), —S(=O)$_2$N($C_1$-$C_4$alkyl)$_2$, $C_1$-$C_4$alkyl, $C_3$-$C_6$cycloalkyl, $C_1$-$C_4$fluoroalkyl, $C_1$-$C_4$heteroalkyl, $C_1$-$C_4$alkoxy, $C_1$-$C_4$fluoroalkoxy, —$SC_1$-$C_4$alkyl, —$S(=O)C_1$-$C_4$alkyl, and —$S(=O)_2C_1$-$C_4$alkyl. In some embodiments, optional substituents are independently selected from halogen, —CN, —$NH_2$, —OH, —$NH(CH_3)$, —$N(CH_3)_2$, —$CH_3$, —$CH_2CH_3$, —$CF_3$, —$OCH_3$, and —$OCF_3$. In some embodiments, substituted groups are substituted with one or two of the preceding groups. In some embodiments, an optional substituent on an aliphatic carbon atom (acyclic or cyclic) includes oxo (=O).

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an agonist.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound of Formula (I), or a pharmaceutically acceptable salt thereof, and a co-agent, are both administered to a patient simultaneously in the form of a single entity or dosage. The term "non-fixed combination" means that the active ingredients, e.g. a compound of Formula (I), or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "article of manufacture" and "kit" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Pharmaceutical Compositions

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the compounds described herein are administered either alone or in combination with pharmaceutically acceptable carriers, excipients or diluents, in a pharmaceutical composition. Administration of the compounds and compositions described herein can be effected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient. By way of example only, compounds described herein can be administered locally to the area in need of treatment, by for example, local infusion during surgery, topical application such as creams or ointments, injection, catheter, or implant. The administration can also be by direct injection at the site of a diseased tissue or organ.

In some embodiments, pharmaceutical compositions suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

In some embodiments, pharmaceutical compositions are formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The compositions may be presented in unit-dose or multi -dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical compositions may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Pharmaceutical compositions may be administered topically, that is by non-systemic administration. This includes the application of a compound of the present invention externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Pharmaceutical compositions suitable for topical administration include liquid or semi- liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation.

Pharmaceutical compositions for administration by inhalation are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, pharmaceutical preparations may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

It should be understood that in addition to the ingredients particularly mentioned above, the compounds and compositions described herein may include other agents conventional in the art having regard to the type of formulation in question, for example those suitable for oral administration may include flavoring agents.

Methods of Dosing and Treatment Regimens

In one embodiment, the compounds of Formula (I), or a pharmaceutically acceptable salt thereof, are used in the preparation of medicaments for the treatment of diseases or conditions in a mammal that would benefit from modulation of somatostatin activity. Methods for treating any of the diseases or conditions described herein in a mammal in need of such treatment, involves administration of pharmaceutical compositions that include at least one compound of Formula (I) or a pharmaceutically acceptable salt, active metabolite, prodrug, or pharmaceutically acceptable solvate thereof, in therapeutically effective amounts to said mammal.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising a compound of Formula (I), or a pharmaceutically acceptable salt thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-2000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound of Formula (I), or a pharmaceutically acceptable salt thereof, described herein are from about 0.01 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

In any of the aforementioned aspects are further embodiments in which the effective amount of the compound of Formula (I), or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the compound, including further embodiments in which (i) the compound is administered once a day; or (ii) the compound is administered to the mammal multiple times over the span of one day.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

Combination Treatments

In certain instances, it is appropriate to administer at least one compound of Formula (I), or a pharmaceutically acceptable salt thereof, in combination with one or more other therapeutic agents.

In one embodiment, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced). Or, in some embodiments, the benefit experienced by a patient is increased by administering one of the compounds described herein with another agent (which also includes a therapeutic regimen) that also has therapeutic benefit.

In one specific embodiment, a compound of Formula (I), or a pharmaceutically acceptable salt thereof, is co-administered with a second therapeutic agent, wherein the compound of Formula (I), or a pharmaceutically acceptable salt thereof, and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient is simply be additive of the two therapeutic agents or the patient experiences a synergistic benefit.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds of Formula (I), or a pharmaceutically acceptable salt thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject.

EXAMPLES

Abbreviations:
ABCN: 1,1'-azobis(cyclonexanecarbonitrile);
BINAP: (2,2'-bis(diphenylphosphino)-1,1'-binaphthyl);
DCM: dichloromethane,
EtOAc: ethyl acetate;
HATU: 1-[bis(dimethylamino)methylene]-1H-1,2,3-triazolo[4,5-b]pyridinium 3-oxid hexailuorophosphate;
NBS: N-bromosuccinimide;
NCS: N-chlorosuccinimide
PTS: p-toluene sulfonic acid;
Pd (amphos)Cl$_2$: bis(di-tert-butyl(4-dimethylaminophenyl)phosphine)dichloropalladium(II);
Pd$_2$dba$_3$: tris(dibenzylideneacetone)dipalladium(0);
(pinB)$_2$: bis(pinacolato)diboron;
rt: room temperature;
SST: somatostatin:
SSTR: somatostatin receptor;
TEA: trirnethylamine;
TFA: trifluoroacetic acid;
x-phos: 2-dicyclohexylphosphino-2',4',6'-triisopropylbiphenyl;
hrs: hours;
h or hr: hour.

The following examples are provided for illustrative purposes only and not to limit the scope of the claims provided herein.

Synthesis of Compounds

Example 1: 3-(3-chloro-5-methylphenyl)-6-(3-hydroxyphenyl)-N-methyl-N-[(2S)-pyrrolidin-2-ylmethyl]quinoline-4-carboxamide

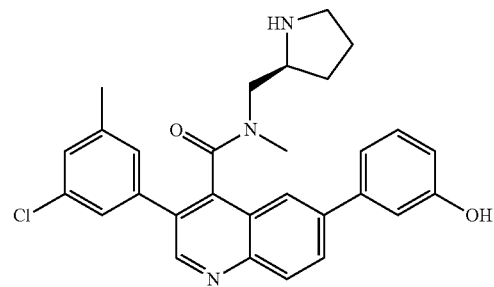 [SMILES: Cc1cc(Cl)cc(-c2cnc3ccc(-c4cccc(O)c4)cc3c2C(=O)N(C)C[C@@H]2CCCN2)c1]

Step 1-1, preparation of 6-bromo-3-hydroxy-quinoline-carboxylic acid methyl ester: to 6-bromo-3-hydroxy-quinoline-carboxylic acid (5.0 g, 17.5 mmol) in 60 mL methanol was added sulfuric acid (20 ml), and the resulting mixture was stirred at 95° C. for 17 h. The reaction solution was diluted with water (400 ml) and resulted precipitates were filtered and redissolved in ethyl acetate and dried with MgSO$_4$, concentrated to give a solid (1.17 g).MS (M+H)$^+$: 282.0

Step 1-2, preparation of 6-(3-benzyloxy-phenyl)-3-hydroxy-quinoline-4-carboxylic acid methyl ester: the solid from Step 1-1 (282.1 mg, 1 mmol) was dissolved in dioxane (8 mL) with water (0.8 ml), 3-benzoxylphenyl boronic acid (456.2 mg 2.0 mmmol), and K$_3$PO$_4$.H$_2$O (690.9 mg, 3.0 mmol) were added. The mixture was bubbled with N₂ for 10 min, tris(dibenzylideneacetone) dipalladium/tri-tert-butyl phosphonium tetrafluoroborate mixture (mole ratio: 1/1.2) (50 mg, 0.039 mmol) was added. The resulting mixture was stirred at 55° C. for 2 hrs. The reaction mixture was concentrated and purified by silica gel chromatography to give desired product as brown oil (194 mg). MS (M+H)⁺: 386.2.

Step 1-3, preparation of 6-(3-benzyloxy-phenyl)-3-trifluoromethanesulfonyloxy -quinoline-4-carboxylic acid methyl ester: to the oil (194 mg, 0.5 mmol) from Step 1-2 in DCM (4 mL), TEA (0.2 ml, 1.4 mmol) was added, followed by addition of trifluoromethanesulfonic anhydride (Tf₂O, 0.16 ml, 1.0 mmol). The reaction mixture was stirred at rt for 0.5 hr, additional Tf₂O (0.08 ml) and TEA (0.14 ml) were added. The reaction solution was then stirred for additional 1 h, concentrated and purified by silica gel chromatography eluted with hexane and ethyl acetate to afford a brown oil as the desired product (157 mg). MS (M+1)⁺: 518.3.

Step 1-4, preparation of 6-(3-benzyloxy-phenyl)-3-(3-chloro-5-methyl-phenyl) -quinoline-4-carboxylic acid methyl ester: to the dioxane solution (3 mL) of the oil from Step 1-3 (157 mg, 0.3 mmol) was added, followed by addition of 3-chloro-5-methyl-phenylboronic acid (102 mg, 0.6 mmol), K₂CO₃ (83 mg, 0.6 mmol) and water (0.8 mL). The reaction mixture was bubbled with N₂ for 5 min and then Pd(amphos)Cl₂ was added and the mixture was stirred at 90° C. for 45 min. The reaction solution was concentrated and purified by silica gel chromatography eluted with hexane and ethyl acetate to afford the desired product (120 mg). MS (M+1)⁺: 494.5.

Step 1-5, preparation of 6-(3-benzyloxy-phenyl)-3-(3-chloro-5-methyl-phenyl) -quinoline-4-carboxylic acid: to the THF solution (3 mL) of the oil from Step 1-4 (120 mg,) was added NaOH solution (4M, 2 mL). The resulting mixture was stirred at 75° C. for 5 h. The reaction solution was acidified with HCl solution (4.0 M) to pH 2. The crude was extracted with ethyl acetate and washed with brine, dried with MgSO₄ and concentrated to afford a brown solid. This material was used for next Step without further purification. MS (M+1)⁺: 480.1.

Step 1-6, preparation of (2S)-2-({[6-(3-benzyloxy-phenyl)-3-(3-chloro-5-methyl -phenyl)-quinoline-4-carbonyl]-methyl-amino}-methyl)-pyrrolidine-1-carboxylic acid tert-butyl ester: to the DMF (0.75 mL) solution of the acid from Step 1-5 (25 mg, 0.05 mmol) was added triethylamine (0.026 mL, 0.15 mmol) and HATU (38 mg, 0.1 mmol), then 2-(S) -methylaminomethyl-pyrrolidine-1-carboxylic acid tert-butyl ester (20 mg, 0.1 mmol) was added. The reaction mixture was stirred at rt for 10 min. The reaction solution was diluted with EtOAc, washed with NaOH (1N, 2 mL) and brine, dried with MgSO₄, concentrated and purified by silica gel chromatography to afford the desired product as brown oil (20 mg). MS (M+1)⁺: 676.6.

Step 1-7, preparation of 3-(3-chloro-5-methylphenyl)-6-(3-hydroxyphenyl)-N-methyl -N-[(2S)-pyrrolidin-2-ylmethyl]quinoline-4-carboxamide: to the oil from Step 1-6, was added trifluoroacetic acid (1 mL) and thioanisole (0.1 ml). The resulting mixture was stirred at 60° C. for 1h. Then it was concentrated and purified by a reversed-phase column chromatography eluted with water and acetonitrile which contains 0.1% of TFA. All factions containing desired product were combined, neutralized with saturated NaHCO₃ solution, then extracted with EtOAc. The organic layer was separated, dried with MgSO₄ and concentrated. The resulting residue was dissolved in MeOH (1 mL) and treated with HCl in EtOAc (1M, 1 mL). The solution was concentrated under high vacuum to give the final product (10 mg) as a HCl salt (Compound 1-1). MS (M+1)⁺: 486.3.

The following compounds were prepared similarly to Example 1 with appropriate substituting reagents and substrates at different steps:

| Compound no. | MS (M + H)⁺ |
|---|---|
| 1-2 | 460.4 |
| 1-3 | 474.2 |
| 1-4 | 470.5 |
| 1-6 | 486.3 |
| 1-7 | 456.5 |
| 1-18 | 456.5 |
| 1-73 | 509.6 |

N-[(2S)-2-aminobutyl]-6-(3-carbamoyl-5-hydroxyphenyl)-3-(3-chloro-5-methylphenyl)-N-methylquinoline-4-carboxamide (Compound 1-8) was prepared similarly except carboxamide was obtained from the corresponding cyano group during saponification in Step 1-5. MS (M+1)⁺: 518.3.

Example 2: N-[(2S)-2-aminobutyl]-6-(3-cyano-5-methoxyphenyl)-3-(3-fluoro-5-methylphenyl)-N-methylouinoline-4-carboxamide

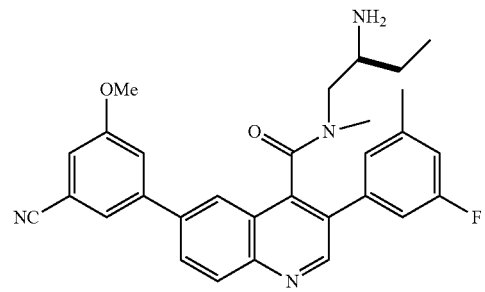 [SMILES: CC[C@H](N)CN(C)C(=O)c1c(-c2cc(C)cc(F)c2)cnc2ccc(-c3cc(C#N)cc(OC)c3)cc12]

Step 2-1, preparation of 6-chloro-3-(3-fluoro-5-methylphenyl)-quinoline-4-carboxylic acid methyl ester: to 6-chloro-3-trifluoromethanesulfonyloxy-quinoline-4-carboxylic acid methyl ester (1.85 g, 5.0 mmol), 3-fluoro-5-methylphenylboronic acid (1.16 g, 7.5 mmol), K₃PO₄.H₂O (2.3 g, 10 mmol), Pd₂dba₃/t-Bu₃P (1/1.2, 276 mg, 0.21 mmol) in THF/water (20 ml/2 ml) for 5 min. The mixture was sealed and stirred for 2 hrs. The crude was extracted with ethyl acetate, then washed with brine, and concentrated. The resulted oil was purified by silica gel column chromatography eluted with hexane/ethyl acetate to yield the desired compound (1.45 g). MS (M+H)⁺: 330.3.

Step 2-2, preparation of 6-chloro-3-(3-fluoro-5-methylphenyl)-quinoline-4-carboxylic acid: 6-chloro-3-(3-fluoro-5-methyl-phenyl)-quinoline-4-carboxylic acid methyl ester (1.45 g) obtained from the previous step was refluxed with conc.HCl (45 ml) in toluene (15 ml) for 17 hrs. LCMS showed about 50% converstion of ester to acid. Therefore, additional toluene (10 ml) and conc. HCl (10 ml) were added. The mixture was refluxed for another 10 hr, cooled to rt. Toluene was removed and the gummy material in water was titrated with acetone to form a precipate which was filtered to yield the desired compound (1.05 g). MS (M+H)⁺: 316.2.

Step 2-3, preparation benzyl N-[(2S)-1-{1-[6-chloro-3-(3-fluoro-5-methylphenyl)quinolin-4-yl]-N-methylformamido}butan-2-yl]carbamate: a mixture of 6-chloro-3-(3-fluoro-5-methyl-phenyl)-quinoline-4-carboxylic acid obtained from the previous step (0.63 g, 2 mmol), TEA (1.2 ml, 3.5 eq), HATU (1.14 g, 1.5 eq), (S)-(1-methylaminomethyl-propyl)-carbamic acid benzyl ester (1.2 ml) were stirred in dry DMF (8 ml) for 2 hrs. The mixture was diluted with ethyl acetate, then washed with NaOH solution (0.1 N, 10 ml), water, brine and concentrated. The crude was purified by silica gel column chromatography to give the desired product (0.95 g) as a brown oil. MS (M+H)$^+$: 534.4.

Step 2-4, preparation of benzyl N-[(2S)-1-{1-[6-(3-cyano-5-methoxyphenyl)-3-(3-fluoro-5-methylphenyl)quinolin-4-yl]-N-methylformamido}butan-2-yl]carbamate: to benzyl N -[(2S)-1-{1-[6-chloro-3-(3-fluoro-5-methylphenyl)quinolin-4-yl]-N-methylformamido}butan-2-yl]carbamate (267 mg, 0.5 mmol), 3-methoxy-5-(4,4,5,5-tetramethyl-[1,3,2]dioxaborolan-2-yl) -benzonitrile (259 mg, 1.0 mmol), Pd (amphos)Cl$_2$ (25 mg, 0.035 nmol), K$_2$CO$_3$ (138 mg, 1.0 mmol) in dioxane/water (4 ml/ 0.4 ml), N$_2$ was bubbled through for 1 mm. The mixture was sealed and heated at 90° C. for 2 hrs. The mixture was extracted with ethyl acetate, washed with water, brine, concentrated. The crude was purified by silica gel column chromatograpy eluted with hexane/ethyl acetate to give the desired compound (300 mg). (M+H)$^+$: 631.8.

Step 2-5, preparation of N-[(2S)-2-aminobutyl]-6-(3-cyano-5-methoxyphenyl)-3-(3-fluoro-5-methylphenyl)-N-methylquinoline-4-carboxamide: benzyl N-[(2S)-1-{1-[6-(3-cyano-5-methoxyphenyl)-3-(3-fluoro-5-methylphenyl)quinolin-4-yl]-N-methylformamido}butan-2-yl]carbamate (300 mg, 0.48) was stirred in TFA (4 ml) in the presence of thioanisole (0.3 ml) for 1 h at 65° C. It was then concentrated and the crude was purified by RP C18 column chromtagraphy eluted with water/ acetonitrile (both containing 0.5% of TFA) to yield the desired compound as TFA salt. The free amine was obtained by dissolving the TFA salt of the product in ethyl acetate, then washed with sat NaHCO$_3$ solution, dried over MgSO$_4$, and filtered, followed by concentration. It was further converted to HCl salt by redissolving it in 6 N HCl in 2-propanol and then concentrated to remove all solvents (175 mg, Compound 1-9). (M+H)$^+$: 497.5. Alternatively, HCl in isopropanol or dioxane was also used for this step when Boc protecting group was used.

The following compounds were prepared similarly to Example 2 with appropriate substituting reagents and substrates at different steps:

| Compound no. | MS (M + H)$^+$ |
|---|---|
| 1-10 | 488.3 |
| 1-11 | 472.4 |
| 1-12 | 481.3 |
| 1-13 | 474.2 |
| 1-14 | 475.2 |
| 1-15 | 485.5 |
| 3-8 | 480.4 |
| 1-16 | 479.3 |
| 3-10 | 458.4 |
| 1-17 | 490.4 |
| 1-19 | 483.3 |
| 1-20 | 471.3 |
| 1-21 | 509.6 |
| 1-22 | 501.3 |
| 1-23 | 492.2 |
| 1-24 | 497.4 |
| 1-25 | 501.0 |
| 1-26 | 519.2 |
| 1-27 | 513.4 |
| 1-28 | 501.3 |
| 1-29 | 486.4 |
| 1-30 | 513.4 |
| 1-31 | 508.4 |
| 1-32 | 501.0 |
| 1-34 | 499.3 |
| 1-35 | 527.3 |
| 1-38 | 487.4 |
| 1-45 | 523.5 |
| 1-51 | 497.5 |
| 1-52 | 497.5 |
| 1-55 | 489.4 |
| 3-40 | 510.6 |
| 3-48 | 455.4 |
| 3-59 | 473.4 |
| 3-60 | 493.4 |
| 3-61 | 493.3 |

6-(5-carbamoylpyridin-3-yl)-3-[3-fluoro-5-(2-hydroxyethyl)phenyl]-N-methyl-N -[(2S)-pyrrolidin-2-ylmethyl] quinoline-4-carboxamide (Compound 3-58) was obtained as a side product from synthesis of Compound 3-40 during the deprotection step (Step 2-5). (M+H)$^+$: 528.1.

Example 3: 3-(3-chloro-5-methylphenyl)-6-(3-hydroxyphenyl)-N-methyl-N-[(2R) -pyrrolidin-2-ylmethyl]quinoline-4-carboxamide

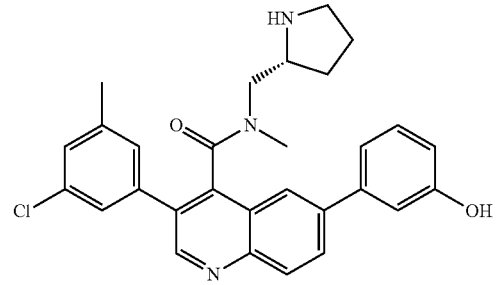 [SMILES: Cc1cc(Cl)cc(-c2cnc3ccc(-c4cccc(O)c4)cc3c2C(=O)N(C)C[C@H]2CCCN2)c1]

Step 3-1, preparation of tert-butyl (2R)-2-[({6-[3-(benzyloxy)phenyl]-3-(3-chloro-5-methylphenyl)quinolin-4-yl}formamido)methyl]pyrrolidine-1-carboxylate: to the DMF (0.75 mL) solution of the acid from Step 1-5 of Example 1 (48 mg, 0.1 mmol) was added triethylamine (0.052 mL, 0.3 mmol) and HATU (76 mg, 0.2 mmol), then 2-(R)-aminomethyl -pyrrolidine-1-carboxylic acid tert-butyl ester (20 mg, 0.1 mmol) was added. The reaction mixture was stirred at rt for 1 h. The reaction solution was diluted with EtOAc, washed with NaOH (1N, 2 mL) and brine, dried with MgSO$_4$, concentrated and purified by silica gel chromatography to afford the desired product as brown oil (32 mg). MS (M+1)$^+$: 662.5.

Step 3-2, preparation of tert-butyl (2R)-2-[(1-{6-[3-(benzyloxy)phenyl]-3-(3-chloro-5-methylphenyl)quinolin-4-yl}-N-methylformamido)methyl]pyrrolidine-1-carboxylate: to the THF (anhydrous, 2 ml) of the above oil (32 mg, 0.05 mmol), NaH (10 mg, 60% in mineral oil, 0.25 mmol) was added, followed by addition of MeI (0.02 ml, 0.3 mmol). The mixture was stirred at rt for 1 h, then extracted with ethyl acetate. The organic layer was washed with water, brine, dried over MgSO$_4$, and concentrated to give an oil which was used for next step without further purication. MS (M+1)$^+$: 676.5

Step 3-3, preparation of 3-(3-chloro-5-methylphenyl)-6-(3-hydroxyphenyl)-N-methyl -N-[(2R)-pyrrolidin-2-ylmethyl]quinoline-4-carboxamide: to the oil from Step 3-2, was added trifluoroacetic acid (1 mL) and thioanisole (0.1 ml). The resulting mixture was stirred at 60° C. for 2 h. Then it was concentrated and purified by a reversed-phase column chromatography eluted with water and acetonitrile which contains 0.1% of TFA. All factions containing desired product were combined, neutralized with saturated NaHCO$_3$ solution, then extracted with EtOAc. The organic layer was separated, dried with MgSO$_4$ and concentrated. The resulting residue was dissolved in MeOH (1 mL) and treated with HCl in EtOAc (1M, 0.1 mL). The solution was concentrated to give the final product (12 mg) as a HCl salt (Compound 1-5). MS (M+1)$^+$: 486.3.

Example 4: 3-(3-chloro-5-methylphenyl)-6-(3-hydroxyphenyl)-N-methyl-N-[(2S) -pyrrolidin-2-ylmethyl]-1,5-naphthyridine-4-carboxamide

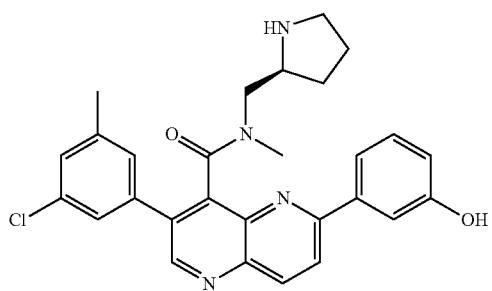 [SMILES: Cc1cc(Cl)cc(-c2cnc3ccc(-c4cccc(O)c4)nc3c2C(=O)N(C)C[C@@H]2CCCN2)c1]

Step 4-1, preparation of (2S)-2-{[1-(3-chloro-6-hydroxy-1,5-naphthyridin-4-yl)-N -methylformamido]methyl}pyrrolidine-1-carboxylate: A mixture of 3-chloro-6-hydroxy -[1,5]naphthyridine-4-carboxylic acid (449.2 mg, 2.0 mmol), (S)-2-methylaminomethyl -pyrrolidine-1-carboxylic acid benzyl ester (0.65 g, 3.0 mmol), HATU (1.14 g, 3.0 mmol), TEA (0.70 ml, 4.0 mmol) was stirred in DMF (10 ml) at rt for 2 hrs. The mixture was extracted with ethyl acetate. The organic layer was washed with water, dried, concentrated and purified by column chromatagrpahy using DCM and ethyl acetate as elutes to obtain the desired product (0.8 g) which is about 50% pure. MS (M+1)$^+$: 455.3.

Step 4-2, preparation of benzyl (2S)-2-({1-[3-chloro-6-(trifluoromethanesulfonyloxy) -1,5-naphthyridin-4-yl]-N-methylformamido}methyl)pyrrolidine-1-carboxylate: the material from the above step (0.8 g, 0.85 mmol, 50% pure) was dissolved in anhydrous DCM (6 ml), cooled with ice bath, then TEA (1.4 ml, 8.0 mmol) was added; followed by addition of trifluoromethanesulfonic anhydride slowly (0.7 ml, 1.5 mmol). The mixture was stirred for additional 0.5 hr and extracted with DCM. Organic layer was washed with water, concentrated and purified by silica gel column chromatography eluted with DCM/ethyl acetate to yield the desired product (0.33 g, 50% pure). MS (M+1)$^+$: 587.3.

Step 4-3, preparation of benzyl (2S)-2-[(1-{6-[3-(benzyloxy)phenyl]-3-chloro-1,5-naphthyridin-4-yl}-N-methylformamido)methyl]pyrrolidine-1-carboxylate: To the material from the above step in THF (6 ml)/water (0.5 ml), nitrogen gas was bubbled through for 10 min, followed by addition of 3-benzoxylphenyl boronic acid (228 mg, 1 mmol), Pd$_2$dba$_3$.t-Bu$_3$P complex (40 mg, 0.03 mmol), K$_3$PO$_4$.H$_2$O (530.4, 2.0 mmol). The mixture was sealed and stirred at rt for 2 hrs and then extracted with ethyl acetate. Organic layer was then washed with water, dried, concentrated and purified by silica gel column chromatography eluted with hexane/ethyl acetate to yield the desired product (220 mg). MS (M+1)$^+$: 621.2.

Step 4-4, preparation of benzyl (2S)-2-[(1-{6-[3-(benzyloxy)phenyl]-3-(3-chloro-5-methylphenyl)-1,5-naphthyridin-4-yl}-N-methylformamido)methyl]pyrrolidine-1-carboxylate: to the material from Step 4-3 (110 mg) in dioxane (2 ml), 3-chloro-5-methylphenylboronic acid (105 mg, 0.62 mmol), K$_2$CO$_3$ (82 mg, 0.6 mmol) were added. The mixture was bubbled with nitrogen for 5 min, then Pd (amphos)Cl$_2$ (11 mg, 0.016 mmol) was added. It was sealed and heated at 90° C. for 90 min and then directly purified by silica gel column chromatography eluted with hexane/ethyl acetate to give the desired product as a brown solid (66 mg). MS (M+1)$^+$: 711.6.

Step 4-5, preparation of 3-(3-chloro-5-methylphenyl)-6-(3-hydroxyphenyl)-N-methyl -N-[(2S)-pyrrolidin-2-ylmethyl]-1,5-naphthyridine-4-carboxamide: the material obtained from the above step was heated at 65° C. with TFA (2 ml) in the presence of thioanisole (0.1 ml) for 1.5 hrs. The crude was concentrated and purified by C18 reversed phase column chromatography eluted with water and acetonitrile which contain 0.1% TFA. The fractions containing desired product were combined, neutralized by NaHCO$_3$ solution, and extracted with ethyl acetate. The organic layer was then dried, filtered and treated with HCl (4N, in dioxane, 0.3 ml), then concentrated to yield the desired product (22 mg) as HCl salt (Compound 2-1). MS (M+1)$^+$: 487.4.

The following compounds were prepared similarly to Example 4 with appropriate substituting reagents and substrates at different steps:

| Compound no. | MS (M + H)$^+$ |
|---|---|
| 2-2 | 455.3 |
| 2-3 | 505.3 |
| 2-4 | 512.5 |
| 2-5 | 480.4 |
| 2-6 | 500.3 |
| 2-7 | 484.6 |
| 2-8 | 505.3 |
| 2-9 | 475.2 |
| 2-10 | 510.5 |
| 2-11 | 466.5 |
| 2-12 | 496.3 |
| 2-13 | 484.5 |
| 2-14 | 537.5 |
| 2-15 | 491.3 |
| 2-16 | 502.4 |
| 2-17 | 498.2 |
| 2-18 | 514.5 |
| 2-19 | 484.5 |
| 2-20 | 497.5 |
| 2-21 | 511.6 |
| 2-23 | 511.6 |
| 2-24 | 525.5 |

-continued

| Compound no. | MS (M + H)+ |
| --- | --- |
| 3-5 | 454.1 |
| 3-9 | 456.2 |

Example 5: 3-(3-fluoro-5-methylphenyl)-N-methyl-6-(pyrrolidin-1-yl)-N-[(2S)-pyrrolidin-2-ylmethyl]-1,5-naphthyridine-4-carboxamide

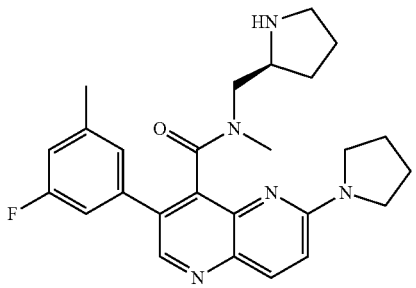 [SMILES: Cc1cc(F)cc(-c2cnc3ccc(N4CCCC4)nc3c2C(=O)N(C)C[C@@H]2CCCN2)c1]

Step 5-1, preparation of benzyl (2S)-2-({1-[3-chloro-6-(pyrrolidin-1-yl)-1,5-naphthyridin-4-yl]-N-methylformamido}methyl)pyrrolidine-1-carboxylate: benzyl (2S)-2-({1-[3-chloro-6-(trifluoromethanesulfonyloxy)-1,5-naphthyridin-4-yl]-N -methylformamido}methyl) pyrrolidine-1-carboxylate: (40 mg, 0.07 mmol), an intermediate from Example 4, was heated at 90° C. with pyrrolidine (17 µl, 0.1 mmol) in acetonitrile (1 ml) in the presence of DIPEA (0.2 ml) for 1 hr, and concentrated to be used for next step without further purification. MS (M+1)+: 508.5.

Step 5-2, preparation of benzyl (2S)-2-({1-[3-(3-fluoro-5-methylphenyl)-6-(pyrrolidin -1-yl)-1,5-naphthyridin-4-yl]-N-methylformamido}methyl)pyrrolidine-1-carboxylate: A mixture of the material obtained from the above step, 3-fluoro-5-methylphenylboronic acid (30 mg), Pd (amphos) Cl₂ (5 mg), K₂CO₃ (30 mg) was bubbled with N₂ for 10 min and then heated at 90° C. in dioxane (1 ml) under sealed condition for 2 hrs, then extracted with ethyl acetate. The organic layer was separated, concentrated and used for next step without further purification, MS (M+1)+: 582.5.

Step 5-3, preparation of 3-(3-fluoro-5-methylphenyl)-N-methyl-6-(pyrrolidin-1-yl)-N -[(2S)-pyrrolidin-2-ylmethyl]-1,5-naphthyridine-4-carboxamide: the above crude material was heated with TFA (2 ml) in the presence of thioanisole (0.1 ml) at 65° C. for 1 h. The insoluble was filtered off, and resulted solution was concentrated and purified by a reversed phase C18 column chromatography to yield the desired product (18 mg) as TFA salt (Compound 3-2). MS (M+1)+: 448.2.

(3-(3-fluoro-5-methylphenyl)-6-(3-hydroxypiperidin-1-yl)-N-methyl-N-[(2S) -pyrrolidin-2-ylmethyl]-1,5-naphthyridine-4-carboxamide (Compound 3-3) was similarly prepared according to the method in Example 5 with appropriating reagents. MS (M+1)+: 478.3.

Example 6: 6-(3-hydroxyphenyl)-N-methyl-3-(pyrrolidin-1-yl)-N-[(2S)-pyrrolidin-2-ylmethyl]-1,5-naphthyridine-4-carboxamide

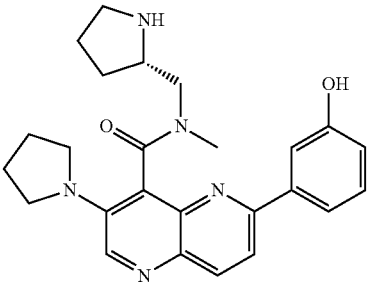 [SMILES: CN(C[C@@H]1CCCN1)C(=O)c1c(N2CCCC2)cnc2ccc(-c3cccc(O)c3)nc12]

Step 6-1, preparation of benzyl (2S)-2-[(1-{6-[3-(benzyloxy)phenyl]-3-(pyrrolidin-1-yl)-1,5-naphthyridin-4-yl}-N-methylformamido)methyl]pyrrolidine-1-carboxylate: to benzyl (2S)-2-[(1-{6-[3-(benzyloxy)phenyl]-3-chloro-1,5-naphthyridin-4-yl}-N -methylformamido)methyl]pyrrolidine-1-carboxylate (30 mg), the intermediate from Example 4, in toluene (1 ml), Argon was used in for 10 min, then, pyrrolidine (20 µl), Pd (OAc)₂ (2.2 mg), BINAP (6 mg) and Cs₂CO₃ (34 mg, 0.1 mmol) were added. The mixture was sealed and heated at 95° C. for 1 h, then extracted with ethyl acetate. The organic layer was washed with water, dried, concentrated and purified by silica gel column chromatography to yield the desired product (4.5 mg). MS (M+1)+: 656.9.

Step 6-2, preparation 6-(3-hydroxyphenyl)-N-methyl-3-(pyrrolidin-1-yl)-N-[(2S) -pyrrolidin-2-ylmethyl]-1,5-naphthyridine-4-carboxamide: the above material from Step 6-1 was heated with TFA (1 ml) in the presence of thioanisole (0.05 ml) for 1 h, then concentrated and purified by a reversed phase C18 column chromatography to yield the desired product (1.8 mg, Compound 3-4). MS (M+1)+: 432.4.

The following compounds were prepared similarly to Example 6 with appropriate substituting reagents and substrates at different steps:

| Compound no. | MS (M + H)+ |
| --- | --- |
| 3-6 | 476.3 |
| 3-11 | 446.4 |
| 3-12 | 448.2 |
| 3-17 | 462.3 |
| 3-20 | 475.4 |
| 3-21 | 475.2 |
| 3-36 | 503.3 |
| 3-42 | 551.5 |
| 3-45 | 502.4 |
| 3-47 | 551.3 |
| 3-49 | 531.4 |
| 3-54 | 575.5 |
| 3-55 | 575.4 |
| 3-64 | 520.4 |
| 3-69 | 471.3 |
| 3-70 | 501.3 |
| 3-76 | 495.5 |

Example 7: 6-(2-amino-5-cyanopyridin-3-yl)-3-(3-fluoro-5-methylphenyl)-N-methyl-N -[(2S)-pyrrolidin-2-ylmethyl]quinoline-4-carboxamide

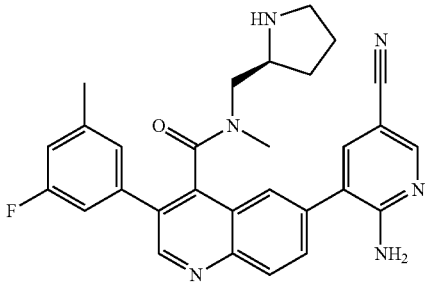 [SMILES: Cc1cc(F)cc(-c2cnc3ccc(-c4cc(C#N)cnc4N)cc3c2C(=O)N(C)C[C@@H]2CCCN2)c1]

Step 7-1, preparation of benzyl (2S)-2-({1-[6-chloro-3-(3-fluoro-5-methylphenyl)quinolin-4-yl]-N-methylformamido}methyl)pyrrolidine-1-carboxylate: a mixture of 6-chloro-3-(3-fluoro-5-methyl-phenyl)-quinoline-4-carboxylic acid, prepared in Example 2 (1.26 g, 4.0 mmol), 2-(S)-methylaminomethyl-pyrrolidine-1-carboxylic acid benzyl ester (1.2 g, 1.2 eq. 4.8 mmol), HATU (2.28 g, 1.5 eq), DIPEA (2 ml, 3.0 eq) was stirred in dry DMF (10 ml) for 2 hrs. It was then diluted with ethyl acetate. The organic layer was washed with water, brine and then concentrated. The crude was purified by silica gel column chromatography eluted with hexane/ethyl acetate to afford the desired product (1.17 g). MS (M+1)$^+$: 546.4.

Step 7-2, preparation of benzyl (2S)-2-({1-[3-(3-fluoro-5-methylphenyl)-6-(tetramethyl-1,3,2-dioxaborolan-2-yl)quinolin-4-yl]-N-methylformamido}methyl)pyrrolidine-1-carboxylate: to the material obtained from the above step (0.59 g, 1.1 mmol), bis (pinacol)diboron (0.544 g, 2.0 mmol), Pd$_2$dba$_3$ (50 mg, 0.05 mmol), x-Phos (50 mg, 0.1 mmol), potassium acetate (300 mg, 3 mmol) in dioxane (10 ml), N$_2$ gas was bubbled for 10 min. The mixture was then sealed and heated with stirring at 105° C. for 1 h. After it was cooled to rt, the mixture was extracted with ethyl acetate, the solid was filtered off. The organics were then washed with sat. NaHCO$_3$, sat NH$_4$Cl, brine, dried and concentrated. The crude was purified by silica gel column chromatography eluted with hexane/ethyl acetate to yield the desired product as an oil (0.57 g). MS (M+1)$^+$: 638.5.

Step 7-3, preparation of benzyl (2S)-2-({1-[6-(2-amino-5-cyanopyridin-3-yl)-3-(3-fluoro-5-methylphenyl)quinolin-4-yl]-N-methylformamido}methyl)pyrrolidine-1-carboxylate: to a mixture of the material from Step 7-2 (40 mg, 0.06 mmol), 6-amino-5-bromo-nicotinonitrile (14 mg, 0.07 mmol), Pd (amphos)Cl$_2$ (9 mg, 0.2 eq), K$_2$CO$_3$ (22 mg, 2.5 eq) dioxane/water (1 ml/0.1 ml) , N$_2$ was bubbled for 2 min, then sealed and heated at 100° C. for 1 h. The mixture was diluted with ethyl acetate and water. The organic layer was separated and concentrated, purified by silica gel chromatography eluted with hexane/ethyl acetate to yield the desired product (13.6 mg). MS (M+1)$^+$: 629.5.

Step 7-4, preparation of 6-(2-amino-5-cyanopyridin-3-yl)-3-(3-fluoro-5-methylphenyl)-N-methyl-N-[(2S)-pyrrolidin-2-ylmethyl]quinoline-4-carboxamide: the material from Step 7-3 was stirred in TFA (1 ml) in the presence of thioanisole (0.2 ml) for 1 h at 50° C. The mixture was then concentrated and purified by reversed phase C18 column chromatography to afford the desired product (9.5 mg, Compound 3-15). MS (M+1)$^+$: 495.5.

6-(5-cyano-2-hydroxypyridin-3-yl)-3-(3-fluoro-5-methylphenyl)-N-methyl-N-[(2S) -pyrrolidin-2-ylmethyl]quinoline-4-carboxamide (Compound 3-56) was prepared similarly according to Example 7, except at Step 7-4, hydroxyl group on side chain 5-cyano-2-hydroxy -pyridin-3-yl was produced from the corresponding 5-cyano-2-methoxyl-pyridin-3-yl group by treatment of TFA. MS (M+1)$^+$: 496.4.

The following compounds were prepared similarly to Example 7 with appropriate substituting reagents:

| Compound no. | MS (M + H)$^+$ |
|---|---|
| 3-13 | 480.4 |
| 3-14 | 480.3 |
| 3-16 | 480.4 |
| 3-19 | 481.3 |
| 1-40 | 547.3 |
| 1-41 | 504.2 |
| 1-43 | 514.4 |
| 3-22 | 508.3 |
| 1-49 | 526.3 |
| 3-33 | 526.4 |
| 3-35 | 498.3 |
| 3-37 | 509.4 |
| 3-38 | 523.3 |
| 1-53 | 515.4 |
| 1-54 | 515.5 |
| 3-39 | 494.6 |
| 1-60 | 533.2 |
| 3-41 | 511.6 |
| 3-44 | 499.3 |
| 3-46 | 512.5 |
| 3-50 | 533.2 |
| 3-51 | 470.4 |
| 1-66 | 551.3 |
| 3-52 | 533.2 |
| 1-70 | 528.1 |
| 3-57 | 512.5 |
| 3-62 | 488.5 |
| 3-65 | 469.5 |
| 3-66 | 509.6 |
| 3-71 | 456.3 |
| 3-67 | 486.4 |
| 3-72 | 565.5 |
| 3-73 | 578.3 |
| 3-74 | 473.3 |
| 3-75 | 489.3 |
| 3-77 | 502.4 |
| 3-78 | 515.6 |
| 1-76 | 536.4 |
| 1-77 | 495.5 |
| 3-79 | 516.4 |
| 3-80 | 498.3 |
| 3-81 | 485.4 |
| 3-82 | 543.0 |
| 3-83 | 469.6 |
| 3-84 | 485.4 |
| 3-85 | 504.3 |
| 3-86 | 521.3 |

Example 8: 6-(3-hydroxyphenyl)-N-methyl-3-(prop-1-yn-1-yl)-N-((2S)-pyrrolidin-2-ylmethyl)-1,5-naphthyridine-4-carboxamide

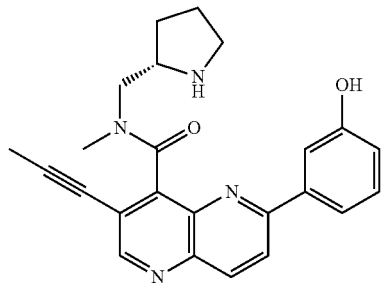 [SMILES: CC#Cc1cnc2ccc(-c3cccc(O)c3)nc2c1C(=O)N(C)C[C@@H]1CCCN1]

Step 8-1, preparation of benzyl (2S)-2-[(1-{6-[3-(benzyloxy)phenyl]-3-(prop-1-yn-1-yl)-1,5-naphthyridin-4-yl}-N-methylformamido)methyl]pyrrolidine-1-carboxylate: to benzyl (2S)-2-[(1-{6-[3-(benzyloxy)phenyl]-3-chloro-1,5-naphthyridin-4-yl}-N -methylformamido)methyl]pyrrolidine-1-carboxylate (240 mg, 0.39 mmol) from Example 4 in toluene (4 ml), tributyl (1-propynl)tin (0.37 ml, 3.0eq) was added. The mixture was bubbled with $N_2$ gas for 10 min, then Pd (amphos)$Cl_2$ (55 mg, 0.2 eq) was added and the mixture was sealed and heated at 90° C. for 2 h. Additional palladium catalyst (0.1 eq) and tin reagent (1.0 eq) were added. The mixture was stirred for another 2 hrs. The crude was diluted with ethyl acetate. The organic solution was washed with water, dried, concentrated and purified by silica gel chromatography eluted with ethyl acetate/hexanes to yield the desired product (131 mg). MS $(M+1)^+$: 625.6.

Step 8-2, preparation of 6-(3-hydroxyphenyl)-N-methyl-3-(prop-1-yn-1-yl)-N-((2S) -pyrrolidin-2-ylmethyl)-1,5-naphthyridine-4-carboxamide: the above material from Step 8-1 was stirred in TFA (2 ml) in the presence of thioanisole (0.2 ml) at 70° C. for 2 hrs, concentrated and purified by reversed phase C18 column. The desired fractions were collected and neutralized with aq $NaHCO_3$ solution. The product was extracted with ethyl acetate. HCl in ethyl ether (1 ml, 0.5 M) was added. Concentration gave the desired product as HCl salt (30 mg, Compound 3-18) as a yellow foam. MS $(M+1)^+$: 401.3.

6-(3-cyano-5-fluorophenyl)-N-methyl-3-(prop-1-yn-1-yl)-N-[(2S)-pyrrolidin-2-ylmethyl]-1,5-naphthyridine-4-carboxamide (Compound 3-7) was prepared similarly according to Example 8. MS $(M+1)^+$: 428.2.

Example 9: 6-(3-carbamoyl-5-fluorophenyl)-3-(3-fluoro-5-methylphenyl)-N-methyl-N -[(2S)-pyrrolidin-2-ylmethyl]quinoline-4-carboxamide

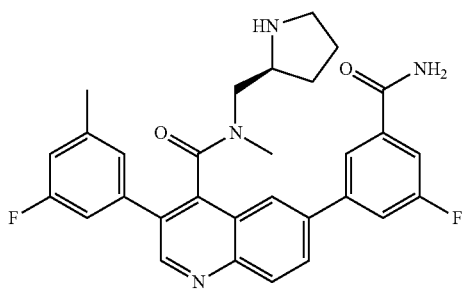 [SMILES: Cc1cc(F)cc(-c2cnc3ccc(-c4cc(F)cc(C(N)=O)c4)cc3c2C(=O)N(C)C[C@@H]2CCCN2)c1]

6-(3-cyano-5-fluorophenyl)-3-(3-fluoro-5-methylphenyl)-N-methyl-N-[(2S) -pyrrolidin-2-ylmethyl]quinoline-4-carboxamide (Compound 1-24, 20 mg, 0.04 mmol), was stirred with NaOH (4M, 1 ml) in a mxture of THF (0.5 ml) and MeOH (0.5 ml) at 70° C. for 1 h. The crude was extracted directly with a mixed solvents of MeOH/DCM (1/4). The extracted solution was concentrated and purified by reversed phase C18 column eluted with water/TFA (99.5%/0.5%) and acetonitrile/TFA (99.5%/0.5%) to afford the desired product (6 mg, TFA salt) as white powder (Compound 1-33). MS $(M+H)^+$: 515.2.

Similarly, N-[(2S)-2-aminopropyl]-6-(3-carbamoyl-5-methoxyphenyl)-3-(3-fluoro-5-methylphenyl)-N-methylquinoline-4-carboxamide (Compound 1-75) was obtained from N -[(2S)-2-aminopropyl]-6-(3-cyano-5-methoxyphenyl)-3-(3-fluoro-5-methylphenyl)-N -methylquinoline-4-carboxamide (Compound 1-19). MS $(M+H)^+$: 501.3.

Similarly, 6-(3-carbamoyl-5-fluorophenyl)-3-(3-fluoro-5-methylphenyl)-N-methyl-N -[(2S)-pyrrolidin-2-ylmethyl]-1,5-naphthyridine-4-carboxamide (Compound 2-24) was obtained from 6-(3-cyano-5-fluorophenyl)-3-(3-fluoro-5-methylphenyl)-N-methyl-N-[(2S)-pyrrolidin-2-ylmethyl]-1,5-naphthyridine-4-carboxamide (Compound 2-17). MS $(M+H)^+$: 516.4.

Example 10: 3-fluoro-5-[3-(3-fluoro-5-methylphenyl)-4-{methyl[(2S)-pyrrolidin-2-ylmethyl]carbamoyl}quinolin-6-yl]benzoic acid

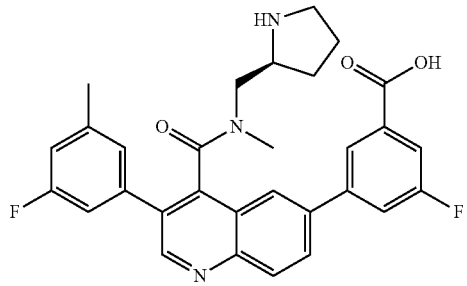 [SMILES: Cc1cc(F)cc(-c2cnc3ccc(-c4cc(F)cc(C(=O)O)c4)cc3c2C(=O)N(C)C[C@@H]2CCCN2)c1]

6-(3-cyano-5-fluorophenyl)-3-(3-fluoro-5-methylphenyl)-N-methyl-N-[(2S) -pyrrolidin-2-ylmethyl]quinoline-4-carboxamide (Example 1-24, 70 mg, 0.14 mmol, was stirred with NaOH (4M, 2 ml) in a mxture of THF (1 ml) and MeOH (1 ml) at 60-70° C. for 6 hrs. The crude was acidified to pH~3, then extracted with DCM. The extracted solution was concentrated and purified by reversed phase C18 column eluted with water/TFA (99.5%/0.5%) and acetonitrile/TFA (99.5%/0.5%) to afford the desired product (25 mg, TFA salt) as white powder (Compound 1-36). MS $(M+H)^+$: 516.4.

Example 11: 3-[3-(3-fluoro-5-methylphenyl)-4-{methyl[(2S)-pyrrolidin-2-ylmethyl]carbamoyl}quinolin-6-yl]benzoic acid

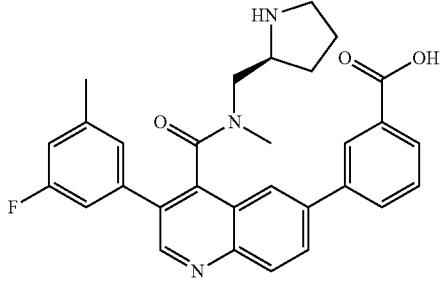 [SMILES: Cc1cc(F)cc(-c2cnc3ccc(-c4cccc(C(=O)O)c4)cc3c2C(=O)N(C)C[C@@H]2CCCN2)c1]

Example 12: 6-(3-cyano-5-fluorophenyl)-3-[3-fluoro-5-(2-hydroxyethoxy)phenyl]-N-methyl-N-[(2S)-pyrrolidin-2-ylmethyl]quinoline-4-carboxamide

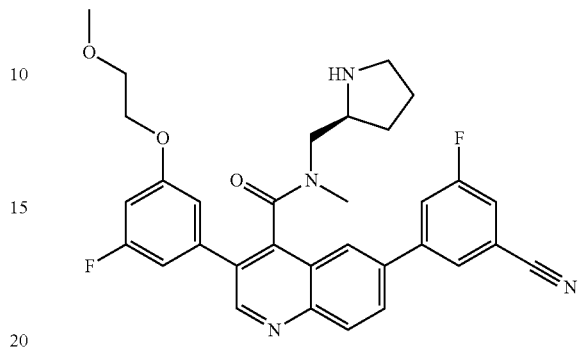

Step 11-1, preparation of benzyl (2S)-2-({1-[3-(3-fluoro-5-methylphenyl)-6-[3-(methoxycarbonyl)phenyl]quinolin-4-yl]-N-methylformamido}methyl)pyrrolidine-1-carboxylate: to a mixture of benzyl (2S)-2-({1-[3-(3-fluoro-5-methylphenyl)-6-(tetramethyl-1,3,2-dioxaborolan-2-yl)quinolin-4-yl]-N-methylformamido}methyl)pyrrolidine-1-carboxylate: (30 mg, 0.046 mmol), 3-bromo-benzoic acid methyl ester (11.2 mg, 0.05 mmol), Pd (amphos)Cl₂ (6.6 mg, 0.2 eq), K₂CO₃ (16 mg, 2.5 eq) in dioxane/water (1 ml/0.1 ml) N₂ was bubbled for 2 min, then sealed and heated at 100° C. for 1 h. The mixture was diluted with ethyl acetate and water. The organic layer was separated and concentrated, purified by silica gel chromatography eluted with hexane/ethyl acetate to yield the desired product as a white foam (11 mg), MS (M+H)⁺: 512.5.

Step 11-2, preparation of 3-[3-(3-fluoro-5-methylphenyl)-4-{methyl[(2S)-pyrrolidin-2-ylmethyl]carbamoyl}quinolin-6-yl]benzoic acid: the above material was stirred in TFA (1 ml) in the presence of thioanisole (0.2 ml) at 50° C. for 1 h, then concentrated and stirred in a mixture of 4N NaOH (1 ml) in the presence of THF (1 ml) and MeOH (1 ml) at 60° C. for 1 h. The mixture was acidified and extracted out with a mixture of DCM/MeOH (4/1). The extract was concentrated and purified by reversed phase C18 column eluted with water/TFA (99.5%/0.5%) and acetonitrile/TFA (99.5%/0.5%) to afford the desired product (2.5 mg, TFA salt, Compound 1-44). MS (M+H)⁺: 498.3.

The following compounds were prepared similarly to Example 11 with appropriate substituting reagents:

| Compound no. | MS (M + H)⁺ |
| --- | --- |
| 1-46 | 498.4 |
| 1-47 | 498.4 |
| 1-48 | 512.4 |
| 1-50 | 526.4 |

Step 12-1, preparation of benzyl (2S)-2-({1-[6-(3-cyano-5-fluorophenyl)-3-(3-fluoro-5-hydroxyphenyl)quinolin-4-yl]-N-methylformamido}methyl)pyrrolidine-1-carboxylate: titile compound is obtained according to the method in Example 2 with appropriate substituting reagents. MS (M+H)⁺: 633.3.

Step 12-2, preparation of benzyl (2S)-2-({1-[6-(3-cyano-5-fluorophenyl)-3-[3-fluoro-5-(2-methoxyethoxy)phenyl]quinolin-4-yl]-N-methylformamido}methyl)pyrrolidine-1-carboxylate: a mixture of the material prepared from Step 12-1 (32 mg, 0.05 mmol) in DMF (1 ml) was stirred with K₂CO₃ (34.5 mg, 0.25 mmol) and 1-bromo-2-methoxy-ethane (0.05 ml, 0.5 mmol) at 80° C. for 2 h. The crude was extracted with ethyl acetate. The extract was washed with water, dried and concentrated, purified by silica gel column chromatography to give the desired product (30 mg). MS (M+H)⁺: 691.3.

Step 12-3, preparation of 6-(3-cyano-5-fluorophenyl)-3-[3-fluoro-5-(2-hydroxyethoxy)phenyl]-N-methyl-N-[(2S)-pyrrolidin-2-ylmethyl]quinoline-4-carboxamide: the above material from Step 12-2 was stirred at 65° C. in TFA (1 ml) in the presence of thioanisole (0.1 ml) for 1 h. The mixture was concentrated and purified by reverse phase C18 column chromatography eluted with water/TFA (99.5%/0.5%) and acetonitrile/TFA (99.5%/0.5%) to afford the desired product (15 mg, Compound 1-42). MS (M+H)⁺: 557.3.

6-(3-cyano-5-fluorophenyl)-3-[3-fluoro-5-(2-hydroxyethoxy)phenyl]-N-methyl-N-[(2S)-pyrrolidin-2-ylmethyl]quinoline-4-carboxamide (Compound 1-39) was prepared similarly according to the method in Example 12 with appropriating reagents. MS (M+1)⁺: 543.2.

4-{3-[6-(3-cyano-5-fluorophenyl)-4-{methyl[(2S)-pyrrolidin-2-ylmethyl]carbamoyl}quinolin-3-yl]-5-fluorophenoxy}butanoic acid (Compound 1-37) was prepared similarly according to the method in Example 12 with appropriating reagents and with an additional hydrolysis step of the ester. MS (M+1)⁺: 585.3.

2-{3-fluoro-5-[3-(3-fluoro-5-methylphenyl)-4-{methyl[(2S)-pyrrolidin-2-ylmethyl]carbamoyl}quinolin-6-yl]phenyl}acetic acid (Compound 1-59) was prepared similarly according to the method in Example 12 with appropriating reagents and with an additional hydrolysis step of the ester. MS (M+1)⁺: 530.2.

2-{3-chloro-5-[6-(3-cyano-5-fluorophenyl)-4-{methyl[(2S)-pyrrolidin-2-ylmethyl]carbamoyl}quinolin-3-yl]phenoxy}acetic acid (Compound 1-65) was prepared similarly according to the method in Example 12 with appropriating reagents and with an additional hydrolysis step of the ester. MS (M+1)+: 573.3.

Example 13: 6-(3-cyano-5-fluorophenyl)-3-(2-fluoro-3,5-dimethylphenyl)-N-methyl-N -[(2S)-pyrrolidin-2-ylmethyl]quinoline-4-carboxamide

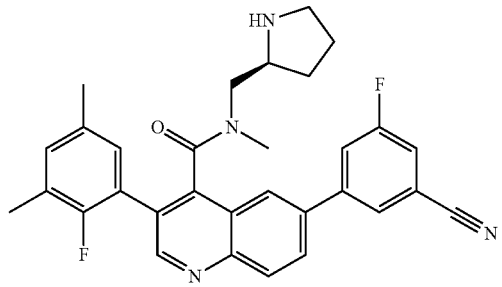 [SMILES: Cc1cc(C)c(F)c(-c2cnc3ccc(-c4cc(F)cc(C#N)c4)cc3c2C(=O)N(C)C[C@@H]2CCCN2)c1]

Step 13-1, preparation of 6-chloro-3-methoxymethoxy-quinoline-4-carboxylic acid: a mixture of 6-chloro-3-methoxymethoxy-quinoline-4-carboxylic acid methyl ester (2.0 g, 7.1 mmol) in THF/MeOH (5 ml/5 ml) was stirred with 4 N NaOH (10 ml) at 70° C. until TLC showed no starting material left. The mixture was acidified and extracted with ethyl acetate, dried and concentrated to give a white solid (0.8 g). MS (M+1)+: 268.3.

Step 13-2, preparation of benzyl (2S)-2-({1-[6-chloro-3-(methoxymethoxy)quinolin-4-yl]-N-methylformamido}methyl)pyrrolidine-1-carboxylate: a mixture of the acid obtained from Step 13-1, HATU (1.71 g, 4.5 mmol), (S)-2-methylaminomethyl-pyrrolidine-1-carboxylic acid benzyl ester (0.9 g, 3.6 mmol), TEA (1.0 ml, 6 mmol) were stirred in DMF (15 ml) for 1 h. The mixture was diluted with water and extracted with ethyl acetate. Ethyl acetate layer was then dried, concentrated and purified by silica gel chromatography eluted with DCM/ethyl acetate to give the desired product (1.4 g) as a brown oil. MS (M+1)+: 498.3.

Step 13-3, preparation of benzyl (2S)-2-({1-[6-(3-cyano-5-fluorophenyl)-3-(ethoxymethoxy)quinolin-4-yl]-N-methylformamido}methyl)pyrrolidine-1-carboxylate: To the material from Step 13-2 (0.7 g, 1.4 mmol) in a mixture of dioxane (7 ml) and water (0.7 ml), 3-cyano-5-fluoro-phenyl boronic acid (462 mg, 2.8 mmol), K₂CO₃ (386 mg, 2.8 mmol) were added. The solution was bubbled with N₂ for 10 min, then Pd (amphos)Cl₂ (35 mg, 0.05 mmol) was added. The mixture was sealed and heated with stirring at 95° C. for 2 hrs. Additional boronic acid (1 mmol) and Pd (amphos)Cl₂ (15 mg), K₂CO₃ (1 mmol) were added. It was heated for another 1 hr, extracted with ethyl acetate. The ethyl acetate was concentrated and the crude was purified by silica column chromatography eluted with DCM/ethyl acetate to give the desired product (640 mg). MS (M+1)+: 583.2.

Step 13-4, preparation of benzyl (2S)-2-({1-[6-(3-cyano-5-fluorophenyl)-3-(trifluoromethanesulfonyloxy)quinolin-4-yl]-N-methylformamido}methyl)pyrrolidine-1-carboxylate: the above material from Step 13-3 was stirred in isopropanol containing 7N HCl (7 ml) for 3 hrs, and concentrated to yield a yellow solid. The solid was then dissolved in DCM (7 ml), cooled to 0° C., followed by addition of TEA (0.8 ml, 4.4 mmol) and trifluoromethane-sulfonic anhydride (0.4 mmol, 2.2 mmol). The mixture was stirred at rt for 1 hr and diluted with water and extracted with ethyl acetate. The ethyl acetate was concentrated and the crude was purified by silica gel column chromatography eluted with hexane/ethyl acetate to yield the desired product (517 mg). MS (M+1)+: 671.5.

Step 13-5, preparation of benzyl (2S)-2-({1-[6-(3-cyano-5-fluorophenyl)-3-(2-fluoro -3,5-dimethylphenyl)quinolin-4-yl]-N-methylformamido}methyl)pyrrolidine-1-carboxylate: the desired product (30 mg) was obtained by following the method outlined in Step 13-3 with the material made in Step 13-4 (55 mg) and 3,5-dimethyl-2-fluorophenylboronic acid, pinacol ester (50 mg). MS (M+1)+: 645.7.

Step 13-5, preparation of 6-(3-cyano-5-fluorophenyl)-3-(2-fluoro-3,5-dimethylphenyl) -N-methyl-N-[(2S)-pyrrolidin-2-ylmethyl]quinoline-4-carboxamide: the material from the above step was heated in TFA (1.5 ml) in the presence of thioanisole (0.15 ml) for 1 hr, concentrated and purified by reversed phase C18 column to give the desired product as TFA salt which was then diluted with ethyl acetate and washed with sat NaHCO₃ aqueous solution (1 ml) , and then treated with 4 N HCl in dioxane (0.1 ml) to form HCl salt (15 mg, Compound 3-34). MS (M+1)+: 511.4.

The following compounds were prepared similarly to Example 13 with appropriate substituting reagents:

| Compound no. | MS (M + H)+ |
| --- | --- |
| 1-56 | 501.1 |
| 1-57 | 513.4 |
| 1-58 | 497.4 |
| 1-67 | 501.3 |
| 1-69 | 541.3 |

6-(3-cyano-5-fluorophenyl)-3-[3-fluoro-5-(prop-1-en-2-yl)phenyl]-N-methyl-N-[(2S) -pyrrolidin-2-ylmethyl]quinoline-4-carboxamide (Compound 1-71) was obtained as side product during the preparation of 6-(3-cyano-5-fluorophenyl)-3-[3-fluoro-5-(2-hydroxypropan -2-yl)phenyl]-N-methyl-N-[(2S)-pyrrolidin-2-ylmethyl]quinoline-4-carboxamide (Compound 1-69).

Example 14: 6-(3,5-difluorophenyl)-3-(3-fluoro-5-methylphenyl)-N-methyl-N-[(2S) -pyrrolidin-2-ylmethyl]quinoline-4-carboxamide

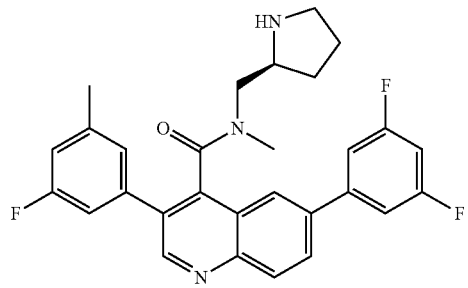 [SMILES: Cc1cc(F)cc(-c2cnc3ccc(-c4cc(F)cc(F)c4)cc3c2C(=O)N(C)C[C@@H]2CCCN2)c1]

Step 14-1: preparation of 6-(3,5-difluoro-phenyl)-3-(3-fluoro-5-methyl-phenyl) -quinoline-4-carboxylic acid methyl ester: a mixture of 6-chloro-3-(3-fluoro-5-methyl-phenyl) -quinoline-4-carboxylic acid methyl ester from Step 2-1 of Example 2 (0.9 g, 2.7 mmol) and the 3,5-difluoro-phenyl boronic acid (0.86 g, 2.0 eq.), Pd (amphos)Cl₂ (250 mg), and K₂CO₃ (750 mg, 2 eq.) in dioxane containing 10% of water (22 ml) was degassed by N2 for 3 min and sealed, heated at 90° C. for 2 hrs. The mixture was diluted with ethyl acetate. The ethyl acetate layer was then washed with 1N HCl, brine and concentrated. The crude oil was purified by silica gel chromatography to afford the title compound (1.0g). MS (M+1)+: 408.3.

Step 14-2: preparation of 6-(3,5-difluoro-phenyl)-3-(3-fluoro-5-methyl-phenyl) -quinoline-4-carboxylic acid: A mixture of the ester from Step 14-1 (0.9 g, 2.2 mmol) and NaOH (4 N, 5.5 ml, 10 eq.) in THF/water (10 ml/3 ml) was stirred at 60° C. overnight, then concentrated to remove volatile. The residue was acidified with 1 N HCl to form a precipitate, which was filtered, washed with water, dried to afford the title compound (0.7 g). MS (M+1)+: 394.1.

Step 14-3: preparation of tert-butyl (2S)-2-({1-[6-(3,5-difluorophenyl)-3-(3-fluoro-5-methylphenyl)quinolin-4-yl]-N-methylformamido}methyl)pyrrolidine-1-carboxylate: a mixture of the acid from Step 14-2 (30 mg, 0.076 mmol), HATU (44 mg, 1.5 eq) and triethylamine (30 ml, 3.0 eq.) in DMF (1.5 ml) was stirred at r.t for 5 min, then (S)-2-methylaminomethyl -pyrrolidine-1-carboxylic acid tert-butyl ester (20 mg, 1.2 eq) was added. The mixture was stirred for another 2 hrs, then diluted with ethyl acetate, washed with 1N HCl, dried and concentrated. The crude was purified by silica gel chromatography to afford the title compound (30 mg). MS (M+1)+: 590.4.

Step 14-4, preparation of 6-(3,5-difluorophenyl)-3-(3-fluoro-5-methylphenyl)-N -methyl-N-[(2S)-pyrrolidin-2-ylmethyl]quinoline-4-carboxamide: the product from the above step was stirred in a mixture of DCM (1.5 ml) and TFA (0.15 ml) for 2 hr at r,t. The mixture was then concentrated and purified by RP C18 column to yield the titled compound (10 mg, Compound 1-62). MS (M+1)+: 490.3.

The following compounds were prepared similarly to Example 14 with appropriate substituting reagents:

| Compound no. | MS (M + H)+ |
|---|---|
| 1-61 | 476.4 |
| 1-63 | 494.3 |
| 1-64 | 518.5 |
| 3-53 | 485.4 |
| 1-68 | 492.4 |

Example 15: 6-(3-cyano-5-fluorophenyl)-N-methyl-3-(3-methylbutyl)-N-[(2S)-pyrrolidin-2-ylmethyl]-1,5-naphthyridine-4-carboxamide

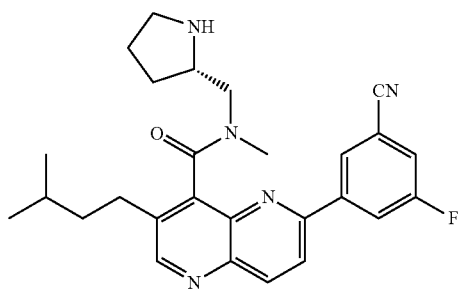 [SMILES: CC(C)CCc1cnc2ccc(-c3cc(F)cc(C#N)c3)nc2c1C(=O)N(C)C[C@@H]1CCCN1]

To benzyl (2S)-2-({1-[3-chloro-6-(3-cyano-5-fluorophenyl)-1,5-naphthyridin-4-yl]-N -methylformamido}methyl) pyrrolidine-1-carboxylate (30 mg, 0.054 mmol), prepared according to the methods provided in Example 4 (Step 4-3) with 3-cyano-5-fluorophenylboronic acid as substitution, in anhydrous THF (3 ml), Pd(t-Bu₃P)₂ (11 mg, 0.022 mmol) and 3-methylbutylzinc bromide solution (0.5M in THF, 0.32 ml, 0.16 mmol) were added. The mixture was bubbled with N₂ for 5 min and then sealed and heated at 95° C. overnight. The mixture was then diluted with water, extracted with ethyl acetate, concentrated and purified by silica gel chromatography and reversed phased C18 column chromatography to afford benzyl (2S)-2-({1-[6-(3-cyano-5-fluorophenyl)-3-(3-methylbutyl)-1,5-naphthyridin-4-yl]-N -methylformamido}methyl)pyrrolidine-1-carboxylate (3.5 mg) as a white solid. MS (M+1)+: 594.4. The solid was then stirred with TFA in the presence of thioanisole (0.25 ml/0.05 ml) at 60° C. for 2 hrs and then purified by reversed phase C18 column chromatography to afford the title compound as TFA salt (1.1 mg) as off-white gum (Compound 3-43). MS (M+1)+: 460.3.

Example 16: 6-[3-(carbamoylmethyl)-5-fluorophenyl]-3-(3-fluoro-5-methylphenyl)-N -methyl-N-[(2S)-pyrrolidin-2-ylmethyl]quinoline-4-carboxamide

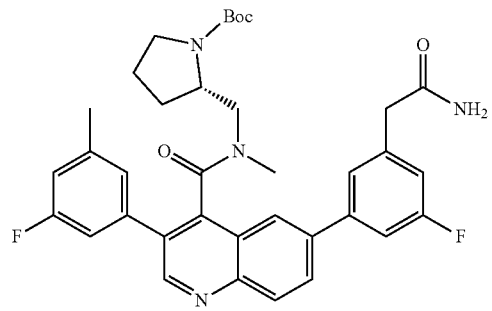 [SMILES: Cc1cc(F)cc(-c2cnc3ccc(-c4cc(F)cc(CC(N)=O)c4)cc3c2C(=O)N(C)C[C@@H]2CCCN2C(=O)OC(C)(C)C)c1]

A mixture of 2-{3-[4-({[(2S)-1- [(tert-butoxy)carbonyl] pyrrolidin-2-yl]methyl}(methyl)carbamoyl)-3-(3-fluoro-5-methylphenyl)quinolin-6-yl]-5-fluorophenyl}acetic acid (21 mg, 0.027 mmol), obtained according to Step 7-3 of Example 7 with (3-bromo-5-fluoro-phenyl)-acetic acid as coupling reagent, DIPEA (0.05 ml, 10 eq), HATU (31 mg, 0.041 mmol, 1.5 eq) in DMF (3 ml) was stirred at rt for 5 min, then NH₄Cl (7.4 mg, 0.14 mmol, 5 eq) was added. The mixture was stirred overnight and another partions of HATU (76 mg), DIPEA (0.1 ml) and NH₄Cl (7.4 mg) were added. The mixture was stirred for another 24 hrs and directly purified by reversed phase C18 column chromatography to afford tert-butyl (2S)-2- [(1-{6-[3-(carbamoylmethyl)-5-fluorophenyl]-3-(3-fluoro-5-methylphenyl)quinolin-4-yl}-N-methylformamido)methyl]pyrrolidine-1-carboxylate (9.5 mg). MS (M+1)+: 663.4. The above material was treated with TFA in the presence of thioanisole according to the previously described procedure to afford the title compound (2.2 mg, Compound 1-74). MS (M+1)+: 529.3.

Example A-1: Parenteral Pharmaceutical Composition

To prepare a parenteral pharmaceutical composition suitable for administration by injection (subcutaneous, intravenous), 1-100 mg of a water-soluble salt of a compound Formula (I), or a pharmaceutically acceptable salt or solvate thereof, is dissolved in sterile water and then mixed with 10 mL of 0.9% sterile saline. A suitable buffer is optionally added as well as optional acid or base to adjust the pH. The mixture is incorporated into a dosage unit form suitable for administration by injection Example A-2: Oral Solution To prepare a pharmaceutical composition for oral delivery, a sufficient amount of a compound of Formula (I), or a pharmaceutically acceptable salt thereof, is added to water (with optional solubilizer(s), optional buffer(s) and taste masking excipients) to provide a 20 mg/mL solution.

Example A-3: Oral Tablet

A tablet is prepared by mixing 20-50% by weight of a compound of Formula (I), or a pharmaceutically acceptable salt thereof, 20-50% by weight of microcrystalline cellulose, 1-10% by weight of low-substituted hydroxypropyl cellulose, and 1-10% by weight of magnesium stearate or other appropriate excipients. Tablets are prepared by direct compression. The total weight of the compressed tablets is maintained at 100-500 mg.

Example A-4: Oral Capsule

To prepare a pharmaceutical composition for oral delivery, 10-500 mg of a compound of Formula (I), or a pharmaceutically acceptable salt thereof, is mixed with starch or other suitable powder blend. The mixture is incorporated into an oral dosage unit such as a hard gelatin capsule, which is suitable for oral administration.

In another embodiment, 10-500 mg of a compound of Formula (I), or a pharmaceutically acceptable salt thereof, is placed into Size 4 capsule, or size 1 capsule (hypromellose or hard gelatin) and the capsule is closed.

Example A-5: Topical Gel Composition

To prepare a pharmaceutical topical gel composition, a compound of Formula (I), or a pharmaceutically acceptable salt thereof, is mixed with hydroxypropyl celluose, propylene glycol, isopropyl myristate and purified alcohol USP. The resulting gel mixture is then incorporated into containers, such as tubes, which are suitable for topical administration.

Example B-1: SSTR Assays

Membrane Preparation:

Crude membrane fractions are prepared from Chinese hamster ovary (CHO) cells stably expressing one of the five human or rodent somatostatin receptor subtypes. The cells are grown to 85-100% confluence on standard tissue culture dishes in DM-MEM growth media (Gibco) with following additives: 10% fetal bovine serum (Gibco), 100 U/mL penicillin (Gibco), 100 ug/mL streptomycin (Gibco), 10 mM HEPES (Gibco), 0.5 mg/mL G-418 (Gibco). To prepare membranes, cells are washed once with 1X Dulbecco's phosphate buffered saline (Gibco) containing 10 mM HEPES (Gibco) then once with sodium free binding buffer (50 mM Tris Base, 5 mM $MgCl_2$-$6H_2O$ and 1 mM EGTA adjusted to pH 7.8). The cells are then scraped into binding buffer containing a protease inhibitor cocktail (100 ug/mL pepstatin A (Sigma), 50 ug/mL leupeptin (Sigma), 25 ug/mL aprotinin (Sigma) and 10 mg/mL Bacitracin (USB Corporation)). The cells are centrifuged at 43,500×g, homogenized, and the resulting membranes are collected by centrifugation at 67,000×g. The membranes are then resuspended in binding buffer containing the protease inhibitor cocktail using a glass dounce homogenizer.

Functional Assay for SSTR2 Agonists

General overview: All five SSTR subtypes are Gi coupled G-protein coupled receptors (GPCRs) that lead to decreases in intracellular cyclic AMP (cAMP) when activated by an agonist. Therefore, measurement of intracellular cAMP levels can be used to assess whether compounds of the invention are agonists of SSTR subtypes (John Kelly, Troy Stevens, W. Joseph Thompson, and Roland Seifert, *Current Protocols in Pharmacology,* 2005,2.2.1-2.2). One example of an intracellular cAMP assay is described below.

cAMP Assay Protocol:

One day prior to the assay, 40,000 Chinese hamster ovary (CHO) cells expressing the human somatostatin receptor subtype 2 are plated in each well of a 96-well tissue culture plate in DM-MEM growth media (Gibco) with the following additives: 10% fetal bovine serum (Gibco), 100 U/mL penicillin (Gibco), 100 ug/mL streptomycin (Gibco), 10 mM HEPES (Gibco), 1.2 mM sodium hydroxide, 0.5 mg/mL G-418 (Gibco)). The cells are cultured overnight at 37° C., 5% $CO_2$ and 95% humidity. On the day of the assay, the media is aspirated and the cells are washed with 1X Dulbecco's phosphate buffered saline (Gibco). Next, 5 µL of assay buffer (1× Earle's Balanced Salt Solution (Gibco), 5 mM $MgCl_2$, 10 mM HEPES, 0.1% bovine serum albumin, 0.2 mM 3-Isobutyl-1-methylxanthine (IBMX, Biomol Research Labs)) and forskolin is added. Various dilutions of the compounds of the invention are prepared in assay buffer and 5 µL of the dilutions are added to the cultured cells and incubated for 15 minutes at 37° C. (the final concentration of the compounds of the invention are typically 0-10,000 nM). 10 µL of lysis buffer (HRTF cAMP kit, Cisbio) containing cAMP detection and visualization antibodies are added and the assay is allowed incubate for 1-24 hours at room temperature. The intracellular cAMP concentrations are then measured using a commercially available detection kit (for example, the cAMP HTRF kit, Cisbio). The measured intracellular cAMP concentrations are plotted vs. the concentration of the compounds of the invention and the $EC_{50}$ of the compounds are calculated using standard methods.

Illustrative biological activity of compounds is demonstrated by evaluating the inhibition of cAMP activities via sst2 receptor. Compounds having $EC_{50}$ between 100 nM and 1,000 nM include 1-8, 1-73, 2-2, 2-4, 2-8, 2-15, 2-20, 2-21, 2-22, 3-2, 3-3, 3-5, 3-7, 3-10, 3-11, 3-12, 3-17, 3-18, 3-42, 3-47, 3-49, 3-54, 3-55, 3-69, 3-70, 3-76. Compounds having $EC_{50}$ below 100 nM include 1-1 to 1-7, 1-9 to 1-72, 1-74 to 1-78, 2-1, 2-3, 2-5, 2-6, 2-7, 2-9 to 2-14, 2-16 to 2-19, 2-23, 2-24, 3-1, 3-4, 3-6, 3-8, 3-9, 3-13 to 3-16, 3-19 to 3-41, 3-43 to 3-46, 3-48, 3-50 to 3-53, 3-56 to 3-68, 3-71 to 3-75, 3-77 to 3-86. A general preference for the S-stereochemistry at the diamino position of the compounds of Formula (I) was observed versus the corresponding R-stereochemistry. For example, the $EC_{50}$ of S isomer (1-1) is 0.12 nM, while $EC_{50}$ of its corresponding R isomer (1-5) is 39 nM in human sst2 receptor cAMP assay.

The examples and embodiments described herein are for illustrative purposes only and various modifications or changes suggested to persons skilled in the art are to be included within the spirit and purview of this application and scope of the appended claims.

What is claimed is:

1. A compound that has the structure of Formula (I), or a pharmaceutically acceptable salt, solvate, diastereomeric mixture, or individual enantiomers thereof:

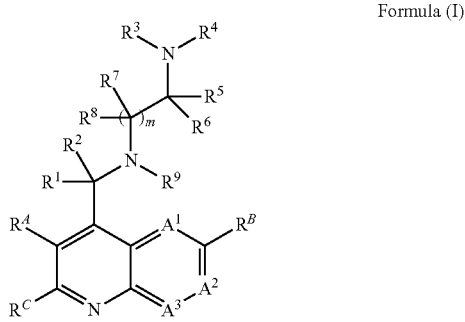

Formula (I)

wherein:

$R^1$ and $R^2$ are taken together with the carbon atom to which they are attached to form —C(=O)—;

or $R^1$ and $R^2$ are each independently selected from the group consisting of hydrogen, and unsubstituted or substituted $C_1$-$C_6$alkyl;

$R^A$ is a cyclic ring that is an unsubstituted or substituted monocyclic carbocycle, unsubstituted or substituted bicyclic carbocycle, unsubstituted or substituted monocyclic heterocycle, or unsubstituted or substituted bicyclic heterocycle, wherein if $R^A$ is substituted then $R^A$ is substituted with 1-2 $R^{10}$ and 0-2 $R^{11}$;

$R^B$ is a cyclic ring that is an unsubstituted or substituted monocyclic carbocycle, unsubstituted or substituted bicylcic carbocycle, unsubstituted or substituted monocyclic heterocycle, unsubstituted or substituted bicyclic heterocycle, wherein if $R^B$ is substituted then $R^B$ is substituted with 1-2 $R^{12}$ and 0-2 $R^{13}$;

$A^1$, $A^2$, and $A^3$ are independently $CR^C$ or N;

each $R^C$ is independently hydrogen, F, Cl, Br, methyl, ethyl, n-propyl, i-propyl, n-butyl, i-butyl, sec-butyl, tert-butyl, monofluoromethyl, difluoromethyl, trifluoromethyl, methoxy, ethoxy, trifluoromethoxy, —CN, —OH, —CO$_2$R$^{14}$, —C(=O)NR$^{14}$R$^{15}$, —C(=NOR$^{14}$)R$^{15}$, —SR$^{14}$, —S(=O)(C$_1$-C$_4$alkyl), —SO$_2$(C$_1$-C$_4$alkyl) or —SO$_2$NR$^{14}$R$^{15}$;

$R^3$ and $R^4$ are independently hydrogen, unsubstituted or substituted $C_1$-$C_6$ alkyl, unsubstituted or substituted $C_1$-$C_6$fluoroalkyl, or unsubstituted or substituted $C_3$-$C_6$cycloalkyl, wherein any substituted group of $R^3$ and $R^4$ is substituted with 1-4 $R^{16}$;

or $R^3$ and $R^4$ are taken together with the nitrogen atom to which they are attached to form an unsubstituted or substituted monocyclic or bicyclic heterocyclic ring, wherein if the heterocyclic ring is substituted then the heterocyclic ring is substituted with 1-4 $R^{16}$;

$R^5$, $R^6$, $R^7$, and $R^8$ are each independently selected from the group consisting of hydrogen, unsubstituted or substituted $C_1$-$C_6$ alkyl, unsubstituted or substituted $C_1$-$C_6$fluoroalkyl, unsubstituted or substituted monocyclic carbocycle, and unsubstituted or substituted monocyclic heterocycle, wherein any substituted group of $R^5$, $R^6$, $R^7$, and $R^8$ is substituted with 1-4 $R^{16}$;

$R^9$ is hydrogen, unsubstituted or substituted $C_1$-$C_6$ alkyl, unsubstituted or substituted benzyl, wherein if $R^9$ is substituted then $R^9$ is substituted with 1-4 $R^{16}$;

or $R^4$ and any one of $R^5$, $R^7$, or $R^9$ are taken together with the intervening atoms to which they are attached to form an unsubstituted or substituted monocyclic 4- to 7-membered heterocyclic ring or an unsubstituted or substituted bicyclic 9- to 12-membered heterocyclic ring, wherein if the heterocyclic ring is substituted then the heterocyclic ring is substituted with 1-4 $R^{16}$;

or $R^5$ and any one of $R^6$, $R^7$ or $R^9$ are taken together with the intervening atoms to which they are attached to form an unsubstituted or substituted monocyclic 4- to 7-membered ring or a bicyclic 9- to 12-membered ring, wherein if the heterocyclic ring is substituted then the heterocyclic ring is substituted with 1-4 $R^{16}$;

or $R^7$ and $R^9$ are taken together with the intervening atoms to which they are attached to form an unsubstituted or substituted monocyclic 4- to 7-membered heterocyclic ring or an unsubstituted or substituted bicyclic 9- to 12-membered heterocyclic ring, wherein if the heterocyclic ring is substituted then the heterocyclic ring is substituted with 1-4 $R^{16}$;

each $R^{10}$, $R^{11}$, $R^{12}$ and $R^{13}$ is independently hydrogen, halogen, unsubstituted or substituted $C_1$-$C_4$alkyl, unsubstituted or substituted $C_1$-$C_4$alkoxy, unsubstituted or substituted $C_1$-$C_4$fluoroalkyl, unsubstituted or substituted $C_1$-$C_4$fluoroalkoxy, unsubstituted or substituted monocyclic carbocycle, unsubstituted or substituted monocyclic heterocycle, —CN, —OH, —CO$_2$R$^{14}$, —CH$_2$CO$_2$R$^{14}$, —C(=O)NR$^{14}$R$^{15}$, —CH$_2$C(=O)NR$^{14}$R$^{15}$, —NR$^{14}$R$^{15}$, —CH$_2$NR$^{14}$R$^{15}$, —NR$^{14}$C(=O)R$^{15}$, —CH$_2$NR$^{14}$C(=O)R$^{15}$, —SR$^{14}$, —S(=O)R$^{15}$, —SO$_2$R$^{15}$, or —SO$_2$NR$^{14}$R$^{15}$, wherein if any group of $R^{10}$, $R^{11}$, $R^{12}$ and $R^{13}$ is substituted then the substituted group of $R^{10}$, $R^{11}$, $R^{12}$ and $R^{13}$ is substituted with 1-4 $R^{16}$;

each $R^{16}$ is independently halogen, $C_1$-$C_6$alkyl, heterocycle, —CN, —OR$^{14}$, —CO$_2$R$^{14}$, —C(=O)NR$^{14}$R$^{15}$, —NR$^{14}$R$^{15}$, —NR$^{14}$C(=O)R$^{15}$, —SR$^{14}$, —S(=O)R$^{15}$, —SO$_2$R$^{15}$, or —SO$_2$NR$^{14}$R$^{15}$;

each $R^{14}$ is independently selected from H, unsubstituted or substituted $C_1$-$C_6$alkyl, unsubstituted or substituted $C_1$-$C_6$heteroalkyl, unsubstituted or substituted $C_3$-$C_{10}$cycloalkyl, substituted or unsubstituted $C_2$-$C_{10}$heterocycloalkyl, substituted or unsubstituted aryl, and substituted or unsubstituted heteroaryl;

each $R^{15}$ is independently selected from H, unsubstituted or substituted $C_1$-$C_6$alkyl, unsubstituted or substituted $C_1$-$C_6$heteroalkyl, unsubstituted or substituted $C_3$-$C_{10}$cycloalkyl, substituted or unsubstituted $C_2$-$C_{10}$heterocycloalkyl, substituted or unsubstituted aryl, and substituted or unsubstituted heteroaryl; or $R^{14}$ and $R^{15}$ are taken together with the N atom to which they are attached to a substituted or unsubstituted N-containing heterocycle; and m is 1, 2, 3, or 4.

2. The compound of claim 1, or a pharmaceutically acceptable salt, solvate, diastereomeric mixture, or individual enantiomers thereof, wherein:

$R^1$ and $R^2$ are taken together with the carbon atom to which they are attached to form —C(=O)—; and m is 1 or 2.

3. The compound of claim 1, or a pharmaceutically acceptable salt, solvate, diastereomeric mixture, or individual enantiomers thereof, wherein:
$A^1$, $A^2$, and $A^3$ are $CR^C$;
or $A^1$ is N; and $A^2$ and $A^3$ are $CR^C$;
or $A^1$ and $A^3$ are $CR^C$; and $A^2$ is N;
or $A^1$ and $A^2$ are $CR^C$; and $A^3$ is N;
or $A^1$ and $A^2$ are N; and $A^3$ is $CR^C$;
or $A^1$ and $A^3$ are N; and $A^2$ is $CR^C$.

4. The compound of claim 1, or a pharmaceutically acceptable salt, solvate, diastereomeric mixture, or individual enantiomers thereof, wherein:
$R^3$ and $R^4$ are each independently selected from the group consisting of hydrogen, unsubstituted or substituted $C_1$-$C_6$ alkyl, and unsubstituted or substituted $C_1$-$C_6$ fluoroalkyl, wherein any substituted group of $R^3$ and $R^4$ is substituted with 1-4 $R^{16}$.

5. The compound of claim 1, wherein the compound of Formula (I) has the structure of Formula (Ia), Formula (Ib), Formula (Ic), Formula (Id), Formula (Ie), or Formula (If), or a pharmaceutically acceptable salt, solvate, diastereomeric mixture, or individual enantiomers thereof:

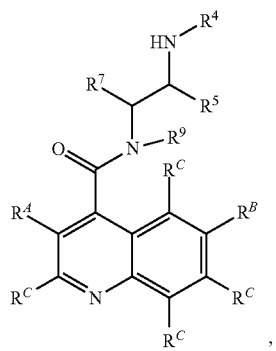

Formula (Ia)

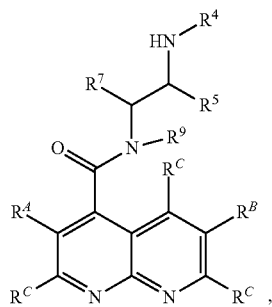

Formula (Ib)

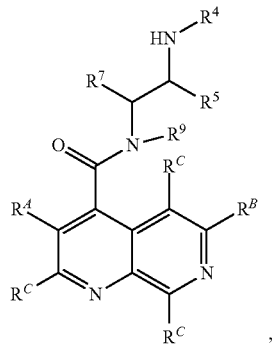

Formula (Ic)

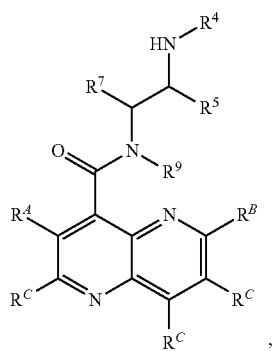

Formula (Id)

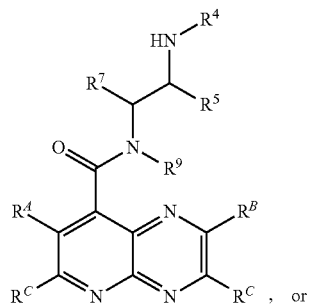

Formula (Ie)

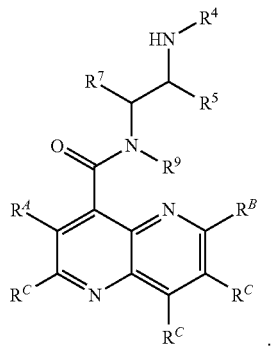

Formula (If)

6. The compound of claim 1, or a pharmaceutically acceptable salt, solvate, diastereomeric mixture, or individual enantiomers thereof, wherein:
$R^A$ is an unsubstituted or substituted phenyl, wherein if $R^A$ is substituted then $R^A$ is substituted with 1-2 $R^{10}$ and 0-2 $R^{11}$; and
$R^B$ is an unsubstituted or substituted phenyl, wherein if $R^B$ is substituted then $R^B$ is substituted with 1-2 $R^{12}$ and 0-2 $R^{13}$.

7. The compound of claim 1, or a pharmaceutically acceptable salt, solvate, diastereomeric mixture, or individual enantiomers thereof, wherein:
$R^A$ is

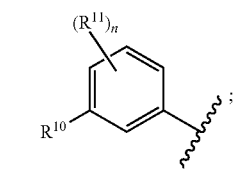

$R^B$ is

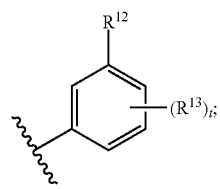

n is 0, 1, or 2; and
t is 0, 1, or 2.

8. The compound of claim 1, or a pharmaceutically acceptable salt, solvate, diastereomeric mixture, or individual enantiomers thereof, wherein:
$R^A$ is

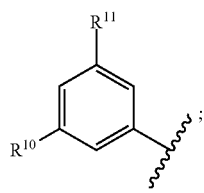

and
$R^B$ is

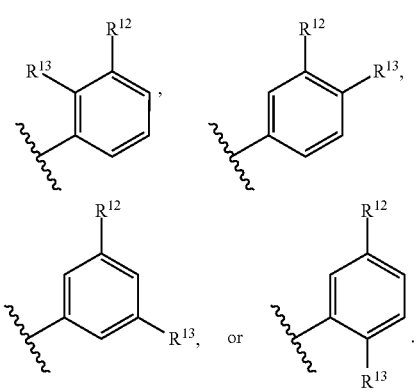

9. The compound of claim 1, or a pharmaceutically acceptable salt, solvate, diastereomeric mixture, or individual enantiomers thereof, wherein:
each $R^{10}$ is independently hydrogen, halogen, unsubstituted or substituted $C_1$-$C_4$alkyl, unsubstituted or substituted $C_1$-$C_4$alkoxy, unsubstituted or substituted $C_1$-$C_4$fluoroalkyl, unsubstituted or substituted $C_1$-$C_4$fluoroalkoxy, unsubstituted or substituted monocyclic carbocycle, unsubstituted or substituted monocyclic heterocycle, —CN, —OH, —$CO_2R^{14}$, —$CH_2CO_2R^{14}$, —C(=O)$NR^{14}R^{15}$, —$CH_2C$(=O)$NR^{14}R^{15}$, —$NR^{14}R^{15}$, —$CH_2NR^{14}R^{15}$, —$NR^{14}C$(=O)$R^{15}$, —$CH_2NR^{14}C$(=O)$R^{15}$, —$SR^{14}$, —S(=O)$R^{15}$, —$SO_2R^{15}$, or —$SO_2NR^{14}R^{15}$, wherein if $R^{10}$ is substituted then $R^{10}$ is substituted with 1-4 $R^{16}$;
each $R^{11}$ is independently hydrogen, halogen, unsubstituted or substituted $C_1$-$C_4$alkyl, unsubstituted or substituted $C_1$-$C_4$alkoxy, unsubstituted or substituted $C_1$-$C_4$fluoroalkyl, unsubstituted or substituted $C_1$-$C_4$fluoroalkoxy, —CN, or —OH, wherein if $R^{11}$ is substituted then $R^{11}$ is substituted with 1-4 $R^{16}$;
each $R^{12}$ is independently hydrogen, halogen, unsubstituted or substituted $C_1$-$C_4$alkyl, unsubstituted or substituted $C_1$-$C_4$alkoxy, unsubstituted or substituted $C_1$-$C_4$fluoroalkyl, unsubstituted or substituted $C_1$-$C_4$fluoroalkoxy, unsubstituted or substituted monocyclic carbocycle, unsubstituted or substituted monocyclic heterocycle, —CN, —OH, —$CO_2R^{14}$, —$CH_2CO_2R^{14}$, —C(=O)$NR^{14}R^{15}$, —$CH_2C$(=O)$NR^{14}R^{15}$, —$NR^{14}R^{15}$, —$CH_2NR^{14}R^{15}$, —$NR^{14}C$(=O)$R^{15}$, —$CH_2NR^{14}C$(=O)$R^{15}$, —$SR^{14}$, —S(=O)$R^{15}$, —$SO_2R^{15}$, or —$SO_2NR^{14}R^{15}$, wherein if $R^{12}$ is substituted then $R^{12}$ is substituted with $R^{16}$; and
each $R^{13}$ is independently hydrogen, halogen, unsubstituted or substituted $C_1$-$C_4$alkyl, unsubstituted or substituted $C_1$-$C_4$alkoxy, unsubstituted or substituted $C_1$-$C_4$fluoroalkyl, unsubstituted or substituted $C_1$-$C_4$fluoroalkoxy, unsubstituted or substituted monocyclic carbocycle, unsubstituted or substituted monocyclic heterocycle, —CN, —OH, wherein if $R^{13}$ is substituted then $R^{13}$ is substituted with $R^{16}$.

10. The compound of claim 1, or a pharmaceutically acceptable salt, solvate, diastereomeric mixture, or individual enantiomers thereof, wherein:
each $R^{10}$ is independently hydrogen, halogen, unsubstituted or substituted $C_1$-$C_4$alkyl, unsubstituted or substituted $C_1$-$C_4$alkoxy, $C_1$-$C_4$fluoroalkyl, $C_1$-$C_4$fluoroalkoxy, unsubstituted or substituted phenyl, unsubstituted or substituted monocyclic heterocycle, —CN, —OH, —$CO_2R^{14}$, —$CH_2CO_2R^{14}$, —C(=O)$NR^{14}R^{15}$, —$CH_2C$(=O)$NR^{14}R^{15}$, —$NR^{14}R^{15}$, —$CH_2NR^{14}R^{15}$, —$NR^{14}C$(=O)$R^{15}$, or —$CH_2NR^{14}C$(=O)$R^{15}$, wherein if $R^{10}$ is substituted then $R^{10}$ is substituted with 1-4 $R^{16}$; and
each $R^{11}$ is independently hydrogen, halogen, unsubstituted or substituted $C_1$-$C_4$alkyl, $C_1$-$C_4$fluoroalkyl, $C_1$-$C_4$alkoxy, $C_1$-$C_4$fluoroalkoxy, or —CN, wherein if $R^{11}$ is substituted then $R^{11}$ is substituted with —$OR^{14}$ or —$NR^{14}R^{15}$.

11. The compound of claim 1, or a pharmaceutically acceptable salt, solvate, diastereomeric mixture, or individual enantiomers thereof, wherein:
$R^4$ is hydrogen, or unsubstituted or substituted $C_1$-$C_6$ alkyl, wherein if $R^4$ is substituted then it is substituted with 1-4 $R^{16}$;
$R^5$ is hydrogen, or unsubstituted or substituted $C_1$-$C_6$ alkyl, wherein if $R^5$ is substituted then it is substituted with 1-4 $R^{16}$;
$R^7$ is hydrogen;
or $R^4$ and $R^5$ are taken together with the nitrogen atom to which they are attached to form a monocyclic 4- to 7-membered heterocyclic ring, wherein if the heterocyclic ring is substituted then the heterocyclic ring is substituted with 1-4 $R^{16}$;
or $R^4$ and $R^7$ are taken together with the nitrogen atom to which they are attached to form a monocyclic 4- to 7-membered heterocyclic ring, wherein if the heterocyclic ring is substituted then the heterocyclic ring is substituted with 1-4 $R^{16}$; and
$R^9$ is hydrogen, unsubstituted or substituted $C_1$-$C_6$ alkyl, or unsubstituted or substituted benzyl, wherein if $R^9$ is substituted then $R^9$ is substituted with 1-4 $R^{16}$.

12. The compound of claim 1, or a pharmaceutically acceptable salt, solvate, diastereomeric mixture, or individual enantiomers thereof, wherein:

$R^4$ is hydrogen, methyl, ethyl, n-propyl, i-propyl, n-butyl, i-butyl, sec-butyl, or tert-butyl;

$R^5$ is hydrogen, methyl, ethyl, n-propyl, i-propyl, n-butyl, i-butyl, sec-butyl, or tert-butyl;

$R^7$ is hydrogen;

or $R^4$ and $R^5$ are taken together with the nitrogen atom to which they are attached to form an unsubstituted or substituted monocyclic 4- to 7-membered heterocyclic ring selected from unsubstituted or substituted azetidinyl, unsubstituted or substituted pyrrolidinyl, unsubstituted or substituted pyrrolidinonyl, unsubstituted or substituted piperidinyl, unsubstituted or substituted morpholinyl, unsubstituted or substituted thiomorpholinyl, unsubstituted or substituted piperazinyl, or unsubstituted or substituted azepanyl, wherein if the heterocyclic ring is substituted then the heterocyclic ring is substituted with 1-4 $R^{16}$;

or $R^4$ and $R^7$ are taken together with the nitrogen atom to which they are attached to form an unsubstituted or substituted monocyclic 4- to 7-membered heterocyclic ring selected from unsubstituted or substituted azetidinyl, unsubstituted or substituted pyrrolidinyl, unsubstituted or substituted pyrrolidinonyl, unsubstituted or substituted piperidinyl, unsubstituted or substituted morpholinyl, unsubstituted or substituted thiomorpholinyl, unsubstituted or substituted piperazinyl, or unsubstituted or substituted azepanyl, wherein if the heterocyclic ring is substituted then the heterocyclic ring is substituted with 1-4 $R^{16}$; and $R^9$ is methyl, ethyl, n-propyl, i-propyl, n-butyl, i-butyl, sec-butyl, tert-butyl, or benzyl.

13. The compound of claim 5, or a pharmaceutically acceptable salt, solvate, diastereomeric mixture, or individual enantiomers thereof, wherein:

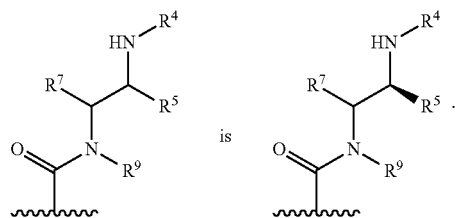

14. The compound of claim 13, or a pharmaceutically acceptable salt, solvate, diastereomeric mixture, or individual enantiomers thereof, wherein:

$R^4$ is hydrogen, methyl, ethyl, n-propyl, i-propyl, n-butyl, i-butyl, sec-butyl, or tert-butyl;

$R^5$ is hydrogen, methyl, ethyl, n-propyl, i-propyl, n-butyl, i-butyl, sec-butyl, or tert-butyl;

$R^7$ is hydrogen; and $R^9$ is methyl, ethyl, n-propyl, i-propyl, n-butyl, i-butyl, sec-butyl, tert-butyl, or benzyl.

15. The compound of claim 5, or a pharmaceutically acceptable salt, solvate, diastereomeric mixture, or individual enantiomers thereof, wherein:

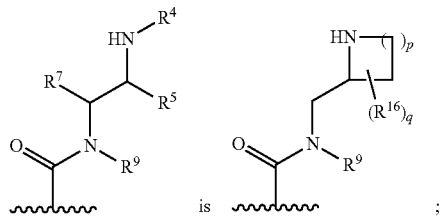

p is 1, 2, or 3;
q is 0, 1, or 2; and
$R^9$ is methyl, ethyl, n-propyl, i-propyl, n-butyl, i-butyl, sec-butyl, tert-butyl, or benzyl.

16. The compound of claim 5, or a pharmaceutically acceptable salt, solvate, diastereomeric mixture, or individual enantiomers thereof, wherein:

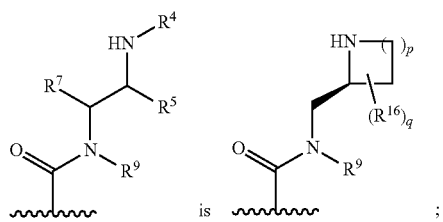

p is 1, 2, or 3;
q is 0, 1, or 2; and
$R^9$ is methyl, ethyl, n-propyl, i-propyl, n-butyl, i-butyl, sec-butyl, tert-butyl, or benzyl.

17. A compound that is:
1-1: 3-(3-chloro-5-methylphenyl)-6-(3-hydroxyphenyl)-N-methyl-N-[(2S)-pyrrolidin-2-ylmethyl]quinoline-4-carboxamide;
1-2: N-[(2S)-2-aminopropyl]-3-(3-chloro-5-methylphenyl)-6-(3-hydroxyphenyl)-N -methylquinoline-4-carboxamide;
1-3: N-[(2S)-2-aminobutyl]-3-(3-chloro-5-methylphenyl)-6-(3-hydroxyphenyl)-N -methylquinoline-4-carboxamide;
1-4: 3-(3-fluoro-5-methylphenyl)-6-(3-hydroxyphenyl)-N-methyl-N-[(2S)-pyrrolidin-2-ylmethyl]quinoline-4-carboxamide;
1-5: 3-(3-chloro-5-methylphenyl)-6-(3-hydroxyphenyl)-N-methyl-N-[(2R)-pyrrolidin-2-ylmethyl]quinoline-4-carboxamide;
1-6: 3-(3-fluoro-5-methoxyphenyl)-6-(3-hydroxyphenyl)-N-methyl-N-[(2S)-pyrrolidin-2-ylmethyl]quinoline-4-carboxamide;
1-7: N-[(2S)-azetidin-2-ylmethyl]-3-(3-fluoro-5-methylphenyl)-6-(3-hydroxyphenyl)-N -methylquinoline-4-carboxamide;
1-8: N-[(2S)-2-aminobutyl]-6-(3-carbamoyl-5-hydroxyphenyl)-3-(3-chloro-5-methylphenyl)-N -methylquinoline-4-carboxamide;
1-9: N-[(2S)-2-aminobutyl]-6-(3-cyano-5-methoxyphenyl)-3-(3-fluoro-5-methylphenyl)-N -methylquinoline-4-carboxamide;

1-10: N-[(2S)-2-aminobutyl]-6-(3-cyano-5-hydroxyphenyl)-3-(3-fluoro-5-methylphenyl)-N-methylquinoline-4-carboxamide;

1-11: N-[(2S)-2-aminobutyl]-3-(3-fluoro-5-methylphenyl)-6-(5-hydroxy-2-methylphenyl)-N-methylquinoline-4-carboxamide;

1-12: N-[(2S)-2-aminobutyl]-6-(3-cyano-2-methylphenyl)-3-(3-fluoro-5-methylphenyl)-N-methylquinoline-4-carboxamide;

1-13: N-[(2S)-2-aminobutyl]-6-(3-fluoro-2-methylphenyl)-3-(3-fluoro-5-methylphenyl)-N-methylquinoline-4-carboxamide;

1-14: N-[(2S)-2-aminobutyl]-6-(5-cyano-2-methylphenyl)-3-(3-fluoro-5-methylphenyl)-N-methylquinoline-4-carboxamide;

1-15: N-[(2S)-2-aminobutyl]-6-(3-cyano-5-fluorophenyl)-3-(3-fluoro-5-methylphenyl)-N-methylquinoline-4-carboxamide;

1-16: 6-(3-cyanophenyl)-3-(3-fluoro-5-methylphenyl)-N-methyl-N-[(2S)-pyrrolidin-2-ylmethyl]quinoline-4-carboxamide;

1-17: N-[(2S)-2-aminobutyl]-6-(3-fluoro-5-methoxyphenyl)-3-(3-fluoro-5-methylphenyl)-N-methylquinoline-4-carboxamide;

1-18: 3-(3-fluorophenyl)-6-(3-hydroxyphenyl)-N-methyl-N-[(2S)-pyrrolidin-2-ylmethyl]quinoline-4-carboxamide;

1-19: N-[(2S)-2-aminopropyl]-6-(3-cyano-5-methoxyphenyl)-3-(3-fluoro-5-methylphenyl)-N-methylquinoline-4-carboxamide;

1-20: N-[(2S)-2-aminopropyl]-6-(3-cyano-5-fluorophenyl)-3-(3-fluoro-5-methylphenyl)-N-methylquinoline-4-carboxamide;

1-21: 6-(3-cyano-5-methoxyphenyl)-3-(3-fluoro-5-methylphenyl)-N-methyl-N-[(2S)-pyrrolidin-2-ylmethyl]quinoline-4-carboxamide;

1-22: 6-(3-cyano-5-fluorophenyl)-3-(3,5-difluorophenyl)-N-methyl-N-[(2S)-pyrrolidin-2-ylmethyl]quinoline-4-carboxamide;

1-23: 3-(3,5-difluorophenyl)-6-(2-fluoro-3-hydroxyphenyl)-N-methyl-N-[(2S)-pyrrolidin-2-ylmethyl]quinoline-4-carboxamide;

1-24: 6-(3-cyano-5-fluorophenyl)-3-(3-fluoro-5-methylphenyl)-N-methyl-N-[(2S)-pyrrolidin-2-ylmethyl]quinoline-4-carboxamide;

1-25: 6-(3-cyano-2-fluorophenyl)-3-(3,5-difluorophenyl)-N-methyl-N-[(2S)-pyrrolidin-2-ylmethyl]quinoline-4-carboxamide;

1-26: 6-(3-carbamoyl-5-fluorophenyl)-3-(3,5-difluorophenyl)-N-methyl-N-[(2S)-pyrrolidin-2-ylmethyl]quinoline-4-carboxamide;

1-27: 6-(5-cyano-2-methoxyphenyl)-3-(3,5-difluorophenyl)-N-methyl-N-[(2S)-pyrrolidin-2-ylmethyl]quinoline-4-carboxamide;

1-28: 6-(5-cyano-2-fluorophenyl)-3-(3,5-difluorophenyl)-N-methyl-N-[(2S)-pyrrolidin-2-ylmethyl]quinoline-4-carboxamide;

1-29: 3-(3-fluoro-5-methylphenyl)-6-(3-hydroxyphenyl)-N-methyl-N-(morpholin-3-ylmethyl)quinoline-4-carboxamide;

1-30: 6-(3-cyano-5-methoxyphenyl)-3-(3,5-difluorophenyl)-N-methyl-N-[(2S)-pyrrolidin-2-ylmethyl]quinoline-4-carboxamide;

1-31: 6-(2-chloro-3-hydroxyphenyl)-3-(3,5-difluorophenyl)-N-methyl-N-[(2S)-pyrrolidin-2-ylmethyl]quinoline-4-carboxamide;

1-32: N-[(2S)-2-aminobutyl]-6-(3-cyano-5-methoxyphenyl)-3-(3,5-difluorophenyl)-N-methylquinoline-4-carboxamide;

1-33: 6-(3-carbamoyl-5-fluorophenyl)-3-(3-fluoro-5-methylphenyl)-N-methyl-N-[(2S)-pyrrolidin-2-ylmethyl]quinoline-4-carboxamide;

1-34: 6-(3-cyano-5-fluorophenyl)-3-(3-fluoro-5-hydroxyphenyl)-N-methyl-N-[(2S)-pyrrolidin-2-ylmethyl]quinoline-4-carboxamide;

1-35: 6-(3-cyano-5-fluorophenyl)-3-[3-fluoro-5-(2-hydroxyethyl)phenyl]-N-methyl-N-[(2S)-pyrrolidin-2-ylmethyl]quinoline-4-carboxamide;

1-36: 3-fluoro-5-[3-(3-fluoro-5-methylphenyl)-4-{methyl[(2S)-pyrrolidin-2-ylmethyl]carbamoyl}quinolin-6-yl]benzoic acid;

1-37: 4-{3-[6-(3-cyano-5-fluorophenyl)-4-{methyl[(2S)-pyrrolidin-2-ylmethyl]carbamoyl}quinolin-3-yl]-5-fluorophenoxy}butanoic acid;

1-38: N-[(2S)-2-aminobutyl]-6-(3-cyano-5-hydroxyphenyl)-3-(3,5-difluorophenyl)-N-methylquinoline-4-carboxamide;

1-39: 6-(3-cyano-5-fluorophenyl)-3-[3-fluoro-5-(2-hydroxyethoxy)phenyl]-N-methyl-N-[(2S)-pyrrolidin-2-ylmethyl]quinoline-4-carboxamide;

1-40: 6-[3-cyano-5-(trifluoromethyl)phenyl]-3-(3-fluoro-5-methylphenyl)-N-methyl-N-[(2S)-pyrrolidin-2-ylmethyl]quinoline-4-carboxamide;

1-41: 6-(2-chloro-3-hydroxyphenyl)-3-(3-fluoro-5-methylphenyl)-N-methyl-N-[(2S)-pyrrolidin-2-ylmethyl]quinoline-4-carboxamide;

1-42: 6-(3-cyano-5-fluorophenyl)-3-[3-fluoro-5-(2-methoxyethoxy)phenyl]-N-methyl-N-[(2S)-pyrrolidin-2-ylmethyl]quinoline-4-carboxamide;

1-43: 3-(3-fluoro-5-methylphenyl)-6-[3-hydroxy-2-(methoxymethyl)phenyl]-N-methyl-N-[(2S)-pyrrolidin-2-ylmethyl]quinoline-4-carboxamide 1-44: 3-[3-(3-fluoro-5-methylphenyl)-4-{methyl[(2S)-pyrrolidin-2-ylmethyl]carbamoyl}quinolin-6-yl]benzoic acid;

1-45: 6-(3-cyano-2-methylphenyl)-3-[3-fluoro-5-(2-hydroxyethyl)phenyl]-N-methyl-N-[(2S)-pyrrolidin-2-ylmethyl]quinoline-4-carboxamide;

1-46: 4-[3-(3-fluoro-5-methylphenyl)-4-{methyl[(2S)-pyrrolidin-2-ylmethyl]carbamoyl}quinolin-6-yl]benzoic acid;

1-47: 2-[3-(3-fluoro-5-methylphenyl)-4-{methyl[(2S)-pyrrolidin-2-ylmethyl]carbamoyl}quinolin-6-yl]benzoic acid;

1-48: 2-{3-[3-(3-fluoro-5-methylphenyl)-4-{methyl[(2S)-pyrrolidin-2-ylmethyl]carbamoyl}quinolin-6-yl]phenyl}acetic acid;

1-49: methyl 2-{3-[3-(3-fluoro-5-methylphenyl)-4-{methyl[(2S)-pyrrolidin-2-ylmethyl]carbamoyl}quinolin-6-yl]phenyl}acetate;

1-50: 3-{3-[3-(3-fluoro-5-methylphenyl)-4-{methyl[(2S)-pyrrolidin-2-ylmethyl]carbamoyl}quinolin-6-yl]phenyl}propanoic acid;

1-51: 6-(3-cyano-2-methylphenyl)-3-(3,5-difluorophenyl)-N-methyl-N-[(2S)-pyrrolidin-2-ylmethyl]quinoline-4-carboxamide;

1-52: 6-(5-cyano-2-methylphenyl)-3-(3,5-difluorophenyl)-N-methyl-N-[(2S)-pyrrolidin-2-ylmethyl]quinoline-4-carboxamide;

1-53: 6-(3-carbamoyl-2-fluorophenyl)-3-(3-fluoro-5-methylphenyl)-N-methyl-N-[(2S)-pyrrolidin-2-ylmethyl]quinoline-4-carboxamide;

1-54: 6-(3-carbamoyl-4-fluorophenyl)-3-(3-fluoro-5-methylphenyl)-N-methyl-N-[(2S) -pyrrolidin-2-ylmethyl]quinoline-4-carboxamide;

1-55: N-[(2S)-2-aminobutyl]-6-(3-cyano-5-fluorophenyl)-3-(3,5-difluorophenyl)-N -methylquinoline-4-carboxamide;

1-56: 6-(3-cyano-5-fluorophenyl)-3-(2,5-difluorophenyl)-N-methyl-N-[(2S)-pyrrolidin-2-ylmethyl]quinoline-4-carboxamide;

1-57: 3-(2-chloro-5-methylphenyl)-6-(3-cyano-5-fluorophenyl)-N-methyl-N-[(2S)-pyrrolidin-2-ylmethyl]quinoline-4-carboxamide;

1-58: 6-(3-cyano-5-fluorophenyl)-3-(5-fluoro-2-methylphenyl)-N-methyl-N-[(2S)-pyrrolidin-2-ylmethyl]quinoline-4-carboxamide;

1-59: 2-{3-fluoro-5-[3-(3-fluoro-5-methylphenyl)-4-{methyl[(2S)-pyrrolidin-2-ylmethyl]carbamoyl}quinolin-6-yl]phenyl}acetic acid;

1-60: 3-(3-fluoro-5-methylphenyl)-N-methyl-N-[(2S)-pyrrolidin-2-ylmethyl]-6-(3-sulfamoylphenyl)quinoline-4-carboxamide;

1-61: 6-(3,5-difluorophenyl)-3-(3-fluoro-5-methylphenyl)-N-methyl-N-[(3S)-pyrrolidin-3-yl]quinoline-4-carboxamide;

1-62: 6-(3,5-difluorophenyl)-3-(3-fluoro-5-methylphenyl)-N-methyl-N-[(2S)-pyrrolidin-2-ylmethyl]quinoline-4-carboxamide;

1-63: 6-(6-carbamoylpyrazin-2-yl)-3-(3-fluoro-5-methylphenyl)-N-methyl-N-[(2S)-pyrrolidin-2-ylmethyl]quinoline-4-carboxamide;

1-64: 6-(2-chloro-5-methoxyphenyl)-3-(3-fluoro-5-methylphenyl)-N-methyl-N-[(2S)-pyrrolidin -2-ylmethyl]quinoline-4-carboxamide;

1-65: 2-{3-chloro-5-[6-(3-cyano-5-fluorophenyl)-4-{methyl[(2S)-pyrrolidin-2-ylmethyl]carbamoyl}quinolin-3-yl]phenoxy}acetic acid;

1-66: 3-(3-fluoro-5-methylphenyl)-6-(3-fluoro-5-sulfamoylphenyl)-N-methyl-N-[(2S) -pyrrolidin-2-ylmethyl]quinoline-4-carboxamide;

1-67: 6-(3-cyano-5-fluorophenyl)-3-(2,3-difluorophenyl)-N-methyl-N- [(2 S)-pyrrolidin-2-ylmethyl]quinoline-4-carboxamide;

1-68: N-[(2S)-2-amino-3-methylbutyl]-6-(3,5-difluorophenyl)-3-(3-fluoro-5-methylphenyl)-N -methylquinoline-4-carboxamide;

1-69: 6-(3-cyano-5-fluorophenyl)-3-[3-fluoro-5-(2-hydroxypropan-2-yl)phenyl]-N-methyl-N -[(2S)-pyrrolidin-2-ylmethyl]quinoline-4-carboxamide;

1-70: N-[(2S)-2-aminobutyl]-6-[3-fluoro-5-(trifluoromethyl)phenyl]-3-(3-fluoro-5-methylphenyl)-N-methylquinoline-4-carboxamide;

1-71: 6-(3-cyano-5-fluorophenyl)-3-[3-fluoro-5-(prop-1-en-2-yl)phenyl]-N-methyl-N-[(2S) -pyrrolidin-2-ylmethyl]quinoline-4-carboxamide;

1-72: 6-(3-carbamoyl-4-hydroxyphenyl)-3-(3-fluoro-5-methylphenyl)-N-methyl-N-[(2S) -pyrrolidin-2-ylmethyl]quinoline-4-carboxamide;

1-73: 3-[3-(dimethylcarbamoyl)phenyl]-6-(3-hydroxyphenyl)-N-methyl-N-[(2S)-pyrrolidin-2-ylmethyl]quinoline-4-carboxamide;

1-74: 6- [3-(carbamoylmethyl)-5-fluorophenyl]-3-(3-fluoro-5-methylphenyl)-N-methyl-N -[(2S)-pyrrolidin-2-ylmethyl]quinoline-4-carboxamide;

1-75: N- [(2 S)-2-aminopropyl]-6-(3-carbamoyl-5-methoxyphenyl)-3-(3-fluoro-5-methylphenyl) -N-methylquinoline-4-carboxamide;

1-76: 3-(4-{[(2S)-2-aminopropyl](methyl)carbamoyl}-3-(3-fluoro-5-methylphenyl)quinolin-6-yl)-5-methoxybenzoic acid;

1-76: 6-[3-cyano-5-(methylcarbamoyl)phenyl]-3-(3-fluoro-5-methylphenyl)-N-methyl-N-[(2S) -pyrrolidin-2-ylmethyl]quinoline-4-carboxamide;

1-77: 6-(3-cyano-2-hydroxyphenyl)-3-(3-fluoro-5-methylphenyl)-N-methyl-N-[(2S)-pyrrolidin -2-ylmethyl]quinoline-4-carboxamide;

1-78: 6-(3-carbamoyl-5-cyanophenyl)-3-(3,5-difluorophenyl)-N-methyl-N-[(2S)-pyrrolidin-2-ylmethyl]quinoline-4-carboxamide;

1-79: 6-(3-cyano-5-fluorophenyl)-3-(3-fluoro-5-methylphenyl)-N-{[(2S,4R)-4-fluoropyrrolidin -2-yl]methyl}-N-methylquinoline-4-carboxamide;

1-80: N-[(2S)-azetidin-2-ylmethyl]-3-(3-chloro-5-methylphenyl)-6-(3-cyano-5-fluorophenyl)-N -methylquinoline-4-carboxamide;

1-81: N-[(2S)-azetidin-2-ylmethyl]-6-(3-carbamoyl-5-fluorophenyl)-3-(3-chloro-5-methylphenyl)-N-methylquinoline-4-carboxamide;

1-82: N-[(2S)-azetidin-2-ylmethyl]-6-(3-cyano-5-fluorophenyl)-3-(3,5-dichlorophenyl)-N -methylquinoline-4-carboxamide;

1-83: N-[(2S)-azetidin-2-ylmethyl]-6-(3-carbamoyl-5-fluorophenyl)-3-(3,5-dichlorophenyl)-N -methylquinoline-4-carboxamide;

1-84: N-[(2S)-azetidin-2-ylmethyl]-3-(3-chloro-5-methylphenyl)-6-(3-cyano-2-hydroxyphenyl) -N-methylquinoline-4-carboxamide;

1-85: N-[(2S)-azetidin-2-ylmethyl]-6-(3-cyano-2-hydroxyphenyl)-3-(3,5-dichlorophenyl)-N -ethylquinoline-4-carboxamide;

1-86: N-[(2S)-azetidin-2-ylmethyl]-3-(3-chloro-5-fluorophenyl)-6-(3-cyano-2-hydroxyphenyl) -N-methylquinoline-4-carboxamide;

1-87: 3-(3-chloro-5-fluorophenyl)-6-(3-cyano-2-hydroxyphenyl)-N-methyl-N-[(2S)-pyrrolidin -2-ylmethyl]quinoline-4-carboxamide;

1-88: 6-(3-carbamoyl-5-methylphenyl)-3-(3-chloro-5-fluorophenyl)-N-methyl-N-[(2S) -pyrrolidin-2-ylmethyl]quinoline-4-carboxamide;

1-89: N-[(2S)-2-amino-4-fluorobutyl]-6-(3,5-difluorophenyl)-3-(3-fluoro-5-methylphenyl)-N -methylquinoline-4-carboxamide;

1-90: 6-(3-cyano-5-fluorophenyl)-3-(3-fluoro-5-methylphenyl)-N- {[(2S,4S)-4-fluoropyrrolidin -2-yl]methyl}-N-methylquinoline-4-carboxamide;

1-91: 6-(3-fluoro-2-hydroxyphenyl)-3-(3-fluoro-5-methylphenyl)-N-methyl-N-[(2S)-pyrrolidin -2-ylmethyl]quinoline-4-carboxamide;

2-1: 3-(3-chloro-5-methylphenyl)-6-(3-hydroxyphenyl)-N-methyl-N-[(2S)-pyrrolidin-2-ylmethyl]-1,5-naphthyridine-4-carboxamide;

2-2: 3,6-bis(3-hydroxyphenyl)-N-methyl-N-[(2S)-pyrrolidin-2-ylmethyl]-1,5-naphthyridine-4-carboxamide;

2-3: 3-(3-chloro-5-methylphenyl)-6-(2-fluoro-5-hydroxyphenyl)-N-methyl-N-[(2S)-pyrrolidin -2-ylmethyl]-1,5-naphthyridine-4-carboxamide;

2-4: 3-(3-chloro-5-methylphenyl)-6-(3-cyano-5-hydroxyphenyl)-N-methyl-N-[(2S)-pyrrolidin -2-ylmethyl]-1,5-naphthyridine-4-carboxamide;

2-5: N-[(2S)-2-aminobutyl]-6-(3-cyano-5-hydroxyphenyl)-3-(3,5-dimethylphenyl)-N-methyl -1,5-naphthyridine-4-carboxamide;

2-6: N-[(2S)-2-aminobutyl]-3-(3-chloro-5-methylphenyl)-6-(3-cyano-5-hydroxyphenyl)-N-methyl-1,5-naphthyridine-4-carboxamide;

2-7: N-[(2S)-2-aminobutyl]-6-(3-cyano-5-hydroxyphenyl)-3-(3-fluoro-5-methylphenyl)-N-methyl-1,5-naphthyridine-4-carboxamide;

2-8: 6-(3-hydroxyphenyl)-N-methyl-3-[3-(1H-pyrazol-1-yl)phenyl]-N-[(2S)-pyrrolidin-2-ylmethyl]-1,5-naphthyridine-4-carboxamide;

2-9: 3-(3,5-difluorophenyl)-6-(3-hydroxyphenyl)-N-methyl-N-[(2S)-pyrrolidin-2-ylmethyl]-1,5-naphthyridine-4-carboxamide;

2-10: 6-(3-cyano-5-fluorophenyl)-3-[3-(2-hydroxyethyl)phenyl]-N-methyl-N-[(2S)-pyrrolidin-2-ylmethyl]-1,5-naphthyridine-4-carboxamide;

2-11: 6-(3-cyano-5-fluorophenyl)-N-methyl-3-phenyl-N-[(2S)-pyrrolidin-2-ylmethyl]-1,5-naphthyridine-4-carboxamide;

2-12: 6-(3-cyano-5-fluorophenyl)-3-(3-methoxyphenyl)-N-methyl-N-[(2S)-pyrrolidin-2-ylmethyl]-1,5-naphthyridine-4-carboxamide;

2-13: 6-(3-cyano-5-fluorophenyl)-3-(3-fluorophenyl)-N-methyl-N-[(2S)-pyrrolidin-2-ylmethyl]-1,5-naphthyridine-4-carboxamide;

2-14: 6-(3-cyano-5-fluorophenyl)-3-[3-(acetamidomethyl)phenyl]-N-methyl-N-[(2S)-pyrrolidin-2-ylmethyl]-1,5-naphthyridine-4-carboxamide;

2-15: 6-(3-cyano-5-fluorophenyl)-3-(3-cyanophenyl)-N-methyl-N-[(2S)-pyrrolidin-2-ylmethyl]-1,5-naphthyridine-4-carboxamide;

2-16: 6-(3-cyano-5-fluorophenyl)-3-(3,5-difluorophenyl)-N-methyl-N-[(2S)-pyrrolidin-2-ylmethyl]-1,5-naphthyridine-4-carboxamide;

2-17: 6-(3-cyano-5-fluorophenyl)-3-(3-fluoro-5-methylphenyl)-N-methyl-N-[(2S)-pyrrolidin-2-ylmethyl]-1,5-naphthyridine-4-carboxamide;

2-18: 6-(3-cyano-5-fluorophenyl)-3-(3-fluoro-5-methoxyphenyl)-N-methyl-N-[(2S)-pyrrolidin-2-ylmethyl]-1,5-naphthyridine-4-carboxamide;

2-19: 6-(3-cyanophenyl)-3-(3,5-difluorophenyl)-N-methyl-N-[(2S)-pyrrolidin-2-ylmethyl]-1,5-naphthyridine-4-carboxamide;

2-20: 2-{3-[6-(3-hydroxyphenyl)-4-[methyl(pyrrolidin-2-ylmethyl)carbamoyl]-1,5-naphthyridin-3-yl]phenyl}acetic acid;

2-21: methyl 2-{3-[6-(3-hydroxyphenyl)-4-{methyl[(2S)-pyrrolidin-2-ylmethyl]carbamoyl}-1,5-naphthyridin-3-yl]phenyl}acetate;

2-22: 3-{3-[6-(3-hydroxyphenyl)-4-{methyl[(2S)-pyrrolidin-2-ylmethyl]carbamoyl}-1,5-naphthyridin-3-yl]phenyl}propanoic acid;

2-23: methyl 3-{3-[6-(3-hydroxyphenyl)-4-{methyl[(2S)-pyrrolidin-2-ylmethyl]carbamoyl}-1,5-naphthyridin-3-yl]phenyl}propanoate;

2-24: 6-(3-carbamoyl-5-fluorophenyl)-3-(3-fluoro-5-methylphenyl)-N-methyl-N-[(2S)-pyrrolidin-2-ylmethyl]-1,5-naphthyridine-4-carboxamide;

3-1: 6-(3-hydroxyphenyl)-N-methyl-N-[(2S)-pyrrolidin-2-ylmethyl]-1,5-naphthyridine-4-carboxamide;

3-2: 3-(3-fluoro-5-methylphenyl)-N-methyl-6-(pyrrolidin-1-yl)-N-[(2S)-pyrrolidin-2-ylmethyl]-1,5-naphthyridine-4-carboxamide;

3-3: 3-(3-fluoro-5-methylphenyl)-6-(3-hydroxypiperidin-1-yl)-N-methyl-N-[(2S)-pyrrolidin-2-ylmethyl]-1,5-naphthyridine-4-carboxamide;

3-4: 6-(3-hydroxyphenyl)-N-methyl-3-(pyrrolidin-1-yl)-N-[(2S)-pyrrolidin-2-ylmethyl]-1,5-naphthyridine-4-carboxamide;

3-5: 6-(3-hydroxyphenyl)-N-methyl-3-(6-methylpyridin-2-yl)-N-[(2S)-pyrrolidin-2-ylmethyl]-1,5-naphthyridine-4-carboxamide;

3-6: 3-(2,6-dimethylmorpholin-4-yl)-6-(3-hydroxyphenyl)-N-methyl-N-[(2S)-pyrrolidin-2-ylmethyl]-1,5-naphthyridine-4-carboxamide;

3-7: 6-(3-cyano-5-fluorophenyl)-N-methyl-3-(prop-1-yn-1-yl)-N-[(2S)-pyrrolidin-2-ylmethyl]-1,5-naphthyridine-4-carboxamide;

3-8: 6-(5-cyanopyridin-3-yl)-3-(3-fluoro-5-methylphenyl)-N-methyl-N-[(2S)-pyrrolidin-2-ylmethyl]quinoline-4-carboxamide;

3-9: 6-(3-cyano-5-fluorophenyl)-3-(cyclopent-1-en-1-yl)-N-methyl-N-[(2S)-pyrrolidin-2-ylmethyl]-1,5-naphthyridine-4-carboxamide;

3-10: 3-(3-fluoro-5-methylphenyl)-N-methyl-6-(1-methyl-1H-pyrazol-4-yl)-N-[(2S)-pyrrolidin-2-ylmethyl]quinoline-4-carboxamide;

3-11: 6-(3-hydroxyphenyl)-N-methyl-3-(piperidin-1-yl)-N-[(2S)-pyrroldin-2-ylmethyl]-1,5-naphthyridine-4-carboxamide;

3-12: 6-(3-hydroxyphenyl)-N-methyl-3-(morpholin-4-yl)-N-[(2S)-pyrrolidin-2-ylmethyl]-1,5-naphthyridine-4-carboxamide;

3-13: 6-(6-cyanopyridin-2-yl)-3-(3-fluoro-5-methylphenyl)-N-methyl-N-[(2S)-pyrrolidin-2-ylmethyl]quinoline-4-carboxamide;

3-14: 6-(4-cyanopyridin-2-yl)-3-(3-fluoro-5-methylphenyl)-N-methyl-N-[(2S)-pyrrolidin-2-ylmethyl]quinoline-4-carboxamide;

3-15: 6-(2-amino-5-cyanopyridin-3-yl)-3-(3-fluoro-5-methylphenyl)-N-methyl-N-[(2S)-pyrrolidin-2-ylmethyl]quinoline-4-carboxamide;

3-16: 6-(2-cyanopyridin-4-yl)-3-(3-fluoro-5-methylphenyl)-N-methyl-N-[(2S)-pyrrolidin-2-ylmethyl]quinoline-4-carboxamide;

3-17: 3-[3-(hydroxymethyl)pyrrolidin-1-yl]-6-(3-hydroxyphenyl)-N-methyl-N-[(2S)-pyrrolidin-2-ylmethyl]-1,5-naphthyridine-4-carboxamide;

3-18: 6-(3-hydroxyphenyl)-N-methyl-3-(prop-1-yn-1-yl)-N-((2S)-pyrrolidin-2-ylmethyl)-1,5-naphthyridine-4-carboxamide;

3-19: 6-(4-cyanopyrimidin-2-yl-3-(3-fluoro-5-methylphenyl)-N-methyl-N-[(2S)-pyrrolidin-2-ylmethyl]quinoline-4-carboxamide;

3-20: 3-(cis-2,6-dimethylmorpholin-4-yl)-6-(3-hydroxyphenyl)-N-methyl-N-[(2S)-pyrrolidin-2-ylmethyl]quinoline-4-carboxamide;

3-21: 3-(trans-2,6-dimethylmorpholin-4-yl-6-(3-hydroxyphenyl)-N-methyl-N-[(2S)-pyrrolidin-2-ylmethyl]quinoline-4-carboxamide;

3-22: 6-(5-cyano-2,4-dimethylpyridin-3-yl)-3-(3-fluoro-5-methylphenyl)-N-methyl-N-[(2S)-pyrrolidin-2-ylmethyl]quinoline-4-carboxamide;

3-33: 6-(2-carbamoylpyridin-4-yl)-3-(3-fluoro-5-methylphenyl)-N-methyl-N-[(2S)-pyrrolidin-2-ylmethyl]quinoline-4-carboxamide;

3-34: 6-(3-cyano-5-fluorophenyl)-3-(2-fluoro-3,5-dimethylphenyl)-N-methyl-N-[(2S)-pyrrolidin-2-ylmethyl]quinoline-4-carboxamide;

3-35: 6-(3-cyano-5-fluorophenyl)-3-(2,6-dimethylmorpholin-4-yl)-N-methyl-N-[(2S)-pyrrolidin-2-ylmethyl]-1,5-naphthyridine-4-carboxamide;

3-36: 6-(3-cyano-5-fluorophenyl)-3-(2,6-dimethylmorpholin-4-yl)-N-methyl-N-[(2S)-pyrrolidin-2-ylmethyl]-1,5-naphthyridine-4-carboxamide;

3-37: 6-[5-cyano-2-(methylamino)pyridin-3-yl]-3-(3-fluoro-5-methylphenyl)-N-methyl-N-[(2S)-pyrrolidin-2-ylmethyl]quinoline-4-carboxamide;

3-38: 6-[5-cyano-2-(dimethylamino)pyridin-3-yl]-3-(3-fluoro-5-methylphenyl)-N-methyl-N-[(2S)-pyrrolidin-2-ylmethyl]quinoline-4-carboxamide;

3-39: 6-(5-cyano-2-methylpyridin-3-yl)-3-(3-fluoro-5-methylphenyl)-N-methyl-N-[(2S)-pyrrolidin-2-ylmethyl]quinoline-4-carboxamide;

3-40: 6-(5-cyanopyridin-3-yl)-3-[3-fluoro-5-(2-hydroxyethyl)phenyl]-N-methyl-N-[(2S)-pyrrolidin-2-ylmethyl]quinoline-4-carboxamide;

3-41: N-[(2S)-2-aminobutyl]-6-[5-cyano-2-(dimethylamino)pyridin-3-yl]-3-(3-fluoro-5-methylphenyl)-N-methylquinoline-4-carboxamide;

3-42: 6-(3-cyano-5-fluorophenyl)-N-methyl-3-[(2R)-2-phenylmorpholin-4-yl]-N-[(2S)-pyrrolidin-2-ylmethyl]-1,5-naphthyridine-4-carboxamide;

3-43: 6-(3-cyano-5-fluorophenyl)-N-methyl-3-(3-methylbutyl)-N-[(2S)-pyrrolidin-2-ylmethyl]-1,5-naphthyridine-4-carboxamide;

3-44: 6-(6-carbamoylpyrazin-2-yl)-3-(3-fluoro-5-methylphenyl)-N-methyl-N-[(2S)-pyrrolidin-2-ylmethyl]quinoline-4-carboxamide;

3-45: 6-(3-cyano-5-fluorophenyl)-3-(2,6-dimethylmorpholin-4-yl)-N-methyl-N-[(2S)-pyrrolidin-2-ylmethyl]quinoline-4-carboxamide;

3-46: 3-(3-fluoro-5-methylphenyl)-N-methyl-6-[6-(methylcarbamoyl)pyridin-2-yl]-N-[(2S)-pyrrolidin-2-ylmethyl]quinoline-4-carboxamide;

3-47: 6-(3-cyano-5-fluorophenyl)-N-methyl-3-[(2S)-2-phenylmorpholin-4-yl]-N-[(2S)-pyrrolidin-2-ylmethyl]-1,5-naphthyridine-4-carboxamide;

3-48: 3-(3-fluoro-5-methylphenyl)-N-methyl-6-(pyridin-3-yl)-N-[(2S)-pyrrolidin-2-ylmethyl]quinoline-4-carboxamide;

3-49: 6-(3-cyano-5-fluorophenyl)-N-methyl-N-[(2S)-pyrrolidin-2-ylmethyl]-3-(2,2,6,6-tetramethylmorpholin-4-yl)-1,5-naphthyridine-4-carboxamide;

3-50: 6-(3-carbamoyl-4,5-difluorophenyl)-3-(3-fluoro-5-methylphenyl)-N-methyl-N-[(2S)-pyrrolidin-2-ylmethyl]quinoline-4-carboxamide;

3-51: 6-(6-aminopyridin-2-yl)-3-(3-fluoro-5-methylphenyl)-N-methyl-N-[(2S)-pyrrolidin-2-ylmethyl]quinoline-4-carboxamide;

3-52: 6-(3-carbamoyl-2,5-difluorophenyl)-3-(3-fluoro-5-methylphenyl)-N-methyl-N-[(2S)-pyrrolidin-2-ylmethyl]quinoline-4-carboxamide;

3-53: 3-(3-fluoro-5-methylphenyl)-6-(6-methoxypyridin-2-yl)-N-methyl-N-[(2S)-pyrrolidin-2-ylmethyl]quinoline-4-carboxamide;

3-54: 6-(3-cyano-5-fluorophenyl)-N-methyl-N-[(2S)-pyrrolidin-2-ylmethyl]-3-[5-(trifluoromethyl)-2,3-dihydro-1H-indol-1-yl]-1,5-naphthyridine-4-carboxamide;

3-55: 6-(3-cyano-5-fluorophenyl)-N-methyl-N-[(2S)-pyrrolidin-2-ylmethyl]-3-[5-(trifluoromethyl)-2,3-dihydro-1H-isoindol-2-yl]-1,5-naphthyridine-4-carboxamide;

3-56: 6-(5-cyano-2-hydroxypyridin-3-yl)-3-(3-fluoro-5-methylphenyl)-N-methyl-N-[(2S)-pyrrolidin-2-ylmethyl]quinoline-4-carboxamide;

3-57: 6-(6-carbamoyl-3-methylpyridin-2-yl)-3-(3-fluoro-5-methylphenyl)-N-methyl-N-[(2S)-pyrrolidin-2-ylmethyl]quinoline-4-carboxamide;

3-58: 6-(5-carbamoylpyridin-3-yl)-3-[3-fluoro-5-(2-hydroxyethyl)phenyl]-N-methyl-N-[(2S)-pyrrolidin-2-ylmethyl]quinoline-4-carboxamide;

3-59: 3-(3-fluoro-5-methylphenyl)-6-(5-fluoropyridin-3-yl)-N-methyl-N-[(2S)-pyrrolidin-2-ylmethyl]quinoline-4-carboxamide;

3-60: 3-(3-fluoro-5-methylphenyl)-6-(1H-indol-6-yl)-N-methyl-N-[(2S)-pyrrolidin-2-ylmethyl]quinoline-4-carboxamide;

3-61: 3-(3-fluoro-5-methylphenyl)-6-(1H-indol-4-yl)-N-methyl-N-[(2S)-pyrrolidin-2-ylmethyl]quinoline-4-carboxamide;

3-62: 6-(2-amino-5-fluoropyridin-3-yl)-3-(3-fluoro-5-methylphenyl)-N-methyl-N-[(2S)-pyrrolidin-2-ylmethyl]quinoline-4-carboxamide;

3-64: 6-(3-carbamoyl-5-fluorophenyl)-3-[(cis)-2,6-dimethylmorpholin-4-yl]-N-methyl-N-[(2S)-pyrrolidin-2-ylmethyl]quinoline-4-carboxamide;

3-65: 3-(3-fluoro-5-methylphenyl)-N-methyl-6-(4-methylpyridin-3-yl)-N-[(2S)-pyrrolidin-2-ylmethyl]quinoline-4-carboxamide;

3-66: 3-(3-fluoro-5-methylphenyl)-N-methyl-6-(1-oxo-2,3-dihydro-1H-isoindol-4-yl)-N-[(2S)-pyrrolidin-2-ylmethyl]quinoline-4-carboxamide;

3-67: N-[(2S)-2-aminobutyl]-6-(6-carbamoylpyridin-2-yl)-3-(3-fluoro-5-methylphenyl)-N-methylquinoline-4-carboxamide;

3-68: 6-(5-chloropyridin-3-yl)-3-(3-fluoro-5-methylphenyl)-N-methyl-N-[(2S)-pyrrolidin-2-ylmethyl]quinoline-4-carboxamide;

3-69: 3-{3-azabicyclo[3.1.0]hexan-3-yl}-6-(3-cyano-5-fluorophenyl)-N-methyl-N-[(2S)-pyrrolidin-2-ylmethyl]-1,5-naphthyridine-4-carboxamide;

3-70: 6-(3-cyano-5-fluorophenyl)-N-methyl-3-{8-oxa-3-azabicyclo[3.2.1]octan-3-yl}-N-[(2S)-pyrrolidin-2-ylmethyl]-1,5-naphthyridine-4-carboxamide;

3-71: 3-(3-fluoro-5-methylphenyl)-N-methyl-6-(pyrimidin-5-yl)-N-[(2S)-pyrrolidin-2-ylmethyl]quinoline-4-carboxamide;

3-72: 6-[4-cyano-6-(morpholin-4-yl)pyridin-2-yl]-3-(3-fluoro-5-methylphenyl)-N-methyl-N-[(2S)-pyrrolidin-2-ylmethyl]quinoline-4-carboxamide;

3-73: 3-(3-fluoro-5-methylphenyl)-N-methyl-6-[2-oxo-6-(trifluoromethyl)-2,3-dihydro-1H-1,3-benzodiazol-4-yl]-N-[(2S)-pyrrolidin-2-ylmethyl]quinoline-4-carboxamide;

3-74: 3-(3-fluoro-5-methylphenyl)-6-(4-fluoropyridin-3-yl)-N-methyl-N-[(2S)-pyrrolidin-2-ylmethyl]quinoline-4-carboxamide;

3-75: 6-(4-chloropyridin-3-yl)-3-(3-fluoro-5-methylphenyl)-N-methyl-N-[(2S)-pyrrolidin-2-ylmethyl]quinoline-4-carboxamide;

3-76: 6-(3-cyano-5-fluorophenyl)-3-(3,3-difluoropyrrolidin-1-yl)-N-methyl-N-[(2S)-pyrrolidin-2-ylmethyl]-1,5-naphthyridine-4-carboxamide;

3-77: 6-(6-carbamoylpyridin-2-yl)-3-(3,5-difluorophenyl)-N-methyl-N-[(2S)-pyrrolidin-2-ylmethyl]quinoline-4-carboxamide;

3-78: 6-(6-carbamoyl-3-fluoropyridin-2-yl)-3-(3-fluoro-5-methylphenyl)-N-methyl-N-[(2S)-pyrrolidin-2-ylmethyl]quinoline-4-carboxamide;

3-79: 6-(6-carbamoyl-3-methylpyridin-2-yl)-3-(3,5-difluorophenyl)-N-methyl-N-[(2S)-pyrrolidin-2-ylmethyl]quinoline-4-carboxamide;

3-80: 6-(4-carbamoylpyridin-2-yl)-3-(3-fluoro-5-methylphenyl)-N-methyl-N-[(2S)-pyrrolidin-2-ylmethyl]quinoline-4-carboxamide;

3-81: 3-(3-fluoro-5-methylphenyl)-6-(5-methoxypyridin-3-yl)-N-methyl-N-[(2S)-pyrrolidin-2-ylmethyl]quinoline-4-carboxamide;

3-82: 3-(3-fluoro-5-methylphenyl)-N-methyl-N-[(2S)-pyrrolidin-2-ylmethyl]-6-(6-sulfamoylpyridin-2-yl)quinoline-4-carboxamide;

3-83: 3-(3-fluoro-5-methylphenyl)-N-methyl-6-(5-methylpyridin-3-yl)-N-[(2S)-pyrrolidin-2-ylmethyl]quinoline-4-carboxamide;

3-84: 3-(3-fluoro-5-methylphenyl)-6-[5-(hydroxymethyl)pyridin-3-yl]-N-methyl-N-[(2S)-pyrrolidin-2-ylmethyl]quinoline-4-carboxamide;

3-85: 3-(3-chloro-5-methylphenyl)-6-(5-hydroxypyridin-3-yl)-N,7-dimethyl-N-[(2S)-pyrrolidin-2-ylmethyl]-3,4-dihydroquinazoline-4-carboxamide;

3-86: 6-[5-(difluoromethoxy)pyridin-3-yl]-3-(3-fluoro-5-methylphenyl)-N-methyl-N-[(2S)-pyrrolidin-2-ylmethyl]quinoline-4-carboxamide;

3-87: ethyl (2S)-2-({1-[6-(6-carbamoylpyridin-2-yl)-3-(3-fluoro-5-methylphenyl)quinolin-4-yl]-N-methylformamido}methyl)pyrrolidine-1-carboxylate;

3-88: 6-(6-carbamoylpyridin-2-yl)-3-(3-chloro-5-methylphenyl)-N-methyl-N-[(2S)-pyrrolidin-2-ylmethyl]quinoline-4-carboxamide;

3-89: 6-(6-carbamoyl-3-fluoropyridin-2-yl)-3-(3-chloro-5-methylphenyl)-N-methyl-N-[(2S)-pyrrolidin-2-ylmethyl]quinoline-4-carboxamide;

3-90: 6-(6-carbamoyl-3-methylpyridin-2-yl)-3-(3-chloro-5-methylphenyl)-N-methyl-N-[(2S)-pyrrolidin-2-ylmethyl]quinoline-4-carboxamide;

3-91: 6-(6-carbamoyl-3-chloropyridin-2-yl)-3-(3-chloro-5-methylphenyl)-N-methyl-N-[(2S)-pyrrolidin-2-ylmethyl]quinoline-4-carboxamide;

3-92: N-[(2S)-azetidin-2-ylmethyl]-6-(6-carbamoylpyridin-2-yl)-3-(3-fluoro-5-methylphenyl)-N-methylquinoline-4-carboxamide;

3-93: N-[(2S)-azetidin-2-ylmethyl]-6-(6-carbamoyl-3-fluoropyridin-2-yl)-3-(3-fluoro-5-methylphenyl)-N-methylquinoline-4-carboxamide;

3-94: N-[(2S)-azetidin-2-ylmethyl]-6-(6-carbamoyl-3-methylpyridin-2-yl)-3-(3-fluoro-5-methylphenyl)-N-methylquinoline-4-carboxamide;

3-95: N-[(2S)-azetidin-2-ylmethyl]-6-(6-carbamoyl-3-chloropyridin-2-yl)-3-(3-fluoro-5-methylphenyl)-N-methylquinoline-4-carboxamide;

3-96: 6-(6-carbamoylpyridin-2-yl)-3-(3,5-dichlorophenyl)-N-methyl-N-[(2S)-pyrrolidin-2-ylmethyl]quinoline-4-carboxamide;

3-97: 6-(6-carbamoyl-3-fluoropyridin-2-yl)-3-(3,5-dichlorophenyl)-N-methyl-N-[(2S)-pyrrolidin-2-ylmethyl]quinoline-4-carboxamide;

3-98: 6-(6-carbamoyl-3-methylpyridin-2-yl)-3-(3,5-dichlorophenyl)-N-methyl-N-[(2S)-pyrrolidin-2-ylmethyl]quinoline-4-carboxamide;

3-99: 6-(6-carbamoyl-3-chloropyridin-2-yl)-3-(3,5-dichlorophenyl)-N-methyl-N-[(2S)-pyrrolidin-2-ylmethyl]quinoline-4-carboxamide;

3-100: N-[(2S)-azetidin-2-ylmethyl]-6-(6-carbamoylpyridin-2-yl)-3-(3,5-dichlorophenyl)-N-methylquinoline-4-carboxamide;

3-101: N-[(2S)-azetidin-2-ylmethyl]-6-(6-carbamoyl-3-fluoropyridin-2-yl)-3-(3,5-dichlorophenyl)-N-methylquinoline-4-carboxamide;

3-102: N-[(2S)-azetidin-2-ylmethyl]-6-(6-carbamoyl-3-methylpyridin-2-yl)-3-(3,5-dichlorophenyl)-N-methylquinoline-4-carboxamide;

3-103: N-[(2S)-azetidin-2-ylmethyl]-6-(6-carbamoyl-3-chloropyridin-2-yl)-3-(3,5-dichlorophenyl)-N-methylquinoline-4-carboxamide;

3-104: 6-(6-carbamoylpyridin-2-yl)-3-(3-fluoro-5-methylphenyl)-N-methyl-N-{[(2S)-1-methylpyrrolidin-2-yl]methyl}quinoline-4-carboxamide;

3-105: 3-(3-fluoro-5-methylphenyl)-N-methyl-N-[(2S)-pyrrolidin-2-ylmethyl]-6-[5-(trifluoromethyl)pyridin-3-yl]quinoline-4-carboxamide;

3-106: 3-(3-fluoro-5-methylphenyl)-N-methyl-6-(4-oxo-3,4-dihydro-2H-1,3-benzoxazin-6-yl)-N-[(2S)-pyrrolidin-2-ylmethyl]quinoline-4-carboxamide;

3-107: 6-(3,5-difluoro-2-hydroxyphenyl)-3-(3-fluoro-5-methylphenyl)-N-methyl-N-[(2S)-pyrrolidin-2-ylmethyl]quinoline-4-carboxamide.

or a pharmaceutically acceptable salt, pharmaceutically acceptable solvate, diastereomeric mixture, or individual enantiomers thereof.

18. A pharmaceutical composition comprising a compound of claim 1, or a pharmaceutically acceptable salt, solvate, diastereomeric mixture, or individual enantiomers thereof, and at least one pharmaceutically acceptable excipient.

19. A method of treating a disease or condition in a mammal that would benefit from the modulation of the somatostatin receptor subtype 2 (SSTR2) activity comprising administering a compound of claim 1, or a pharmaceutically acceptable salt, pharmaceutically acceptable solvate, diastereomeric mixture, or individual enantiomers thereof, to the mammal in need thereof; wherein the disease or condition is acromegaly, a neuroendocrine tumor, or combinations thereof.

* * * * *